United States Patent
Okazaki et al.

(10) Patent No.: US 7,208,524 B2
(45) Date of Patent: Apr. 24, 2007

(54) 5-AMIDINO-2-HYDROXYBENZENESULFON-AMIDE DERIVATIVES, PHARMACEUTICAL COMPOSITIONS CONTAINING THE SAME AND INTERMEDIATES FOR THEIR PREPARATION

(75) Inventors: Kosuke Okazaki, Nagano (JP); Masahiko Uchida, Nagano (JP); Harunobu Mukaiyama, Nagano (JP); Hiroaki Kobayashi, Nagano (JP); Yuichiro Kai, Nagano (JP); Hideki Takeuchi, Nagano (JP); Kenji Yokoyama, Nagano (JP); Yoshihiro Terao, Nagano (JP); Yuji Hoyano, Nagano (JP); Hiroaki Shiohara, Nagano (JP); Norihiko Kikuchi, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/398,383

(22) PCT Filed: Oct. 2, 2001

(86) PCT No.: PCT/JP01/08670

§ 371 (c)(1),
(2), (4) Date: Jul. 8, 2003

(87) PCT Pub. No.: WO02/28827

PCT Pub. Date: Apr. 11, 2002

(65) Prior Publication Data

US 2006/0116361 A1 Jun. 1, 2006

(30) Foreign Application Priority Data

Oct. 4, 2000 (JP) .............................. 2000-305569
Jun. 25, 2001 (JP) .............................. 2001-191486

(51) Int. Cl.
*A61K 31/195* (2006.01)
*A61K 31/18* (2006.01)
*C07C 59/52* (2006.01)
*C07C 307/06* (2006.01)

(52) U.S. Cl. ..................... 514/562; 514/603; 562/469; 564/86

(58) Field of Classification Search .................. 564/86; 562/469; 514/562, 603
See application file for complete search history.

(56) References Cited

U.S. PATENT DOCUMENTS

2005/0107354 A1* 5/2005 Koizumi et al. ........ 514/210.01

FOREIGN PATENT DOCUMENTS

| WO | WO 0050390 | 8/2000 |
|---|---|---|
| WO | WO 0059876 | 10/2000 |
| WO | WO 02/28827 A1 | 4/2002 |

OTHER PUBLICATIONS

International Search Report.
Leo Alig, et al.; Low Molecular Weight, Non-Peptide Fibrinogen Receptor Antagonists; ;J. Med. Chem., vol. 35, No. 23, pp. 4393-4407 (1992).

* cited by examiner

*Primary Examiner*—Kamal A. Saeed
*Assistant Examiner*—Ebenezer Sackey
(74) *Attorney, Agent, or Firm*—Sughrue Mion, PLLC

(57) ABSTRACT

The present invention relates to a 5-amidino-2-hydroxybenzenesulfonamide derivative represented by the general formula:

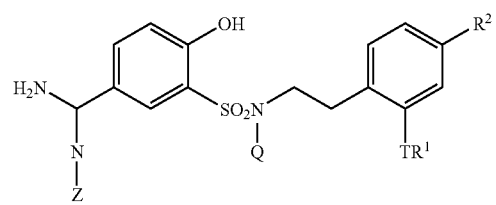

[I]

wherein $R^1$ is a hydrogen atom or an optionally substituted lower alkyl group;
$R^2$ is a di(lower alkyl)amino group, a lower alkyl group, a cycloalkyl group, an optionally substituted aryl group, an optionally substituted heterocycloalkyl group, or an optionally substituted aromatic heterocyclic group;
T is an oxygen atom, a sulfur atom, a sulfonyl group etc.;
Q is a hydrogen atom or an optionally substituted lower alkyl group; and
Z is a hydrogen atom, a hydroxy group etc.,
or a pharmaceutically acceptable salt thereof, which exert a potent and selective activated blood coagulation factor X inhibitory activity and is useful as an agent for the prevention or treatment of a disease occurred associating an activated blood coagulation factor X, a pharmaceutical composition comprising the same, a pharmaceutical use thereof and an intermediate thereof.

13 Claims, No Drawings

5-AMIDINO-2-HYDROXYBENZENESULFON-AMIDE DERIVATIVES, PHARMACEUTICAL COMPOSITIONS CONTAINING THE SAME AND INTERMEDIATES FOR THEIR PREPARATION

TECHNICAL FIELD

The present invention relates to novel 5-amidino-2-hydroxybenzenesulfonamide derivatives or pharmaceutical acceptable salts thereof which are useful as medicaments.

More particularly, the present invention relates to 5-amidino-2-hydroxybenzenesulfonamide derivatives or pharmaceutical acceptable salts thereof, which exert an excellent activated blood coagulation factor X inhibitory activity and are useful as activated blood coagulation factor X inhibitors, pharmaceutical compositions comprising the same, their pharmaceutical uses and intermediates for their preparation.

BACKGROUND ART

The anticoagulation therapy has been extensively performed for the prevention and treatment of thromboembolic diseases caused by accelerating blood clotting, and drugs such as heparin and warfarin potassium have been frequently used as anticoagulant agents at present.

However, it has been known that heparin has an antithrombin activity and activated blood coagulation factor X inhibitory activity and it is apt to cause bleeding tendency.

Warfarin potassium is an anticoagulant which controls biosynthesis of vitamin K-dependent coagulation factor, and it is difficult to control the anticoagulation capacity due to its action mechanism when this drug is used in the prevention and treatment of thromboembolic diseases. Therefore, this drug is extremely difficult to use clinically.

In recent years, selective thrombin inhibitors have been developed and have been used clinically. However, since thrombin plays a close part in the conversion of fibrinogen into fibrin in blood coagulation cascade reactions and platelet activation and aggregation, the thrombin inhibitors also have similar problems to those of heparin from the safety point of view such as bleeding tendency and it has been reported that their effects are not necessarily enough.

On the other hand, activated blood coagulation factor X, which acts at the joining point of the extrinsic and intrinsic blood coagulation cascade reactions, locates upstream to thrombin, so that coagulation inhibition is more efficient than that of thrombin inhibitors and therefore activated blood coagulation factor X inhibitors attract public attentions as drugs having a possibility that such an inhibition acts to the coagulation system effectively.

Furthermore, with the changes into European and American life styles and the increase in aged population in recent years, incidence of thromboembolic diseases such as myocardial infarction and arteriovenous obstruction will go on increasing, and therefore, demands on development of more effective anticoagulants are great and social importance of their treatment has been increasing more and more.

DISCLOSURE OF THE INVENTION

The present inventors have studied earnestly to find novel compounds having an excellent activated blood coagulation factor X inhibitory activity. As a result, it was surprisingly found that certain 5-amidino-2-hydroxybenzenesulfonamide derivatives show a potent and selective activated blood coagulation factor X inhibitory activity, thereby forming the basis of the present invention.

The present invention is to provide novel compounds which exert a potent and selective activated blood coagulation factor X inhibitory activity.

This is, the present invention relates to a 5-amidino-2-hydroxybenzenesulfonamide derivative represented by the general formula:

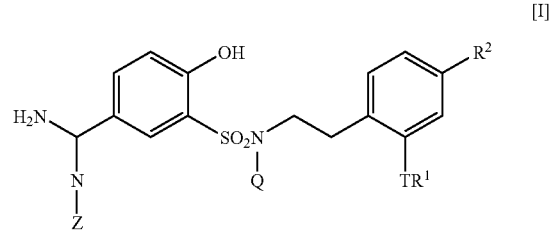

[I]

wherein $R^1$ represents a hydrogen atom or a lower alkyl group which may have a substituent selected from the following group (A);

(A) —$COOR^A$, —$CONR^BR^C$, a 3 to 10-membered cycloalkyl group, a 6 to 10-membered aryl group, a 3 to 10-membered heterocycloalkyl group which may have an oxo group, and a 5 to 10-membered aromatic heterocyclic group which may have an oxo group or a lower alkyl group;

wherein $R^A$ represents a hydrogen atom, a 3 to 10-membered cycloalkyl group or a lower alkyl group which may have a substituent selected from the following group (i);

(i) —$COOR^{A1}$ in which $R^{A1}$ is a hydrogen atom, a 3 to 10-membered cycloalkyl group or a lower alkyl group, —$OCOR^{A2}$ in which $R^{A2}$ is a 3 to 10-membered cycloalkyl group or a lower alkyl group, —$OCOOR^{A3}$ in which $R^{A3}$ is a 3 to 10-membered cycloalkyl group or a lower alkyl group, —$OR^{A4}$ in which $R^{A4}$ is a hydrogen atom, a 3 to 10-membered cycloalkyl group or a lower alkyl group, —$CONR^{A5}R^{A6}$ in which $R^{A5}$ and $R^{A6}$ are independently a hydrogen atom or a lower alkyl group, or —$NR^{A5}R^{A6}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

wherein $R^B$ and $R^C$ independently represent a hydrogen atom or a lower alkyl group which may have a substituent selected from the following group (ii), or —$NR^BR^C$ forms a cyclic amino group;

(ii) —$COOR^{B1}$ in which $R^{B1}$ is a hydrogen atom, a 3 to 10-membered cycloalkyl group or a lower alkyl group, —$CONR^{B2}R^{C2}$ in which $R^{B2}$ and $R^{C2}$ are independently a hydrogen atom or a lower alkyl group, or —$NR^{B2}R^{C2}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

T represents an oxygen atom, a sulfur atom or a sulfonyl group; or $TR^1$ represents —$SO_2NR^{B3}R^{C3}$ in which $R^{B3}$ and $R^{C3}$ are independently a hydrogen atom or a lower alkyl group;

$R^2$ represents a di(lower alkyl) amino group, a lower alkyl group, a 3 to 10-membered cycloalkyl group, a 6 to 10-membered aryl group which may have one to three substituents selected from the following group (B), a 3 to 10-membered heterocycloalkyl group which may have an oxo group, or a 5 to 10-membered aromatic heterocyclic group which may have a substituent selected from the following group (C);

(B) an oxo group, a lower alkyl group, a halo(lower alkyl) group, —Y—$R^D$, a halogen atom, a nitro group, an amino group, —COOR$^E$, a carbamoyl group, a sufamoyl group, a lower alkylsulfonyl group, a mono(lower alkyl)sulfamoyl group which may have —COOR$^F$, and a lower alkylsulfonylamino-substituted (lower alkyl) group;

wherein Y represents an oxygen atom or a sulfur atom;

$R^D$ represents a hydrogen atom, a halo(lower alkyl) group or a lower alkyl group which may have —COOR$^{D1}$ in which $R^{D1}$ is a hydrogen atom, a 3 to 10-membered cycloalkyl group or a lower alkyl group;

$R^E$ represents a hydrogen atom, a 3 to 10-membered cycloalkyl group or a lower alkyl group;

$R^F$ represents a hydrogen atom, a 3 to 10-membered cycloalkyl group or a lower alkyl group;

(C) a lower alkyl group, an amino group and —COOR$^G$;

wherein $R^G$ represents a hydrogen atom, a 3 to 10-membered cycloalkyl group or a lower alkyl group;

Q represents a hydrogen atom or a lower alkyl group which may have a substituent selected from the following group (D);

(D) —OR$^H$, —COOR$^I$, —CONR$^J$R$^K$, a 6 to 10-membered aryl group which may have one to three substituents selected from the following group (iii), and a 5 to 10-membered aromatic heterocyclic group which may have one to three substituents selected from the following group (iv);

wherein $R^H$ represents a hydrogen atom or a lower alkyl group which may have —OR$^{H1}$ in which $R^{H1}$ is a hydrogen atom or a lower alkyl group;

$R^I$ independently has the same meaning as $R^A$;

$R^J$ and $R^K$ independently represent a hydrogen atom, a 6 to 10-membered aryl group which may have a carbamoyl group, a 5 to 10-membered aromatic heterocyclic group which may have a substituent selected from the following group (v), or a lower alkyl group which may have a substituent selected from the following group (vi), or —NR$^J$R$^K$ forms a cyclic amino group which may have a substituent selected from the following group (vii);

(v) a halogen atom, a lower alkyl group, a carbamoyl group and —COOR$^{J1}$ in which $R^{J1}$ is a hydrogen atom or a lower alkyl group;

(vi) —OR$^{J2}$ in which $R^{J2}$ is a hydrogen atom or a lower alkyl group, and a 5 to 10-membered aromatic heterocyclic group;

(vii) a hydroxy group, a lower alkyl group, a hydroxy (lower alkyl) group, a carbamoyl group, a di(lower alkyl)amino group, a lower acyl group and —COOR$^{J3}$ in which $R^{J3}$ is a hydrogen atom or a lower alkyl group;

(iii) a halogen atom, a nitro group, a lower alkyl group, —OR$^L$ in which $R^L$ is a hydrogen atom or a lower alkyl group, and —COOR$^M$ in which $R^M$ is a hydrogen atom or a lower alkyl group;

(iv) a halogen atom, an oxo group, a lower alkyl group and a phenyl group; and

Z represents a hydrogen atom, a ydroxyl group or —COOR$^N$;

wherein $R^N$ represents a halo(lower alkyl) group, a 6 to 10-membered aryl group, or a lower alkyl group which may have a substituent selected from the following group (viii);

(viii) —OR$^{N1}$ in which $R^{N1}$ is a hydrogen atom or a lower alkyl group, —COOR$^{N2}$ in which $R^{N2}$ is a lower alkyl group which may have —COOR$^{N21}$ where $R^{N21}$ is a lower alkyl group, —CONR$^{N3}$R$^{N4}$ in which $R^{N3}$ and $R^{N4}$ are independently a hydrogen atom or a lower alkyl group, or —NR$^{N3}$R$^{N4}$ forms a cyclic amino group, —OCOR$^{N5}$ in which $R^{N5}$ is a lower alkyl group which may have —OCOR$^{N51}$ where $R^{N51}$ is a lower alkyl group, a 3 to 10-membered heterocycloalkyl group and a 6 to 10-membered aryl group;

or a pharmaceutically acceptable salt thereof.

In another aspect, the present invention relates to a 5-amidino-2-hydroxybenzenesulfonamide derivative represented by the general formula [I] above or a pharmaceutically acceptable salt thereof wherein Q is a hydrogen atom and Z is not a hydrogen atom.

In still another aspect, the present invention relates to a 5-amidino-2-hydroxybenzenesulfonamide derivative as in the proceeding paragraph above wherein Q is a hydrogen atom and Z is not a hydrogen atom or a pharmaceutically acceptable salt thereof:

wherein $R^1$ is a lower alkyl group having —COOR$^4$ wherein $R^4$ is a hydrogen atom, a 3 to 10-membered cycloalkyl group or a lower alkyl group which may have a substituent selected from the following group (i);

(i) —COOR$^{41}$ in which $R^{41}$ is a hydrogen atom, a 3 to 10-membered cycloalkyl group or a lower alkyl group, —OCOR$^{42}$ in which $R^{42}$ is a 3 to 10-membered cycloalkyl group or a lower alkyl group, —OCOOR$^{43}$ in which $R^{43}$ is a 3 to 10-membered cycloalkyl group or a lower alkyl group, —OR$^{44}$ in which $R^{44}$ is a hydrogen atom, a 3 to 10-membered cycloalkyl group or a lower alkyl group, —CONR$^{45}$R$^{46}$ in which $R^{45}$ and $R^{46}$ are independently a hydrogen atom or a lower alkyl group, or —NR$^{45}$R$^{46}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

$R^2$ is a phenyl group having a substituent selected from the following group (B);

(B) an oxo group, a lower alkyl group, a halo(lower alkyl) group, —Y-R$^D$, a halogen atom, a nitro group, an amino group, —COOR$^E$, a carbamoyl group, a sufamoyl group, a lower alkylsulfonyl group, a mono(lower alkyl)sulfamoyl group which may have —COOR$^F$, and a lower alkylsulfonylamino-substituted (lower alkyl) group;

wherein Y is an oxygen atom or a sulfur atom;

$R^D$ is a hydrogen atom, a halo(lower alkyl) group or a lower alkyl group which may have —COOR$^{D1}$ in which $R^{D1}$ is a hydrogen atom, a 3 to 10-membered cycloalkyl group or a lower alkyl group;

$R^E$ is a hydrogen atom, a 3 to 10-membered cycloalkyl group or a lower alkyl group;

$R^F$ is a hydrogen atom, a 3 to 10-membered cycloalkyl group or a lower alkyl group;

T is an oxygen atom; and

Z is a hydroxy group.

In still yet a further aspect, the present invention relates to a 5-amidino-2-hydroxybenzenesulfonamide derivative as in the proceeding still another aspect of the present invention or a pharmaceutically acceptable salt therof;

wherein $R^1$ is a methyl group having —COOR$^{410}$ wherein $R^{410}$ is a 3 to 10-membered cycloalkyl group or a lower alkyl group; and $R^2$ is a phenyl group having a substituent selected from the group consisting of a sufamoyl group, a lower alkylsulfonyl group and a mono(lower alkyl)sulfamoyl group.

The present invention also relates to a pharmaceutical composition comprising as an active ingredient a 5-amidino-2-hydroxybenzenesulfonamide derivative represented by the above general formula (I) or a pharmaceutically acceptable salt thereof.

The present invention relates to an activated blood coagulation factor X inhibitor comprising as an active ingredient a 5-amidino-2-hydroxybenzenesulfonamide derivative represented by the above general formula (I) or a pharmaceutically acceptable salt thereof.

The present invention relates to an agent for the prevention or treatment of a disease occurred associating an activated blood coagulation factor X, which comprises as an active ingredient a 5-amidino-2-hydroxybenzenesulfonamide derivative represented by the above general formula (I) or a pharmaceutically acceptable salt thereof.

The present invention relates to a method for the prevention or treatment of a disease occurred associating an activated blood coagulation factor X, which comprises administering a therapeutically effective amount of a 5-amidino-2-hydroxybenzenesulfonamide derivative represented by the above general formula (I) or a pharmaceutically acceptable salt thereof.

The present invention relates to a use of a 5-amidino-2-hydroxybenzenesulfonamide derivative represented by the above general formula (I) or a pharmaceutically acceptable salt thereof for the manufacture of a pharmaceutical composition for the prevention or treatment of a disease occurred associating an activated blood coagulation factor X.

Furthermore, the present invention relates to a 5-cyano-2-hydroxybenzenesulfonamide derivative represented by the general formula:

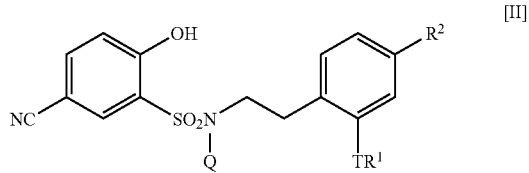

[II]

wherein $R^1$ represents a hydrogen atom or a lower alkyl group which may have a substituent selected from the following group (A);

(A) —COOR , —CONR$^B$R$^C$, a 3 to 10-membered cycloalkyl group, a 6 to 10-membered aryl group, a 3 to 10-membered heterocycloalkyl group which may have an oxo group, and a 5 to 10-membered aromatic heterocyclic group which may have an oxo group or a lower alkyl group;
  wherein $R^A$ represents a hydrogen atom, a 3 to 10-membered cycloalkyl group or a lower alkyl group which may have a substituent selected from the following group (i);
  (i) —COOR$^{41}$ in which $R^{41}$ is a hydrogen atom, a 3 to 10-membered cycloalkyl group or a lower alkyl group, —OCOR$^{42}$ in which $R^{42}$ is a 3 to 10-membered cycloalkyl group or a lower alkyl group, —OCOOR$^{43}$ in which $R^{43}$ is a 3 to 10-membered cycloalkyl group or a lower alkyl group, —OR$^{44}$ in which $R^{44}$ is a hydrogen atom, a 3 to 10-membered cycloalkyl group or a lower alkyl group, —CONR$^{45}$R$^{46}$ in which $R^{45}$ and $R^{46}$ are independently a hydrogen atom or a lower alkyl group, or —NR$^{45}$R$^{46}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;
  wherein $R^B$ and $R^C$ independently represent a hydrogen atom or a lower alkyl group which may have a substituent selected from the following group (ii), or —NR$^B$R$^C$ forms a cyclic amino group;
  (ii) —COOR$^{B1}$ in which $R^{B1}$ is a hydrogen atom, a 3 to 10-membered cycloalkyl group or a lower alkyl group, —CONR$^{B2}$R$^{C2}$ in which $R^{B2}$ and $R^{C2}$ are independently a hydrogen atom or a lower alkyl group, or —NR$^{B2}$R$^{C2}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

T represents an oxygen atom, a sulfur atom or a sulfonyl group; or TR$^1$ represents —SO$_2$NR$^{B3}$R$^{C3}$ in which $R^{B3}$ and $R^{C3}$ are independently a hydrogen atom or a lower alkyl group;

$R^2$ represents a di(lower alkyl)amino group, a lower alkyl group, a 3 to 10-membered cycloalkyl group, a 6 to 10-membered aryl group which may have one to three substituents selected from the following group (B), a 3 to 10-membered heterocycloalkyl group which may have an oxo group, or a 5 to 10-membered aromatic heterocyclic group which may have a substituent selected from the following group (C);

(B) an oxo group, a lower alkyl group, a halo(lower alkyl) group, —Y—R$^D$, a halogen atom, a nitro group, an amino group, —COOR$^E$, a carbamoyl group, a sufamoyl group, a lower alkylsulfonyl group, a mono(lower alkyl)sulfamoyl group which may have —COOR$^F$, and a lower alkylsulfonylamino-substituted (lower alkyl) group;
  wherein Y represents an oxygen atom or a sulfur atom;
  $R^D$ represents a hydrogen atom, a halo(lower alkyl) group or a lower alkyl group which may have —COOR$^{D1}$ in which $R^{D1}$ is a hydrogen atom, a 3 to 10-membered cycloalkyl group or a lower alkyl group;
  $R^E$ represents a hydrogen atom, a 3 to 10-membered cycloalkyl group or a lower alkyl group;
  $R^F$ represents a hydrogen atom, a 3 to 10-membered cycloalkyl group or a lower alkyl group;
(C) a lower alkyl group, an amino group and —COOR$^G$;
  wherein $R^G$ represents a hydrogen atom, a 3 to 10-membered cycloalkyl group or a lower alkyl group;

Q represents a hydrogen atom or a lower alkyl group which may have a substituent selected from the following group (D);

(D) —OR$^H$, —COOR$^I$, —CONR$^J$R$^K$, a 6 to 10-membered aryl group which may have one to three substituents selected from the following group (iii), and a 5 to 10-membered aromatic heterocyclic group which may have one to three substituents selected from the following group (iv);
wherein $R^H$ represents a hydrogen atom or a lower alkyl group which may have —OR$^{H1}$ in which $R^{H1}$ is a hydrogen atom or a lower alkyl group;
$R^I$ independently has the same meaning as $R^A$;
$R^J$ and $R^K$ independently represent a hydrogen atom, a 6 to 10-membered aryl group which may have a carbamoyl group, a 5 to 10-membered aromatic heterocyclic group which may have a substituent selected from the following group (v), or a lower alkyl group which may have a substituent selected from the following group (vi), or —NR$^J$R$^K$ forms a cyclic amino group which may have a substituent selected from the following group (vii);

(v) a halogen atom, a lower alkyl group, a carbamoyl group and —COOR$^{J1}$ in which R$^{J1}$ is a hydrogen atom or a lower alkyl group;

(vi) —OR$^{J2}$ in which R$^{J2}$ is a hydrogen atom or a lower alkyl group, and a 5 to 10-membered aromatic heterocyclic group;

(vii) a hydroxy group, a lower alkyl group, a hydroxy(lower alkyl) group, a carbamoyl group, a di(lower alkyl)amino group, a lower acyl group and —COOR$^{J3}$ in which R$^{J3}$ is a hydrogen atom or a lower alkyl group;

(iii) a halogen atom, a nitro group, a lower alkyl group, —OR$^L$ in which R$^L$ is a hydrogen atom or a lower alkyl group, and —COOR$^M$ in which R$^M$ is a hydrogen atom or a lower alkyl group; and (iv) a halogen atom, an oxo group, a lower alkyl group and a phenyl group;

or a salt thereof.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a pentyl group, an isopentyl group, a neopentyl group, a 1-methylbutyl group, a 2-methylbutyl group, a hexyl group or the like. The term "lower alkylsulfonyl group" means a sulfonyl group having the above lower alkyl group, such as a methanesulfonyl group, an ethanesulfonyl group, a propanesulfonyl group, an isopropanesulfonyl group, a butanesulfonyl group, an isobutanesulfonyl group, a sec-butanesulfonyl group, a pentanesulfonyl group, an isopentanesulfonyl group, a neopentanesulfonyl group, a hexanesulfonyl group or the like. The term "mono(lower alkyl)sulfamoyl group" means a monoalkylsulfamoyl group wherein the alkyl moiety is the same as the above lower alkyl group. The term "di(lower alkyl)amino group" means an amino group di-substituted by same or different lower alkyl groups as defined above. The term "lower alkylsulfonyl-amino-substituted (lower alkyl) group" means the above alkyl group having an amino group N-substituted by the above lower alkylsulfonyl group. The term "hydroxy(lower alkyl) group" means a straight-chained or branched alkyl group having 2 to 6 carbon atoms and substituted by a hydroxy group. The term "lower acyl group" means a straight-chained or branched alkoxycarbonyl group having 2 to 6 carbon atoms such as an acetyl group, a propionyl group, a butyryl group, an isobutyryl group, a valeryl group, a hexanoyl group or the like. The term "lower alkylene group" means a straight-chained or branched alkylene group having 1 to 6 carbon atoms such as a methylene group, an ethylene group, a trimethylene group, a propylene group or the like.

The term "3 to 10-membered cycloalkyl group" means a 3 to 7-membered monocyclic aliphatic alkyl group such as a cyclopropyl group, a cyclobutyl group, a cyclopentyl group, a cyclohexyl group or a cycloheptyl group, or a cyclopentyl group or a cyclohexyl group which are fused with a benzene ring. The term "6 to 10-membered aryl group" means a phenyl group, a naphthyl group, or a phenyl group which is fused with a cyclopentane ring or a cyclohexane ring.

The term "3 to 10-membered heterocycloalkyl group" means a 3 to 7-membered monocyclic heteroalkyl group containing one to two hetero atoms selected from a nitrogen atom, an oxygen atom and a sulfur atom in the ring, or a bicyclic heteroalkyl group which is benzene-fused 5 or 6-membered monocyclic heteroalkyl group as defined above, and as examples of such groups, for example, a monovalent group derived from morpholine, thiomorpholine, pyrrolidine, imidazoline, oxazoline, piperidine, piperazine, tetrahydrofuran, aziridine, azetidine, indoline, isoindoline, chroman, isochroman or the like can be illustrated. As examples of heterocycloalkyl group having an oxo group, for example, a monovalent group derived from a 2-oxazolidone or the like.

The term "5 to 10-membered aromatic heterocyclic group" means a 5 to 6-membered monocyclic aromatic group containing one to four hetero atoms selected from a nitrogen atom, an oxygen atom and a sulfur atom in the ring, or a bicyclic heteroalkyl group which is benzene or pyridine-fused 5 or 6-membered monocyclic aromatic group as defined above, and as examples of such groups, for example, a monovalent group derived from pyridine, pyrimidine, pyrazine, pyridazine, pyrrole, thiophene, oxazole, thiazole, imidazole, pyrazole, oxadiazole, thiodiazole, tetrazole, indole, indolizine, benzofuran, benzothiophene, quinoline, isoquinoline, phthalazine, naphthyridine, quinoxaline, quinazoline, cinnoline or the like can be illustrated. As examples of aromatic heterocyclic group having an oxo group, for example, a monovalent group derived from a 1,3,4-oxadiazol-2-one or the like can be illustrated.

The term "cyclic amino group" means a 5 to 6-membered monocyclic amino group which may contain one hetero atom selected from a nitrogen atom, an oxygen atom and a sulfur atom other than the nitrogen atom at the binding site in the ring, such as a 1-pyrrolodinyl group, a piperidino group, a morpholino group, a thiomorpholino group, a 1-piperazinyl group or the like.

The term "halogen atom" means a fluorine atom, a chlorine atom, a bromine atom or an iodine atom. The term "halo(lower alkyl) group" means the above alkyl group substituted by one to three halogen atom as defined above, such as a trifluoromethyl group, a 2,2,2-trifluoroethyl group or the like.

The term "hydroxy-protective group" means a hydroxy-protective group used generally in organic synthesis, which is described in PROTECTIVE GROUPS IN ORGANIC SYNTHESIS, THEODORA W. GREENE, PETER G. WUTS by JOHN WILEY&SONS, INC, such as a benzyl group, a methoxymethyl group, an acetyl group or the like.

For example, the compounds represented by the above general formula (I) of the present invention can be prepared by allowing a 5-cyano-2-hydroxybenzenesulfonamide derivative represented by the above general formula (II) or a salt thereof to react with an alcohol in the presence of hydrogen chloride (hereinafter referred to as Process 1), allowing the resulting compound to react with ammonia or a salt thereof, or hydroxylamine or a salt thereof (hereinafter referred to as Process 2), carrying out, as occasion demands, suitably one to four processes selected from the group consisting of (1) hydrolysis of the resulting ester group (hereinafter referred to as Process 3), (2) ester interchange or esterification of the resulting compound using an alcohol compound represented by the general formula:

                [III]

wherein R$^4$ has the same meaning as defined above, or esterification of the resulting compound using a compound represented by the general formula:

                [IV]

wherein $X^1$ represents a leaving group such as a halogen atom, a toluenesulfonyloxy group, a methanesulfonyloxy group or the like; and $R^4$ has the same meaning as defined above (hereinafter referred to as Process 4), (3) introduction of a protective group into a phenolic hydroxy group (hereinafter referred to as Process 5) and (4) N-acylation of the resulting compound using a compound represented by the general formula:

$$R^NOCO-X^2 \qquad [V]$$

wherein $X^2$ represents a leaving group such as a halogen atom, a 4-nitrophenoxy group or the like; and $R^N$ has the same meaning as defined above, and subjecting, as occasion demands, to removal of the protective group of the phenolic hydroxy group or O-deacylation in the usual way.

In the aforementioned production process, the reaction from a 5-cyano-2-hydroxybenzenesulfonamide derivative represented by the above general formula (II) into a 5-amidino-2-hydroxybenzenesulfonamide derivative represented by the above general formula (I) is as follows in detail.

Process 1

A corresponding imidate compound can be prepared by allowing a 5-cyano-2-hydroxybenzenesulfonamide derivative represented by the above general formula (II) to react with an alcohol such as methanol or ethanol in the presence of a hydrogen halide such as hydrogen chloride or hydrogen bromide at usually −20° C. to room temperature. As a solvent used, methanol, ethanol, a mixed solvent of such alcohol with tetrahydrofuran, dichloromethane or N,N-dimethylformamide, and the like can be illustrated. The reaction time is usually from 1 hour to 3 days, varying based on sorts and volumes of a used starting material and solvent.

Process 2

A corresponding amidino compound can be prepared by allowing an imidate compound to react with ammonia or an ammonium salt such as ammonium carbonate, ammonium chloride or ammonium acetate, or hydroxylamine or a salt thereof in the presence or absence of a base such as triethylamine at usually 0° C. to room temperature. As a solvent used, methanol, ethanol, tetra-hydrofuran, dichloromethane and the like can be illustrated. The reaction time is usually from 1 hour to 3 days, varying based on sorts and volumes of a used starting material and solvent.

Process 3

In case of compounds having an ester group in the amidino derivatives obtained by Process 2, a corresponding carboxylic acid compound can be prepared by subjecting such compound to hydrolysis using an acid such as hydrochloric acid or sulfuric acid at usually room temperature to reflux temperature, or a base such as sodium hydroxide at usually 0° C. to reflux temperature. As a solvent used, water, acetonitrile, tetrahydrofuran, alcohols, a mixed solvent thereof and the like can be illustrated. The reaction time is usually from 1 hour to 2 days, varying based on sorts and volumes of a used starting material and solvent.

Process 4

A corresponding ester compound can be prepared by 1) subjecting an amidino derivative having an ester group or a carboxy group obtained by Process 2 or 3 to ester interchange or esterification using an alcohol compound represented by the above general formula (III) in the presence of an acid such as hydrochloric acid, sulfuric acid or p-toluenesulfonic acid at usually 0° C. to reflux temperature, by 2) subjecting a compound having a carboxy group of the amidino derivatives obtained by Process 2 or 3 to esterification using an alcohol compound represented by the above general formula (III) in the presence of a condensing agent such as 1-(3-dimethylaminopropyl)-3-ethylcarbodiimide hydrochloride at usually 0° C. to reflux temperature, or by 3) subjecting a compound having a carboxy group of the amidino derivatives obtained by Process 2 or 3 to esterification using a compound represented by the above general formula (IV) in the presence of a base such as potassium carbonate or triethylamine, or silver carbonate at usually 0° C. to reflux temperature. As a solvent used, an aprotic solvent such as tetrahydrofuran and the like can be illustrated. The reaction time is usually from 1 hour to 2 days, varying based on sorts and volumes of a used starting material and solvent.

Process 5

A corresponding O-protected compound can be prepared by suitably protecting a phenolic hydroxy group of a compound having an amidino group obtained by Processes 2–4 according to a method described in PROTECTIVE GROUPS IN ORGANIC SYNTHESIS, THEODORA W. GREENE, PETER G. WUTS by JOHN WILEY&SONS, INC.

Process 6

A corresponding carbamate compound can be prepared by allowing a compound having an amidino group obtained by Processes 2–5 to react with a compound represented by the above general formula (V) in the presence or absence of a base such as triethylamine or diisopropylethylamine at usually 0° C. to room temperature. As a solvent used, N,N-dimethylformamide and the like can be illustrated. The reaction time is usually from 1 hour to 2 days, varying based on sorts and volumes of a used starting material and solvent.

The removal of the protective group of the hydroxy group can be commonly carried out according to a method described in PROTECTIVE GROUPS INORGANIC SYNTHESIS, THEODORA W. GREENE, PETER G. WUTS by JOHN WILEY&SONS, INC.

Of the compounds represented by the above general formula (I) of the present invention, a compound represented by the general formula:

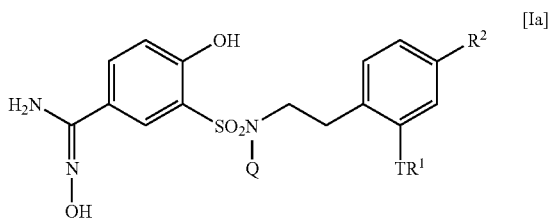

wherein Q, $R^1$, $R^2$ and T have the same meanings as defined above, can be also prepared by allowing a 5-cyano-2-hydroxy-benzenesulfonamide derivative represented by the above general formula (II) or a salt thereof to react with hydroxylamine or a salt thereof in the presence or absence of a base (hereinafter referred to as Process 9), and subjecting, as occasion demands, the resulting compound to ester interchange or esterification using an alcohol compound represented by the above general formula (III), or to esterification using a compound represented by the above general formula (IV) (hereinafter referred to as Process 10). In case that 5-cyano-2-hydroxybenzenesulfonamide derivatives represented by the above general formula (II) as starting materials have a carboxy group, it is preferable that Process 9 is carried out after converting it into an inorganic salt of a corresponding carboxylic acid (e.g. a sodium salt, a potassium salt) (hereinafter referred to as Process 8). In case that 5-cyano-2-hydroxybenzenesulfonamide derivatives represented by the above general formula (II) as starting materials have an ester group, it is preferable that Process 9 is carried out after hydrolysis of the ester group (hereinafter referred to as Process 7) and Process 8.

In the aforementioned production process, the reaction from a 5-cyano-2-hydroxybenzenesulfonamide derivative represented by the above general formula (II) into a 5-amidino-2-hydroxybenzenesulfonamide derivative represented by the above general formula (Ia) is as follows in detail.

Process 7

A corresponding carboxylic acid compound can be prepared by subjecting a corresponding 5-cyano-2-hydroxybenzene-sulfonamide derivative having an ester group to hydrolysis using an acid such as hydrochloric acid or sulfuric acid at usually room temperature to reflux temperature, or using a base such as sodium hydroxide at usually 0° C. to reflux temperature. As a solvent used, water, acetonitrile, tetrahydrofuran, alcohols, a mixed solvent thereof and the like can be illustrated. The reaction time is usually from 1 hour to 2 days, varying based on sorts and volumes of a used starting material and solvent.

Process 8

A corresponding 5-cyano-2-hydroxybenzenesulfonamide derivative having a carboxy group can be converted by treating with a base such as sodium hydroxide or potassium hydroxide in the presence of various solvents or without any solvent at usually −20° C. to room temperature into a corresponding inorganic salt of the carboxylic acid compound. As a solvent used, water, ethanol, tetrahydrofuran, a mixed solvent thereof and the like can be illustrated. The reaction time is usually from 1 hour to 2 days, varying based on sorts and volumes of a used starting material and solvent.

Process 9

A corresponding amidoxime compound can be prepared by allowing a 5-cyano-2-hydroxybenzenesulfonamide derivative represented by the above general formula (II), which is obtained by treating according to Processes 7 and 8 as occasion demands, to react with hydroxylamine or a salt thereof in the presence or absence of a base such as triethylamine at usually 50° C. to reflux temperature. As a solvent used, water, methanol, ethanol, tetrahydrofuran, toluene, a mixed solvent thereof and the like can be illustrated. The reaction time is usually from 1 hour to 3 days, varying based on sorts and volumes of a used starting material and solvent.

Process 10

A corresponding ester compound can be prepared by 1) subjecting an amidoxime compound having an ester group or a carboxy group obtained by Process 9 to ester interchange or esterification using an alcohol compound represented by the above general formula (III) in the presence of an acid such as hydrochloric acid, sulfuric acid or p-toluenesulfonic acid at usually 0° C. to reflux temperature, by 2) subjecting an amidoxime derivative having a carboxy group obtained by Process 9 to esterification using an alcohol compound represented by the above general formula (III) in the presence of a condensing agent such as 1-(3-dimethylaminopropyl)-3-ethylcarbodiimide hydrochloride at usually 0° C. to reflux temperature, or by 3) subjecting an amidino derivative having a carboxy group obtained by Process 9 to esterification using a compound represented by the above general formula (IV) in the presence of a base such as potassium carbonate or triethylamine, or silver carbonate at usually 0° C. to reflux temperature. As a solvent used, an aprotic solvent such as tetrahydrofuran and the like can be illustrated. The reaction time is usually from 1 hour to 2 days, varying based on sorts and volumes of a used starting material and solvent.

Of the compounds represented by the above general formula (I), a compound represented by the general formula:

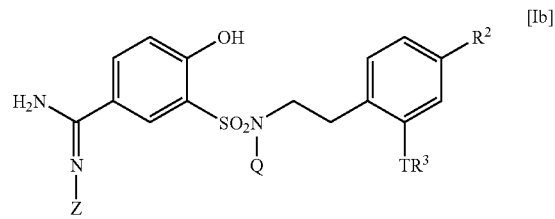

[Ib]

wherein $R^3$ represents —COOR$^{47}$ in which $R^{47}$ is a lower alkyl group having —CONR$^{45}$R$^{46}$ where $R^{45}$ and $R^{46}$, or —NR$^{45}$R$^{46}$ have the same meanings as defined above, or a lower alkyl group having —CONR$^B$R$^C$ where $R^B$ and $R^C$, or —NR$^B$R$^C$ have the same meanings as defined above; and $R^2$, Q, T and Z have the same meanings as defined above, can be prepared by allowing a compound represented by the general formula:

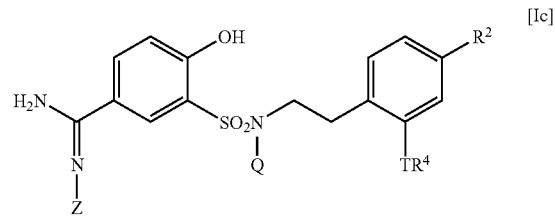

[Ic]

wherein $R^4$ represents —COOR$^{48}$ in which $R^{48}$ is a hydrogen atom or a lower alkyl group having —COOH; and $R^2$, Q, T and Z have the same meanings as defined above, or a salt thereof to react with an amine compound represented by the general formula:

HNR$^{45}$R$^{46}$ [VI]

wherein $R^{45}$ and $R^{46}$, or —NR$^{45}$R$^{46}$ have the same meanings as defined above, or a salt thereof, or an amine compound represented by the general formula:

HNR$^B$R$^C$ [VII]

wherein $R^{45}$ and $R^{46}$, or —NR$^{45}$R$^{46}$ have the same meanings as defined above, or a salt thereof (hereinafter referred to as Process 11).

In the aforementioned production process, the reaction from a 5-amidino-2-hydroxybenzenesulfonamide derivative represented by the above general formula (Ic) into a 5-amidino-2-hydroxybenzenesulfonamide derivative represented by the above general formula (Ib) is as follows in detail.

Process 11

A 5-amidino2-hydroxybenzenesulfonamide derivative represented by the above general formula (Ib) can be prepared by allowing a 5-amidino-2-hydroxybenzenesulfonamide derivative represented by the above general formula (Ic) or a salt thereof to react with an amine compound represented by the above general formula (VI) or a salt thereof, or an amine compound represented by the above general formula (VII) or a salt thereof in the presence of a condensing agent such as 1-(3-dimethylaminoproyl)-3-ethyl-carbodiimide hydrochloride, diphenylphoshoryl azide or the like and in the presence or absence of an agent for making an activated ester such as 1-hydroxybenzotriazole monohydrate and a base such as triethylamine at usually 0° C. to room temperature. As a solvent used, dichloromethane, N,N-dimethylformamide and the like can be illustrated. The reaction time is usually from 1 hour to 2 days, varying based on sorts and volumes of a used starting material and solvent.

For example, the 5-cyano-2-hydroxybenzenesulfonamide derivatives represented by the above general formula (II) used as starting materials in the aforementioned production processes can be prepared by the following method:

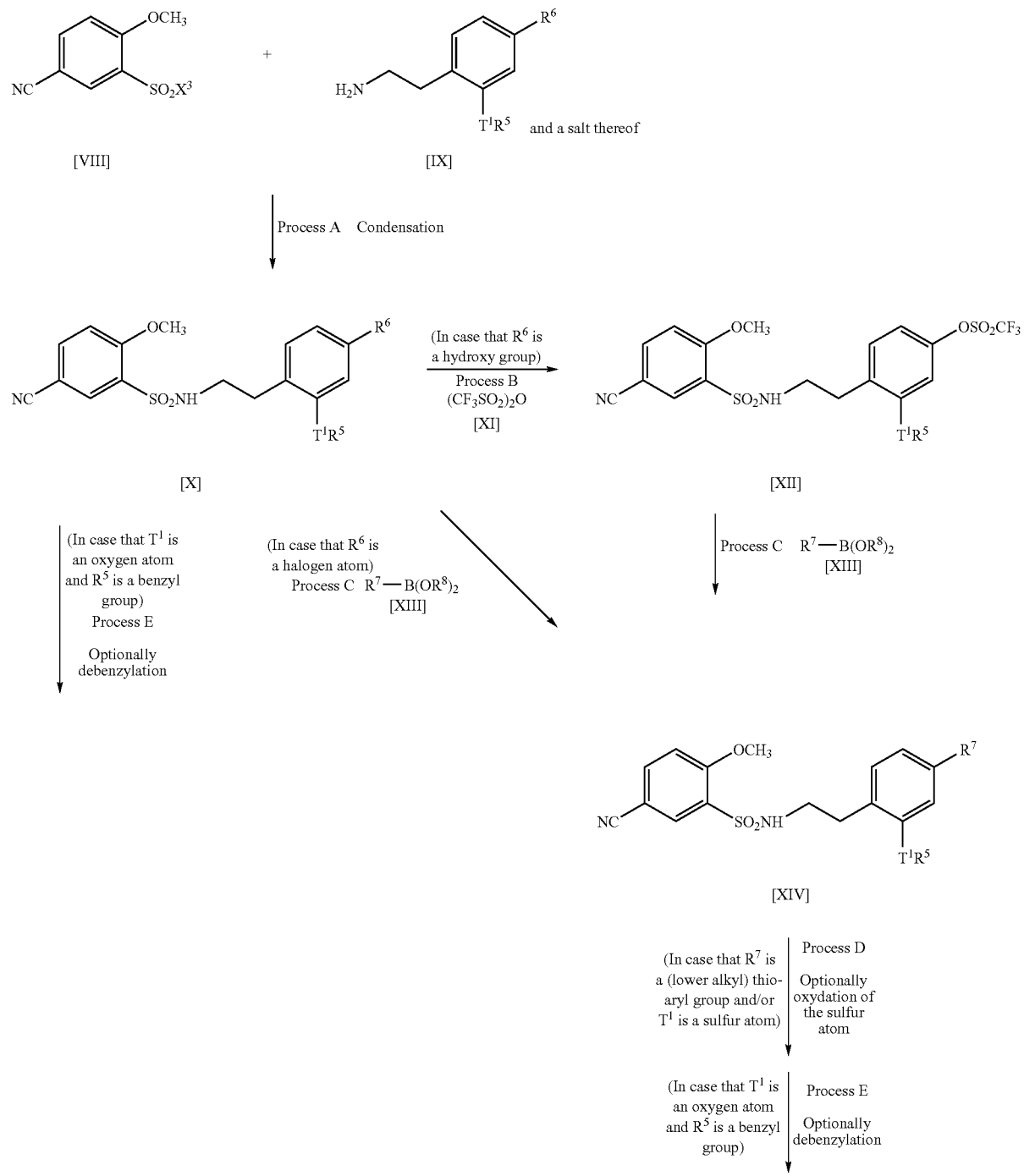

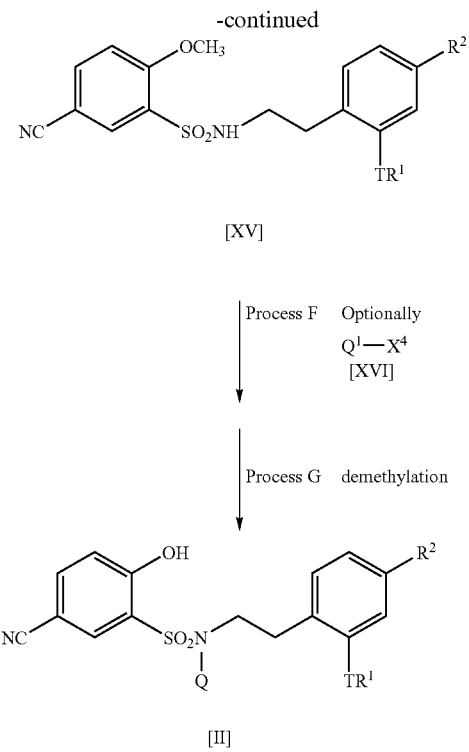

[XV]

Process F  Optionally
Q¹—X⁴
[XVI]

Process G  demethylation

[II]

wherein R⁵ represents a lower alkyl group which may have a substituent selected from the following group (A);
(A) —COOR^A, —CONR^B R^C, a 3 to 10-membered cycloalkyl group, a 6 to 10-membered aryl group, a 3 to 10-membered heterocycloalkyl group which may have an oxo group, and a 5 to 10-membered aromatic heterocyclic group which may have an oxo group or a lower alkyl group;
wherein R^A, R^B and R^C, or —NR^B R^C have the same meanings as defined above;
R⁶ represents a halogen atom, a ydroxyl group, a di(lower alkyl)amino group, a lower alkyl group, a 3 to 10-membered cycloalkyl group, or a 3 to 10-membered heterocycloalkyl group which may have an oxo group;
R⁷ represents a 5 to 10-membered aromatic heterocyclic group which may have a substituent selected from the following group (C), or a 6 to 10-membered aryl group which may have one to three substituents selected from the following group (E);
(C) a lower alkyl group, an amino group and —COOR^G in which R^G has the same meaning as defined above;
(E) an oxo group, a lower alkyl group, a halo(lower alkyl) group, —Y—R^D, a halogen atom, a nitro group, an amino group, —COOR^E, a carbamoyl group, a sufamoyl group, a mono(lower alkyl)sulfamoyl group which may have —COOR^F, and a lower alkylsulfonylamino-substituted (lower alkyl) group;
wherein R^D, R^E, R^F and Y have the same meanings as defined above
R⁸ represents a hydrogen atom or a lower alkyl group, or both of R⁸ bind to form a lower alkylene group;
Q¹ represents a lower alkyl group which may have a substituent selected from the following group (D);
(D) —OR^H, —COOR^I, —CONR^J R^K, a 6 to 10-membered aryl group which may have one to three substituents selected from the following group (iii), and a 5 to 10-membered aromatic heterocyclic group which may have one to three substituents selected from the following group (iv);
wherein R^H, R^I, R^J and R^K, or —NR^J R^K have the same meanings as defined above;
(iii) a halogen atom, a nitro group, a lower alkyl group, —OR^L in which R^L has the same meaning as defined above, and —COOR^M in which R^M has the same meaning as defined above;
(iv) a halogen atom, an oxo group, a lower alkyl group and a phenyl group; and
T¹ represents an oxygen atom or a sulfur atom;
X³ represents a chlorine atom, a bromine atom or an iodine atom;
X⁴ represents a chlorine atom, a bromine atom or an iodine atom; and
Q, R¹, R² and T have the same meanings as defined above.

Process A

A benzenesulfonamide derivative represented by the above general formula (X) can be prepared by condensing a benzene-sulfonyl halide derivative represented by the above general formula (VIII) with a phenethylamine derivative represented by the above general formula (IX) or a salt thereof in the presence or absence of a base such as triethylamine or potassium carbonate in a polar solvent such as tetrahydrofuran, N,N-dimethyl-formamide, or a mixed solvent of such solvent with water at usually 0° C. to room temperature.

Process B

A benzenesulfonamide derivative represented by the above general formula (XII) can be prepared by condensing a benzene-sulfonamide derivative wherein R⁶ is a hydroxy group represented by the above general formula (X) with a trifluoromethanesulfonic anhydride represented by the above general formula (XI) in the presence of a base such as N,N-dimethylaminopyridine in a solvent such as dichloromethane, tetrahydrofuran at usually 0° C. to reflux temperature.

Process C

A benzenesulfonamide derivative represented by the above general formula (XIV) can be prepared by condensing a benzene-sulfonamide derivative represented by the above general formula (XII) or a benzenesulfonamide derivative wherein $R^6$ is a halogen atom represented by the above general formula (X) with a boron compound represented by the above general formula (XIII) in the presence of a catalyst such as tetrakis(triphenylphosphine)palladium(0), palladium(II) acetate or [1,1'-bis(diphenylphosphino)ferrocene]chloronickel(II) and a base such as sodium carbonate, sodium hydrogen carbonate, potassium phosphate or triethylamine and in the presence or absence of a phase-transfer catalyst such as tetrabutylammonium bromide in a solvent such as toluene, tatrahydrofuran, N,N-dimethyl-formamide or water, or a mixed solvent thereof at usually room temperature to reflux temperature.

Process D

A compound wherein $R^7$ is a (lower alkyl)thioaryl group and/or T is a sulfur atom of a compound represented by the above general formula (XIV) can be converted into a corresponding sulfonyl compound by treating it with an oxidizing agent such as oxone (trademark) or m-chloroperbenzoic acid in a solvent such as acetone or dichloromethane, or a mixed solvent of such solvent with water at usually 0° C. to reflux temperature.

Process E

A compound of the above general formula (X) or (XIV), or a compound wherein $T^1$ is an oxygen atom and $R^5$ is a benzyl group of a compound wherein $R^7$ is a (lower alkyl)thioaryl group oxidizing the sulfur atom represented by the above general formula (XIV) can be converted into a corresponding phenol compound represented by the above general formula (XV) by subjecting it to catalytic hydrogenation using a palladium catalyst such as palladium-carbon or palladium hydroxide in a hydrogen atmosphere in a polar solvent such as ethanol at usually room temperature to reflux temperature and at atmospheric pressure or applied pressure to remove the benzyl group. This process can be similarly carried out using a compound wherein $T^1$ or T is an oxygen atom and $R^1$ is a benzyl group after the following Process F or G.

Process F

A corresponding N-alkylated compound can be prepared by subjecting a compound represented by the above general formula (XV) to N-alkylation using an alkylating agent represented by the above general formula (XVI) in the presence of a base such as triethylamine or potassium carbonate in a solvent such as N,N-dimethylformamide at usually −20° C. to reflux temperature.

Process G

A benzenesulfonamide derivative represented by the above general formula (II) can be prepared by subjecting a compound of the above general formula (XV) or a compound N-alkylated by Process F to demethylation under heating in the presence of lithium chloride in a solvent such as N,N-dimethylformamide or N,N-dimethylacetamide at usually 100° C. to reflux temperature.

For example, of a compound represented by the above general formula (XV) in the aforementioned production process, a compound wherein $R^1$ has an amide group represented by the following general formula (XVb) can be also prepared by the following method:

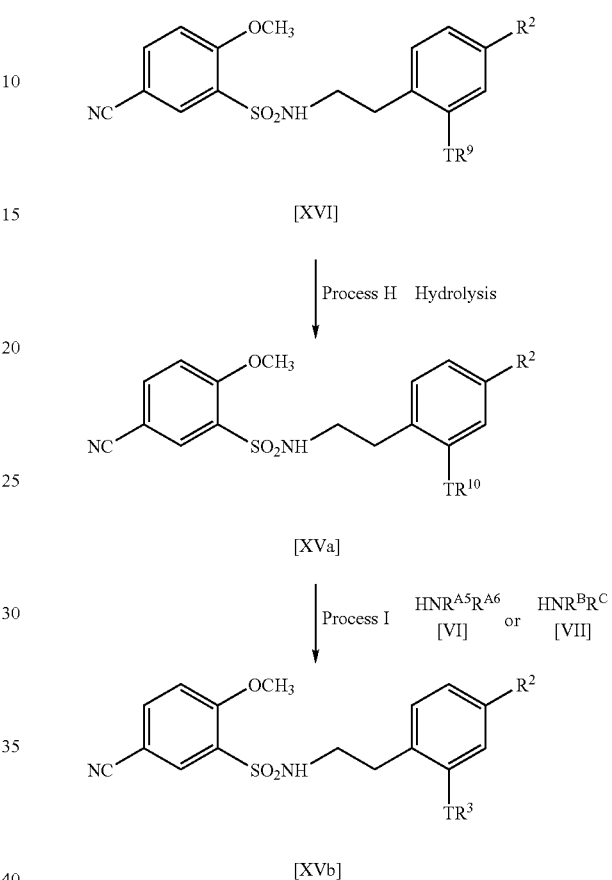

wherein $R^9$ represents a lower alkyl group having a substituent selected from the following group (F);

(F) —COOR$^{A9}$ or —CONR$^{B4}$R$^{C4}$;
   wherein R represents a lower alkyl group;
   $R^{B4}$ and $R^{C4}$ independently represent a hydrogen atom or a lower alkyl group having —COOR$^{B5}$ in which $R^{B5}$ is a lower alkyl group, with the proviso that both are not a hydrogen atom;

$R^{10}$ represents a lower alkyl group having a substituent selected from the following group (G);

(G) —COOH or —CONR$^{B6}$R$^{C6}$;
   wherein $R^{B6}$ and $R^{C6}$ independently represent a hydrogen atom or a lower alkyl group having —COOH, with the proviso that both are not a hydrogen atom; and $R^2$, $R^3$, $R^{A5}$, $R^{A6}$, $R^B$ and $R^C$, —NR$^B$R$^C$ and T have the same meanings as defined above.

Process H

A compound represented by the above general formula (XVI) can be hydrolyzed into a corresponding carboxylic acid compound represented by the above general formula (XVa) by treating it with an acid such as hydrochloric acid or sulfuric acid at room temperature to ref lux temperature, or with a base such as sodium hydroxide in water and a solvent such as acetonitrile, tetrahydrofuran or alcohols at usually 0° C. to reflux temperature.

Process I

A compound represented by the above general formula (XVa) can be converted into a corresponding amide compound represented by the above general formula (XVb) by allowing it to react with an amine compound represented by the above general formula (VI) or a salt thereof, or an amine compound represented by the above general formula (VII) or a salt thereof in the presence of a condensing agent such as 1-(3-dimethylaminoproyl)-3-ethyl-carbodiimide hydrochloride or diphenylphoshoryl azide and in the presence or absence of an agent for making an activated ester such as 1-hydroxybenzotriazole monohydrate and a base such as triethylamine in a solvent such as dichloromethane or N,N-dimethylformamide at usually 0° C. to room temperature.

In the aforementioned production process, for example, a compound represented by the above general formula (XIV) can be also prepared by the following method:

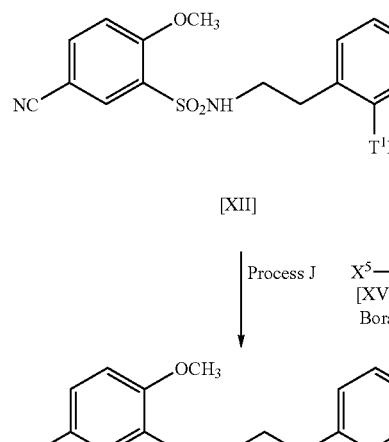

[XII]

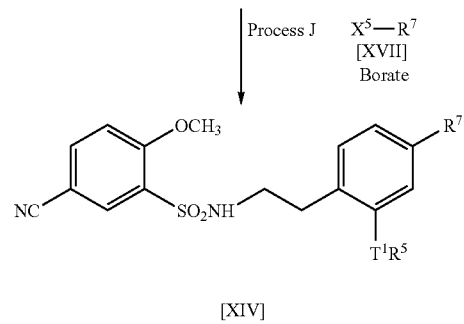

[XIV]

wherein $X^5$ represents a bromine atom, a chlorine atom or an iodine atom; and
$R^5$, $R^7$ and $T^1$ have the same meanings as defined above.

Process J

A benzenesulfonamide derivative represented by the above general formula (XIV) can be prepared by condensing a benzenesulfonamide derivative represented by the above general formula (XII) with a halide compound represented by the above general formula (XVII) in the presence of a borate such as bis(pinacolato)diboron and a catalyst such as [1,1'-bis-(diphenylphosphino)ferrocene]palladium(II) dichloride dichloromethane complex a in a solvent such as dioxane at usually room temperature to reflux temperature.

For example, the compound represented by the above general formula (XV) in the aforementioned production process can be also prepared using a compound represented by the following general formula (XVIII) obtained by a similar reaction according to the above Processes A, B, C and J from a corresponding compound wherein $R^5$ is a methoxymethyl group represented by the above general formula (IX) as a starting material by the following method:

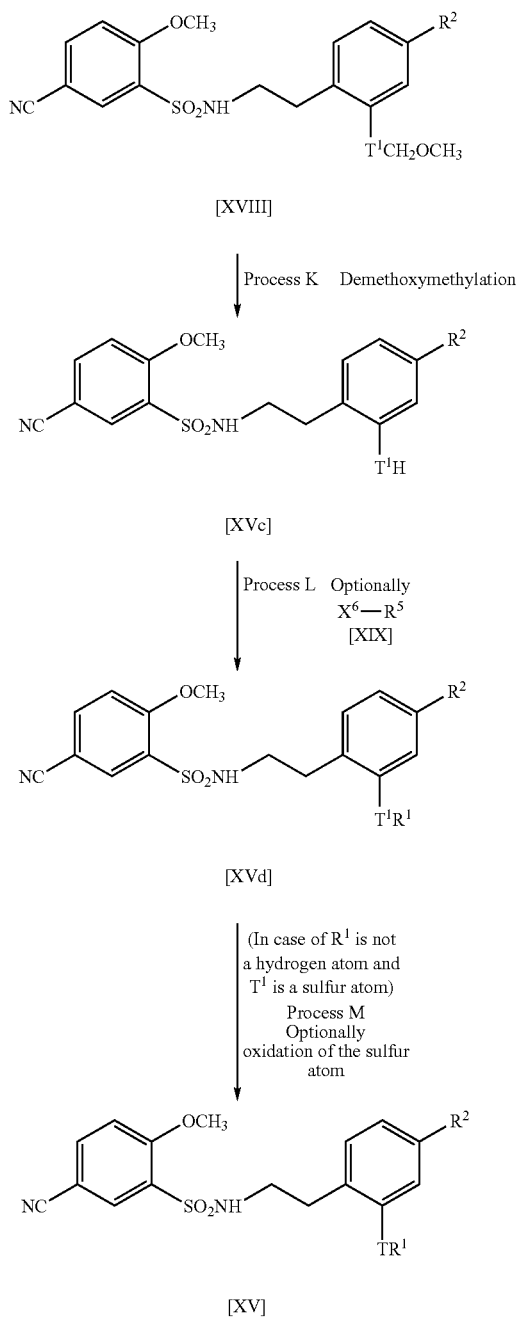

wherein $X^6$ represents a bromine atom, a chlorine atom or an iodine atom; and
$R^1$, $R^2$, $R^5$, T and $T^1$ have the same meanings as defined above.

Process K

A compound represented by the above general formula (XVIII) can be converted into a phenol compound or a thiophenol compound represented by the above general formula (XVc) by treating it in the presence of an acid such as hydrochloric acid or sulfuric acid in a solvent such as tetrahydrofuran or isopropanol, or a mixed solvent thereof at usually 0° C. to reflux temperature.

Process L

A corresponding O- or S-alkylated compound represented by the above general formula (XVd) can be prepared by condensing a compound represented by the above general formula (XVc) with a halide compound represented by the above general formula (XIX) in the presence of a base such as N,N-diisopropylethylamine, triethylamine or potassium carbonate a in a solvent such as N,N-dimethylformamide, tetrahydrofuran or ethanol at usually −20° C. to reflux temperature.

Process M

A compound wherein $T^1$ is a sulfur atom and $R^1$ is not a hydrogen atom of a compound represented by the above general formula (XVd) can be converted into a corresponding sulfonyl compound by treating it with an oxidizing agent such as oxone (trademark) or m-chloroperbenzoic acid in a solvent such as acetone or dichloromethane, or a mixed solvent of such solvent with water at usually 0° C. to reflux temperature.

For example, the compound represented by the above general formula (V) in the aforementioned production process is commercially available or can be prepared by methods described in literature or the like (Michael Folkmann, Synthesis, 1159 (1990); Jose Alxander, J. Med. Chem., 318–322, 31 (1988)).

The compounds of the present invention obtained by the above production process can be easily isolated and purified by conventional separation means such as fractional recrystallization, precipitation, purification using column chromatography, solvent extraction and the like.

The 5-amidino-2-hydroxybenzenesulfonamide derivatives represented by the above general formula (I) of the present invention can be converted into their pharmaceutically acceptable salts in the usual way. Examples of the such salts include acid addition salts with mineral acids (e.g., hydrochloric acid, hydrobromic acid, hydroiodic acid, sulfuric acid, nitric acid, phosphoric acid and the like), acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like), salts with organic amines (e.g., morpholine, pyrrolidine, piperidine, piperazine, lysine and the like), and salts with inorganic bases such as a sodium salt, a potassium salt and a calcium salt.

In addition, the compounds represented by the above general formula (I) of the present invention also include its hydrates and solvates with pharmaceutically acceptable solvents (e.g., ethanol).

Of the compounds represented by the above general formula (I) of the present invention, compounds having an asymmetric carbon atom exist in two optical isomer forms of (R) configuration and (S) configuration. Either one of the isomers or a mixture thereof can be employed in the present invention. In the compounds represented by the above general formula (I) of the present invention, when geometrical isomers or tautomers exist, the present invention includes all of the geometrical isomers and tautomers.

The compounds represented by the above general formula (I) of the present invention are compounds having a potent inhibitory activity on activated blood coagulation factor X and anti-coagulation activity. The compounds represented by the above general formula (I) of the present invention also have an extremely weak inhibitory activity on thrombin and therefore are highly selective activated blood coagulation factor X inhibitors.

Furthermore, in the compounds represented by the above general formula (I) of the present invention, the substituent $R^1$ is preferably a lower alkyl group having —COOR$^4$ wherein $R^4$ has the same meaning as defined above, and more preferably a methyl group having —COOR$^{410}$ wherein $R^{410}$ is a 3 to 10-membered cycloalkyl group or a lower alkyl group. The substituent $R^2$ is preferably a phenyl group having a substituent selected from the above group (B), and the substituent is preferably at the p-position. Furthermore, the substituent $R^2$ is more preferably a phenyl group having a substituent selected from the group consisting of a sulfamoyl group, a lower alkylsulfonyl group and a mono(lower alkyl)sulfamoyl group, and most preferably a phenyl group having a lower alkylsulfonyl group. The substituent Q is preferably a hydrogen atom. The substituent T is preferably an oxygen atom. The substituent Z is preferably a hydroxy group or —COOR$^N$ wherein $R^N$ has the same meaning as defined above, and more preferably a hydroxy group. Compounds having such the substituent Z and pharmaceutically acceptable salts thereof are excellent compounds which can exert a favorable activated blood coagulation factor X inhibitory activity when they are orally administered. As the compounds represented by the above general formula (I) of the present invention, ethyl [4-[2-[2-hydroxy-5-(N-hydroxycarbamimidoyl)benzenesulfonyl-amino]ethyl]-2'-mthanesulfonylbiphenyl-3-yloxy]acetate, isopropyl [4-[2-[2-hydroxy-5-(N-hydroxycarbamimidoyl)-benzenesulfonylamino]ethyl]-2'-methanesulfonylbiphenyl-3-yloxy]acetate, n-butyl[4-[2-[2-hydroxy-5-(N-hydroxycarbamimidoyl)benzenesulfonylamino]ethyl]-2'-methanesulfonylbiphenyl-3-yloxy]acetate and cyclohexyl [4-[2-[2-hydroxy-5-(N-hydroxycarbamimidoyl)benzenesulfonylamino]-ethyl]-2'-methanesulfonylbiphenyl-3-yloxy]acetate are preferable, and isopropyl[4-[2-[2-hydroxy-5-(N-hydroxy-carbamimidoyl)benzenesulfonylamino]ethyl]-2'-methane-sulfonylbiphenyl-3-yloxy]acetate, n-butyl[4-[2-[2-hydroxy-5-(N-hydroxycarbamimidoyl)benzenesulfonylamino]ethyl]-2'-methanesulfonylbiphenyl-3-yloxy]acetate and cyclohexyl [4-[2-[2-hydroxy-5-(N-hydroxycarbamimidoyl)benzene-sulfonyl-amino]ethyl]-2'-methanesulfonylbiphenyl-3-yloxy]acetate are more preferable.

The compounds represented by the above general formula (I) of the present invention are selective activated blood coagulation factor X inhibitors. In consequence, the compounds of the present invention are extremely useful as agents for the prevention or treatment of cerebral infarction, cerebral thrombosis, cerebral embolism, transient cerebral ischemic attack (TIA), subarachnoid hemorrhage-induced cerebral vasospasm, alzheimer's disease, myocardial infarction, unstable angina, heart failure, atrial fibrillary thrombosis, pulmonary thrombosis, pulmonary embolism, acute respiratory distress syndrome, Berger disease, peripheral arterial obstruction, deep venous thrombosis, disseminated intravascular coagulation syndrome, atherosclerosis, behcet's disease, diabetic neuropathy, diabetic retinopathy, diabetic thrombotic complications, interplanting rejection, systemic inflammatory response syndrome (SIRS), dialysis- or operation-induced thrombocytopenia, thrombus formation after artificial blood vessel operation or after artificial valve replacement, restenosis and reocculusion after coronary intervention such as percutaneous transluminal coronary angioplasty (PTCA) or percutaneous transluminal coronary recanalization (PTCR) surgery, thrombus formation at the time of extracorporeal circulation and the like, agents for the prevention of blood coagulation at the time of insertion of blood vessel catheter, and agents for the prevention or treatment of influenza virus infection based on the activity to inhibit growth of influenza virus.

When the 5-amidino-2-hydroxybenzenesulfonamide derivatives represented by the above general formula (I) of the present invention and pharmaceutically acceptable salts thereof are employed in the practical treatment, they are administered orally or parenterally in the form of appropriate pharmaceutical compositions such as tablets, powders, fine granules, granules, capsules, injections, solutions, adhesive preparations, ointments, inhalants, suppositories and the like. These pharmaceutical compositions can be formulated in accordance with pharmaceutically conventional methods using conventional pharmaceutical carriers, excipients and other additives.

The dosage is appropriately decided depending on the sex, age, body weight, degree of symptoms and the like of each patient to be treated, which is approximately within the range of from 1 to 5,000mg per day per adult human in case of oral administration and approximately within the range of from 0.01 to 500 mg per day per adult human in case of parenteral administration such as injection, and the daily dose can be divided into one to several doses per day.

EXAMPLES

The present invention is further illustrated in more detail by way of the following Reference Examples, Examples and Test Examples. However, the present invention is not limited thereto.

Reference Example 1

7-Hydroxycroman-2-one

A mixture of 100 g of 7-hydroxycromen-2-one, 10 g of 10% palladium on carbon, 500 mL of tetrahydrofuran and 800 mL of ethanol was stirred under a hydrogen atmosphere at 65° C. for 15 hours. To the reaction mixture were added a suspension of 10 g of 10% palladium on carbon in 200 mL of ethanol under ice-cooling, and the mixture was stirred under a hydrogen atmosphere at 65° C. for 15 hours. The reaction mixture was filtered through a diatomaceous earth, and the filtrate was concentrated under reduced pressure to give 106.5 g of colorless 7-hydroxy-croman-2-one.
$^1$H-NMR (CDCl$_3$) δ ppm: 2.75–2.96 (4H, m), 5.81 (1H, br s), 6.59–6.66 (2H, m), 7.04 (1H, d, J=7.9 Hz)

Reference Example 2

7-Benzyloxycroman-2-one

To a stirred suspension of 202.4 g of 7-hydroxy-croman-2-one and 341.0 g of potassium carbonate in N,N-dimethylformamide was added 153.2 mL of benzyl chloride at room temperature, and the mixture was stirred at room temperature for 15 hours. After the reaction mixture was concentrated under reduced pressure to remove the solvent, the residue was added to a mixture of ethyl acetate and water. The organic layer was separated, washed with water, dried over anhydrous magnesium sulfate, and filtered. The filtrate was concentrated under reduced pressure, and the residue was triturated in diisopropyl ether-hexane. The solid was collected by filtration to give 266.1 g of 7-benzyloxy-cromae-2-one as a pale brown solid.
$^1$H-NMR (CDCl$_3$) δ ppm: 2.73–2.81 (2H, m), 2.90–2.98 (2H, m), 5.05 (2H, s), 6.68 (1H, d, J=2.5 Hz), 6.73 (1H, dd, J=8.3, 2.5 Hz), 7.08 (1H, d, J=8.3 Hz), 7.30–7.46 (5H, m)

Reference Example 3

3-(4-Benzyloxy-2-hydroxyphenyl)propionamide

To a solution of 33.26 g of 7-benzyloxycroman-2-one in 264 mL of tetrahydrofuran was added 82 mL of 28% aqueous ammonia solution at room temperature. After the mixture was stirred at room temperature for 20 minutes, to the reaction mixture was added 654 mL of 1 mol/L hydrochloric acid in an ice-bath. The resulted suspension was diluted with about 1 L of water, and the precipitate was collected by filtration to give 34.8 g of 3-(4-benzyloxy-2-hydroxyphenyl)propionamide as a colorless powder.
$^1$H-NMR (CDCl$_3$) δ ppm: 2.60–2.70 (2H, m), 2.80–2.90 (2H, m), 5.01 (2H, s), 5.46 (2H, br s), 6.49 (1H, dd, J=8.5, 2.5 Hz), 6.58 (1H, d, J=2.5 Hz), 6.93 (1H, d, J=8.5 Hz), 7.28–7.45 (5H, m), 8.67 (1H, s)

Reference Example 4

3-(4-Benzyloxy-2-methoxymethoxyphenyl)propionamide

To a stirred suspension of 5.64 g of 60% sodium hydride in oil in 628 mL of N,N-dimethylformamide was added 34.8 g of 3-(4-benzyloxy-2-hydroxyphenyl)propionamide under ice-cooling, and the mixture was stirred at 50° C. for 40 minutes. To the reaction mixture was added 12.39 g of chloromethyl methyl ether under ice-cooling, and the mixture was stirred at room temperature for 15 hours. After the reaction mixture was concentrated under reduced pressure to remove the solvent, the residue was poured into a mixture of 500 mL of ethyl acetate, 100 mL of toluene, and 200 mL of water. The organic layer was separated, washed with water, dried over anhydrous magnesium sulfate, and filtered. The filtrate was concentrated under reduced pressure to give a colorless solid. The solid was triturated in ethyl acetate-diisopropyl ether to collect by filtration of 35.3 g of 3-(4-benzyloxy-2-methoxymethoxy-phenyl)propionamide as a colorless solid.
$^1$H-NMR (CDCl$_3$) δ ppm: 2.50 (2H, t, J=7.6 Hz), 2.91 (2H, t, J=7.6 Hz), 3.47 (3H, s), 5.02 (2H, s), 5.18 (2H, s), 5.25–5.45 (2H, m), 6.56 (1H, dd, J=8.5, 2.5 Hz), 6.77 (1H, d, J=2.5 Hz), 7.07 (1H, d, J=8.5 Hz), 7.30–7.45 (5H, m)

Reference Example 5

2-(4-Benzyloxy-2-methoxymethoxyphenyl)ethylamine

To a solution of 28.42 g of 3-(4-benzyloxy-2-methoxymethoxyphenyl)propionamide and 40.4 mL of 1,8-diazabicyclo-[5.4.0]-7-undecene in 895 mL of methanol was added 16.04 g of N-bromosuccinimide at 65° C. After the mixture was stirred at 65° C. for 15 minutes, to the reaction mixture was added additional 16.04 g of N-bromosuccinimide at 65° C. After being stirred at 65° C. for 15 minutes, the resulted mixture was concentrated under reduced pressure to remove the solvent. To the residue were added water and ethyl acetate, and the organic layer was separated. The organic layer was washed with water, dried over anhydrous magnesium sulfate, and filtered. The filtrate was concentrated under reduced pressure to give oily product. To a solution of this residue in 242 mL of ethanol was added 67.6 mL of 8 mol/L aqueous potassium hydroxide solution, and the mixture was refluxed for 15 hours. The reaction mixture was concentrated under reduced pressure to remove the solvent. To the residue were added 500 mL of ethyl acetate, 50 mL of toluene, and 300 mL of water, and the organic layer was separated. The organic layer was washed with water, dried over anhydrous magnesium sulfate, and filtered. The filtrate was concentrated under reduced pressure, and the residue was purified by medium pressure liquid column chromatography on silica gel (eluent: hexane-ethyl acetate) to give 80.0 g of 2-(4-benzyloxy-2-methoxymethoxy-phenyl)ethylamine as a colorless oil.

$^1$H-NMR (CDCl$_3$) δ ppm: 1.31 (2H, br s), 2.71 (2H, t, J=6.9 Hz), 2.90 (2H, t, J=6.9 Hz), 3.47 (3H, s), 5.03 (2H, s), 5.17 (2H, s), 6.56 (1H, dd, J=8.2, 2.5 Hz), 6.79 (1H, d, J=2.5 Hz), 7.04 (1H, d, J=8.2 Hz), 7.29–7.45 (5H, m)

Reference Example 6

4-(2-Aminoethyl)-3-methoxymethoxyphenol

A mixture of 18.00 g of 2-(4-benzyloxy-2-methoxy-methoxyphenyl)ethylamine, 3.6 g of 10% palladium on carbon (Degussa Inc. :E101 NE/W) and 230 mL of ethanol was stirred under a hydrogen atmosphere at room temperature for 1 hour. After the catalyst was filtered off through a diatomaceous earth, the filtrate was concentrated under reduced pressure to give 12.65 g of 4-(2-aminoethyl)-3-methoxymethoxyphenol as a colorless solid.

$^1$H-NMR (CD$_3$OD) δ ppm: 2.65–2.75 (2H, m), 2.75–2.85 (2H, m), 3.45 (3H, s), 5.16 (2H, s), 6.36 (1H, dd, J=8.1, 2.3 Hz), 6.58 (1H, d, J=2.3 Hz), 6.94 (1H, d, J=8.1 Hz)

Reference Example 7

N-Cyanomethyl-2,2,2-trifluoroacetamide

Aminoacetonitrile hydrogen sulfate (50 g) and 77 mL of pyridine were suspended in 300 mL of dichloromethane, and 80 mL of trifluoroacetic anhydride was added to the stirred mixture under ice-cooling. After the mixture was stirred at room temperature for 29 hours, the insoluble material was removed by filtration, and washed with ethyl acetate. After the filtrate was concentrated under reduced pressure, to the residue was added water. The mixture was extracted with ethyl acetate, and the organic layer was washed with diluted hydrochloric acid and water. After the extract was dried over anhydrous magnesium sulfate, the solvent was removed under reduced pressure to give 66 g of N-cyanomethyl-.2,2,2-trifluoroacetamide.

$^1$H-NMR (CDCl$_3$) δ ppm: 4.31 (2H, d, J=6.6 Hz), 7.10 (1H, br s)

Reference Example 8

2,2,2-Trifluoro-N-[2-(2-hydroxy-4-isopropylphenyl)-2-oxoethyl]acetamide

To 250 mL of 1.0 mol/L boron trichloride dichloromethane solution were added a solution of 28.5 mL of 3-isopropylphenol in 130 mL of dichloromethane, 38 g of N-cyanomethyl-2,2,2-trifluoroacetamide and 14.2 g of aluminum chloride under an argon atmosphere in an ice-bath with stirring. After the mixture was stirred at room temperature for 16 hours, ice and 2 mol/L hydrochloric acid were added to the reaction mixture under ice-cooling. After the mixture was stirred at room temperature for 40 minutes, the organic layer was separated, and the aqueous layer was extracted with dichloromethane. The organic layers were combined, washed with brine, and dried over anhydrous magnesium sulfate. The solvent was removed under reduced pressure, and 100 mL of hexane was added to the residue. The generated crystal was collected by filtration, washed with hexane and dried under reduced pressure to give 22.9 g of 2,2,2-trifluoro-N-[2-(2-hydroxy-4-isopropylphenyl)-2-oxoethyl]-acetamide.

$^1$H-NMR (CDCl$_3$) δ ppm: 1.26 (6H, d, J=8.8 Hz), 2.86–2.98 (1H, m), 4.83 (2H, d, J=4.1 Hz), 6.85 (1H, dd, J=8.2, 1.6 Hz), 6.90 (1H, d, J=1.6 Hz), 7.42 (1H, br s), 7.59 (1H, d, J=8.2 Hz), 11.42 (1H, br s)

Reference Example 9

Ethyl[5-isopropyl-2-[2-(2,2,2-trifluoroacetylamino) ethyl]-phenoxy]acetate

To a solution of 500 mg of 2,2,2-trifluoro-N-[2-(2-hydroxy-4-isopropylphenyl)-2-oxoethyl]acetamide in 2.63 mL of trifluoroacetic acid was added 0.94 mL of triethylsilane. After being stirred at room temperature for 13 hours, the reaction mixture was concentrated and dried thoroughly. The obtained residue and 382 mg of potassium carbonate were suspended in 10 mL of N,N-dimethylformamide, and 0.288 mL of ethyl bromoacetate was added to the stirred mixture under ice-cooling. The mixture was stirred at room temperature for 15 hours, and to the reaction mixture was added water. After the mixture was extracted with ethyl acetate, the organic layer was washed successively with water and brine, and dried over anhydrous magnesium sulfate. The solvent was removed under reduced pressure, and the obtained residue was purified by column chromatography on silica gel (eluent: ethyl acetate-hexane) to give 535 mg of ethyl [5-isopropyl-2-[2-(2,2,2-trifluoroacetylamino)ethyl]-phenoxy]acetate.

$^1$H-NMR (DMSO-d$_6$) δ ppm: 1.10–1.30 (9H, m), 2.75–2.95 (3H, m), 3.35–3.50 (2H, m), 4.17 (2H, q, J=7.3 Hz), 4.81 (2H, s), 6.70–6.90 (2H, m), 7.03 (1H, d, J=7.5 Hz), 9.40–9.55 (1H, m)

Reference Example 10

The following compound was prepared according to a similar manner to that described in Reference Example 9.

Ethyl 2-[5-isopropyl-2-[2-(2,2,2-trifluoroacetylamino)-ethyl]phenoxy]propionate $^1$H-NMR (CDCl$_3$) δ ppm: 1.18–1.22 (6H, m), 1.25 (3H, t, J=6.9 Hz), 1.64 (3H, d, J=6.6 Hz), 2.79–2.93 (2H, m), 2.95–3.02 (1H, m), 3.55–3.64 (1H, m), 3.68–3.76 (1H, m), 4.21 (2H, q, J=6.9 Hz), 4.88 (1H, q, J=6.6 Hz), 6.59–6.61 (1H, m), 6.79–6.83(1H, m), 7.05 (1H, d, J=7.3 Hz), 7.16 (1H, br s)

Reference Example 11

Ethyl[2-(2-aminoethyl)-5-isopropylphenoxy]acetate hydrochloride

To a solution of 26.4 g of ethyl[5-isopropyl-2-[2-(2,2,2-trifluoroacetylamino)ethyl]phenoxy]acetate in a mixture of 300 mL of methanol and 15 mL of water was added 30.3 g of potassium carbonate. After the mixture was stirred at room temperature for 20 hours, the insoluble material was removed by filtration, and the filtrate was concentrated under reduced pressure. To the residue was added 300 mL of 35% hydrogen chloride ethanol solution, and the mixture was stirred at room temperature for 3 hours. The reaction mixture was concentrated under reduced pressure to give a crude product of 24.8 g of ethyl [2-(2-aminoethyl)-5-isopropylphenoxy]acetate hydrochloride.

$^1$H-NMR (DMSO-$d_6$) δ ppm: 1.17 (6H, d, J=6.9 Hz), 1.21 (3H, t, J=7.3 Hz), 2.75–2.95 (3H, m), 2.95–3.05 (2H, m), 4.18 (2H, q, J=7.3 Hz), 4.84 (2H, s), 6.75–6.79 (1H, m), 6.81 (1H, dd, J=7.9, 1.6 Hz), 7.10 (1H, d, J=7.9 Hz), 8.13 (3H, br s)

Reference Example 12

The following compound was prepared according to a similar manner to that described in Reference Example 11.

Ethyl 2-[2-(2-aminoethyl)-5-isopropylphenoxy]propionate hydrochloride $^1$H-NMR (CDCl$_3$) δ ppm: 1.12–1.19 (9H, m), 1.54 (3H, d, J=6.5 Hz), 2.75–3.11 (5H, m), 4.09–4.18 (2H, m), 5.06 (1H, q, J=6.5 Hz), 6.71 (1H, s), 6.78–6.82 (1H, m), 7.09 (1H, d, J=8.0 Hz), 7.93 (3H, br s)

Reference Example 13

2-Hydroxy-4-isopropylbenzaldehyde

To 100 mL of trifluoroacetic acid were added 25.39 g of 3-isopropylphenol and 26.14 g of hexamethylenetetramine. After being stirred at 60° C. for an hour, the reaction mixture was concentrated under reduced pressure. To the residue was added diluted hydrochloric acid, and the mixture was stirred at room temperature for 30 minutes. After the reaction mixture was extracted with ethyl acetate, the organic layer was washed with saturated aqueous sodium bicarbonate solution, and brine, and dried over anhydrous magnesium sulfate. The solvent was removed under reduced pressure, and the residue was purified by column chromatography on silica gel (eluent: ethyl acetate-hexane) to give 6.69 g of 2-hydroxy-4-isopropylbenzaldehyde.

$^1$H-NMR (CDCl$_3$) δ ppm: 1.26 (6H, d, J=6.9 Hz), 2.92 (1H, sept, J=6.9 Hz), 6.83–6.87 (1H, m), 6.88 (1H, dd, J=7.9, 1.6 Hz), 7.47 (1H, d, J=7.9 Hz), 9.83 (1H, s), 11.03 (1H, br s)

Reference Example 14

2-Benzyloxy-4-isopropylbenzaldehyde

2-Hydroxy-4-isopropylbenzaldehyde (6.69 g) and 11.26 g of potassium carbonate were suspended with 100 mL of N,N-dimethylformamide, and 5.33 mL of benzyl bromide was added to the stirred mixture at room temperature. After the mixture was stirred at room temperature for 16 hours, the insoluble material was removed by filtration. To the filtrate were added 10 mL of water and 10 mL of diluted hydrochloric acid, and the mixture was extracted with ethyl acetate. After being washed with brine, the organic layer was dried over anhydrous magnesium sulfate. The solvent was removed under reduced pressure, and the obtained residue was purified by column chromatography on silica gel (eluent: ethyl acetate-hexane) to give 10.44 g of 2-benzyloxy-4-isopropylbenzaldehyde.

$^1$H-NMR (CDCl$_3$) δ ppm: 1.25 (6H, d, J=6.9 Hz), 2.88–2.97 (1H, m), 5.19 (2H, s), 6.90 (1H, s), 6.92 (1H, d, J=7.9 Hz), 7.32–7.47 (5H, m), 7.79 (1H, d, J=7.9 Hz), 10.49 (1H, s)

Reference Example 15

2-Benzyloxy-4-isopropyl-1-(2-nitrovinyl)benzene

To 100 mL of nitromethane were added 10.44 g of 2-benzyloxy-4-isopropylbenzaldehyde and 4.71 g of ammonium acetate. After being stirred at external 100° C. for 3 hours, the reaction mixture was concentrated under reduced pressure. The obtained residue was dissolved in ethyl acetate, and the organic layer was washed successively with 1 mol/L hydrochloric acid, and saturated aqueous sodium bicarbonate solution, and dried over anhydrous magnesium sulfate. The solvent was removed under reduced pressure to give 9.45 g of 2-benzyloxy-4-isopropyl-1-(2-nitrovinyl)benzene.

$^1$H-NMR (CDCl$_3$) δ ppm: 1.24 (6H, d, J=7.3 Hz), 2.87–2.95 (1H, m), 5.21 (2H, s), 6.86–6.93 (2H, m), 7.33–7.48 (6H, m), 7.82 (1H, d, J=13.2 Hz), 8.15 (1H, d, J=13.2 Hz)

Reference Example 16

2-(2-Benzyloxy-4-isopropylphenyl)ethylamine

To a stirred suspension of 3.01 g of lithium aluminum hydride in 100 mL of anhydrous diethyl ether was added dropwise a solution of 9.45 g of 2-benzyloxy-4-isopropyl-1-(2-nitro-vinyl)benzene in 10 mL of diethyl ether under ice-cooling with stirring during 10 minutes. After the mixture was stirred for 1 hour, 63.5 mL of 2 mol/L sodium hydroxide solution was added dropwise to the stirred reaction mixture under ice-cooling, and the mixture was stirred for 1 hour. To the mixture was added anhydrous sodium sulfate, and the mixture was stirred for 15 minutes. The insoluble material was filtered off through a diatomaceous earth, and 100 mL of water was added to the filtrate. The mixture was extracted with ethyl acetate, and the organic layer was washed successively with saturated aqueous sodium bicarbonate solution, and brine, and dried over anhydrous magnesium sulfate. The solvent was removed under reduced pressure to give 8.56 g of 2-(2-benzyloxy-4-isopropylphenyl)-ethylamine.

$^1$H-NMR (CDCl$_3$) δ ppm: 1.23 (6H, d, J=6.9 Hz), 2.80 (2H, t, J=6.9 Hz), 2.83–2.91 (1H, m), 2.96 (2H, t, J=6.9 Hz), 5.07 (2H, s), 6.76–6.80 (2H, m), 7.08 (1H, d, J=7.3 Hz), 7.29–7.47 (5H, m)

Reference Example 17 tert-Butyl N-[2-(2-benzyloxy-4-isopropylphenyl) ethyl]-carbamate

To 100 mL of tetrahydrofuran were added 8.56 g of 2-(2-benzyloxy-4-isopropylphenyl)ethylamine and 7.63 g of di-tert-butyl dicarbonate, and the mixture was stirred at room temperature for 12 hours. The solvent was removed under reduced pressure, and the obtained residue was purified by column chromatography on silica gel (eluent: ethyl acetate-hexane) to give 12.00 g of tert-butyl N-[2-(2-benzyloxy-4-isopropyl-phenyl)ethyl]carbamate.

$^1$H-NMR (CDCl$_3$) δ ppm: 1.23 (6H, d, J=6.9 Hz), 1.41 (9H, s), 2.76–2.91 (3H, m), 3.27–3.42 (2H, m), 4.69 (1H, br s), 5.08 (2H, s), 6.75–6.82 (2H, m), 7.07 (1H, d, J=7.9 Hz), 7.30–7.48 (5H, m)

Reference Example 18 tert-Butyl N-[2-(2-hydroxy-4-isopropylphenyl)ethyl]-carbamate tert-Butyl N-[2-(2-benzyloxy-4-isopropylphenyl)-ethyl] carbamate (12.00 g) was dissolved in 150 mL of ethanol. To the stirred solution was added 1.10 g of 10% palladium on carbon under ice-cooling, and the mixture was stirred under a hydrogen atmosphere and ordinary pressure at 30° C. for 16 hours. The insoluble material was filtered, and the filtrate was concentrated under reduced pressure to give 6.66 g of tert-butyl N-[2-(2-hydroxy-4-isopropylphenyl)ethyl]carbamate.

$^1$H-NMR (CDCl$_3$) δ ppm: 1.21 (6H, d, J=6.9 Hz),1.45 (9H, s), 2.75–2.86 (3H, m), 3.25–3.32 (2H, m), 4.92 (1H, br s), 6.65–6.71 (1H, m), 6.72–6.75 (1H, m), 6.96 (1H, d, J=7.9 Hz), 7.03 (1H, br s)

Reference Example 19

Ethyl 4-[2-(2-tert-butoxycarbonylaminoethyl)-5-isopropyl-phenoxy]butyrate tert-Butyl N-[2-(2-hydroxy-4-isopropylphenyl)ethyl]-carbamate (0.234 g) and 0.116 g of potassium carbonate were suspended in 5 mL of N,N-dimethylformamide. To the stirred suspension was added dropwise 0.126 mL of ethyl 4-bromobutyrate at room temperature, and the mixture was stirred at room temperature for 16 hours. To the reaction mixture were added 10 mL of 1 mol/L hydrochloric acid and then 20 mL of water, and the mixture was extracted with ethyl acetate. The organic layer was washed with brine, and dried over anhydrous magnesium sulfate. The solvent was removed under reduced pressure, and the obtained residue was purified by column chromatography on silica gel (eluent: ethyl acetate-hexane) to give 0.283 g of ethyl 4-[2-(2-tert-butoxycarbonylaminoethyl)-5-isopropylphenoxy]-butyrate.

$^1$H-NMR (CDCl$_3$) δ ppm: 1.24 (6H, d, J=7.3 Hz), 1.26 (3H, t, J=7.3 Hz), 1.42 (9H, s), 2.10–2.19 (2H, m), 2.53 (2H, t, J=7.3 Hz), 2.72–2.79 (2H, m), 2.81–2.89 (1H, m), 3.28–3.38 (2H, m), 4.02 (2H, t, J=6.0 Hz), 4.15 (2H, q, J=7.3 Hz), 4.75 (1H, br s), 6.68–6.71 (1H, m), 6.74–6.79 (1H, m), 7.04 (1H, d, J=7.6 Hz)

Reference Example 20

Ethyl 4-[2-(2-aminoethyl)-5-isopropylphenoxy]butyrate hydrochloride

4-[2-(2-tert-Butoxycarbonylaminoethyl)-5-isopropylphenoxy]butyrate (0.283 g) was deissolved in 10 mL of 35% hydrogen chloride ethanol solution, and the mixture was stirred at room temperature for 5 hours. The solvent was removed under reduced pressure to give 0.235 g of ethyl 4-[2-(2-aminoethyl)-5-isopropylphenoxy]butyrate hydrochloride.

$^1$H-NMR (DMSO-d$_6$) δ ppm: 1.18 (3H, t, J=6.9 Hz), 1.19 (6H, d, J=6.9 Hz), 1.94–2.04 (2H, m), 2.78–2.89 (3H, m), 2.90–2.99 (2H, m), 4.01 (2H, t, J=6.3 Hz), 4.08 (2H, q, J=6.9 Hz), 6.75–6.79 (1H, m), 6.81–6.85 (1H, m), 7.07 (1H, d, J=7.6 Hz), 7.93 (3H, br s)

Reference Example 21

2-(2-Benzyloxy-4-isopropylphenyl)ethylamine hydrochloride

To a solution of 0.300 g of tert-butyl N-[2-(2-benzyloxy-4-isopropylphenyl)ethyl]carbamate in 2 mL of ethanol was added 2 mL of 21% hydrogen chloride ethanol solution at room temperature. After being stirred at the same temperature for 2 hours, the reaction mixture was concentrated under reduced pressure to give 0.261 g of 2-(2-benzyloxy-4-isopropylphenyl)ethylamine hydrochloride.

$^1$H-NMR (CDCl$_3$) δ ppm: 1.20 (6H, d, J=6.9 Hz), 2.78–2.87 (1H, m), 3.04–3.12 (2H, m), 3.15–3.25 (2H, m), 5.10 (2H, s), 6.74 (1H, d, J=7.6 Hz), 6.78 (1H, s), 7.14 (1H, d, J=7.6 Hz), 7.33–7.48 (4H, m), 8.25 (3H, br s)

Reference Example 22

5-Carbamoyl-2-methoxybenzenesulfonyl chloride

To 1733 g of chlorosulfonic acid was added in small portions 150 g of 4-methoxybenzamide under ice-cooling with stirring during 15 minutes, and the mixture was stirred at room temperature for 14 hours. After being stirred at 50° C. for additional 1.5 hours, the reaction mixture was dropped into 7 kg of ice. The precipitate was collected by filtration, washed with water and hexane to give 230 g of 5-carbamoyl-2-methoxybenzenesulfonyl chloride.

$^1$H-NMR (DMSO-d$_6$) δ ppm: 3.81 (3H, s), 7.00 (1H, d, J=8.5 Hz), 7.10 (1H, br s), 7.84 (1H, dd, J=8.5, 2.5 Hz), 7.87 (1H, br s), 8.23 (1H, d, J=2.5 Hz)

Reference Example 23

5-Cyano-2-methoxybenzenesulfonyl chloride

5-Carbamoyl-2-methoxybenzenesulfonyl chloride (150 g) was suspended in 1800 mL of ethyl acetate. After 219 mL of thionyl chloride was dropped to the stirred suspension under ice-cooling, 2.3mL of N,N-dimethylformamide was added to the mixture. After being stirred at 55° C. for 3 hours, the reaction mixture was concentrated under reduced pressure. To the residue were added ethyl acetate and water, and the separated organic layer was washed with water, saturated aqueous sodium bicarbonate solution, and brine, and dried over anhydrous magnesium sulfate. The solvent was removed under reduced pressure, and the obtained crude product was recrystallized from ethyl acetate-hexane to give 86.8 g of 5-cyano-2-methoxybenzenesulfonyl chloride.

$^1$H-NMR (CDCl$_3$) δ ppm: 4.16 (3H, s), 7.24 (1H, d, J=8.8 Hz), 7.96 (1H, dd, J=8.8, 2.2 Hz), 8.28 (1H, d, J=2.2 Hz)

Reference Example 24

2-(Methylthio)phenylboronic acid

Magnesium (9.52 g) was suspended in 119 mL of tetrahydrofuran, and to the suspension were added 3.00 g of 2-bromothioanisole and about 20 mg of iodine. After the reaction was started by heating employing a dryer, 72 g of 2-bromothioanisole was dropped to the mixture during 20minutes. After being heated for 1 hour, the reaction mixture was diluted with 1000 mL of tetrahydrofuran, and cooled to 0° C. To the mixture was added 102 mL of triisopropyl borate at the same temperature, and the mixture was stirred at room temperature for 4 hours. To the reaction mixture was added water, and the solvent was removed under reduced pressure. The residue was added 500 mL of 2 mol/L hydrochloric acid, and the mixture was extracted with 300 mL of diethyl ether. The organic layer was extracted with 500 mL of 2 mol/L aqueous sodium hydroxide solution, and the aqueous layer was acidified by addition of concentrated hydrochloric acid under ice-cooling. The residual diethyl ether was removed under reduced pressure, and the precipitate was collected by filtration to give 45.95 g of 2-(methylthio)-phenylboronic acid.

$^1$H-NMR (DMSO-$d_6$) δ ppm: 2.50 (3H, s), 6.21–6.29 (2H, br s), 7.34 (1H, td, J=7.3, 1.3 Hz), 7.42 (1H, td, J=7.3, 1.3 Hz), 7.52 (1H, dd, J=7.3, 1.3 Hz), 8.01 (1H, dd, J=7.3, 1.3 Hz)

Reference Example 25

Hydroxylammonium acetate

To 100 mL of 50% aqueous hydroxylamine solution was added slowly 86.6 mL of acetic acid under ice-cooling with stirring, and the mixture was stirred at the same temperature for 40 minutes, then at room temperature for 40 minutes. After the reaction mixture was concentrated under reduced pressure, the residue was dissolved in 50 mL of ethanol, and the solution was concentrated under reduced pressure. To the residue was added toluene, and the mixture was concentrated under reduced pressure, and dried to give 76.4 g of hydroxylammonium acetate as a colorless solid.

$^1$H-NMR (DMSO-$d_6$) δ ppm: 1.88 (3H, s), 7.63 (4H, br s)

Reference Example 26

5-Cyano-N-[2-(4-hydroxy-2-methoxymethoxyphenyl)ethyl]-2-methoxybenzenesulfonamide 4-(2-Aminoethyl)-3-methoxymethoxyphenol (12.3 g) and 7.9 g of sodium bicarbonate were suspended in a mixture of 133 mL of tetrahydrofuran and 14.4 mL of water, to the suspension was added 18 mL portions of a solution of 14.50 g of 5-cyano-2-methoxybenzensulfonyl chloride in 180 mL of tetrahydrofuran every 10 minutes while the internal temperature was kept at 10–20° C. After being stirred at room temperature for 8 hours, the reaction mixture was purified by column chromatography on aminopropylated silica gel (eluent: ethyl acetate), and recrystallized from ethyl acetate-diisopropyl ether to give 21.87 g of 5-cyano-N-[2-(4-hydroxy-2-methoxymethoxyphenyl)-ethyl]-2-methoxybenzenesulfonamide as a colorless crystal.

$^1$H-NMR (CDCl$_3$) δ ppm: 2.74 (2H, t, J=6.3 Hz), 3.10–3.20 (2H, m), 3.40 (3H, s), 3.81 (3H, s), 4.85–4.95 (2H, m), 5.08 (2H, s), 6.38 (1H, dd, J=8.2, 2.2 Hz), 6.59 (1H, d, J=2.2 Hz), 6.87 (1H, d, J=8.2 Hz), 7.00 (1H, d, J=8.5 Hz), 7.78 (1H, dd, J=8.5, 2.2 Hz), 8.16 (1H, d, J=2.2 Hz)

Reference Example 27

Ethyl[2-[2-(5-cyano-2-methoxybenzenesulfonylamino)-ethyl]-5-isopropylphenoxy]acetate To a stirred solution of 326 mg of ethyl [2-(2-aminoethyl)-5-isopropylphenoxy]acetate hydrochloride and 0.452 mL of triethylamine in a mixture of 10 mL of tetrahydrofuran and 5 mL of water was added 238 mg of 5-cyano-2-methoxybenzene-sulfonyl chloride under ice-cooling, and the mixture was stirred at room temperature for 6 hours. To the reaction mixture was added 30 mL of water, and the mixture was extracted with 120 mL of ethyl acetate. The organic layer was washed with 100 mL of water, and 100 mL of brine, and dried over anhydrous magnesium sulfate. The solvent was removed under reduced pressure, and the residue was purified by column chromatography on silica gel (eluent: ethyl acetate-hexane) to give 343 mg of ethyl [2-[2-(5-cyano-2-methoxybenzenesulfonylamino)ethyl]-5-isopropylphenoxy]acetate.

$^1$H-NMR (DMSO-$d_6$) δ ppm: 1.14 (6H, d, J=6.9 Hz), 1.19 (3H, t, J=7.3 Hz), 2.60–2.70 (2H, m), 2.78 (1H, sept, J=6.9 Hz), 3.02–3.07 (2H, m), 3.94 (3H, s), 4.15 (2H, q, J=7.3 Hz), 4.70 (2H, s), 6.65 (1H, d, J=1.7 Hz), 6.71 (1H, dd, J=7.6, 1.7 Hz), 6.95 (1H, d, J=7.6 Hz), 7.35 (1H, d, J=8.5 Hz), 7.49 (1H, br s), 8.00–8.10 (2H, m)

Reference Example 28

The following compounds were prepared according to a similar manner to that described in Reference Example 26 or 27. Ethyl 4-[2-[2-(5-cyano-2-methoxybenzenesulfonylamino)-ethyl]-5-isopropylphenoxy]butyrate $^1$H-NMR (CDCl$_3$) δ ppm: 1.22 (6H, d, J=6.9 Hz), 1.27 (3H, t, J=7.3 Hz), 2.01–2.09 (2H, m), 2.44 (2H, t, J=7.3 Hz), 2.76 (2H, t, J=6.6 Hz), 2.80–2.90 (1H, m), 3.11–3.19 (2H, m), 3.79 (3H, s), 3.94 (2H, t, J=6.0 Hz), 4.16 (2H, q, J=7.3 Hz), 4.99 (1H, t, J=5.7 Hz), 6.64–6.68 (1H, m), 6.71–6.76 (1H, m), 6.94 (1H, d, J=7.6 Hz), 6.99 (1H, d, J=8.8 Hz), 7.78 (1H, dd, J=8.8, 2.2 Hz), 8.20 (1H, d, J=2.2 Hz)

N-[2-(2-Benzyloxy-4-isopropylphenyl)ethyl]-5-cyano-2-methoxybenzenesulfonamide $^1$H-NMR (CDCl$_3$) δ ppm: 1.23 (6H, d, J=6.9 Hz), 2.76–2.91 (3H, m), 3.14–3.21 (2H, m), 3.66 (3H, s), 4.85–4.91 (1H, m), 4.98 (2H, s), 6.74–6.79 (2H, m), 6.92 (1H, d, J=8.5 Hz), 6.97 (1H, d, J=8.2 Hz), 7.29–7.43 (5H, m), 7.73 (1H, dd, J=8.5, 1.9 Hz), 8.15 (1H, d, J=1.9 Hz)

Ethyl 2-[2-[2-(5-cyano-2-methoxybenzenesulfonylamino)-ethyl]-5-isopropylphenoxy]propionate $^1$H-NMR (CDCl$_3$) δ ppm: 1.16–1.22 (6H, m), 1.23–1.29 (3H, m), 1.57 (3H, d, J=6.8 Hz), 2.68–2.96 (3H, m), 3.16–3.37 (2H, m), 3.73 (3H, s), 4.15–4.24 (2H, m), 4.77 (1H, q, J=6.8 Hz), 5.26 (1H, t, J=5.7 Hz), 6.51–6.53 (1H, m), 6.72–6.76 (1H, m), 6.90 (1H, d, J=7.6 Hz), 6.98 (1H, d, J=8.6 Hz), 7.77 (1H, dd, J=8.6, 3.2 Hz), 8.30 (1H, d, J=3.2 Hz)

Reference Example 29

4-[2-(5-Cyano-2-methoxybenzenesulfonylamino)ethyl]-3-methoxymethoxyphenyl trifluoromethanesulfonate To a stirred solution of 21.87 g of 5-cyano-N-[2-(4-hydroxy-2-methoxymethoxyphenyl)ethyl]-2-methoxybenzene-sulfonamide and 10.21 g of N,N-dimethylaminopyridine in 230 mL of dichloromethane was added 9.38 mL of trifluoromethanesulfonic anhydride under ice-cooling. The mixture was stirred for 1 hour, and about 50 g of crushed ice was added to the reaction mixture. The mixture was concentrated under reduced pressure to remove dichloromethane, and the residue was poured into a mixture of 500 mL of ethyl acetate and 200 mL of water. The organic layer was separated, washed with water, dried over anhydrous magnesium sulfate, and filtered. The filtrate was concentrated under reduced pressure, and the residue was recrystallized from ethyl acetate-diisopropyl ether to give 24.75 g of 4-[2-(5-cyano-2-methoxybenzenesulfonylamino)ethyl]-3-methoxymethoxyphenyl trifluoromethanesulfonate as a colorless powder.

$^1$H-NMR (CDCl$_3$) δ ppm: 2.86 (2H, t, J=6.6 Hz), 3.15–3.25 (2H, m), 3.44 (3H, s), 3.86 (3H, s), 4.89 (1H, t, J=6.0 Hz), 5.16 (2H, s), 6.86 (1H, dd, J=8.5, 2.2 Hz), 7.00–7.05 (2H, m), 7.12 (1H, d, J=8.5 Hz), 7.81 (1H, dd, J=8.5, 2.2 Hz), 8.20 (1H, d, J=2.2 Hz)

Reference Example 30

5-Cyano-2-methoxy-N-[2-(3-methoxymethoxy-2'-methylthio-biphenyl-4-yl)ethyl]benzenesulfonamide A mixture of 24.75 g of 4-[2-(5-cyano-2-methoxybenzene-sulfonylamino)ethyl]-3-methoxymethoxyphenyl trifluoro-methanesulfonate, 8.32 g of 2-(methylthio)phenylboronic acid, 2.73 g of tetrakis(triphenylphosphine)palladium (0), 728 mg of tetra-n-butylammonium bromide, 10.00 g of sodium carbonte, 48 mL of water and 285 mL of toluene was heated under an argon atmosphere at 85° C. for 15 hours. The precipitate was collected by filtration, washed successively with ethyl acetate and water to give 19.74 g of 5-cyano-2-methoxy-N-[2-(3-methoxy-methoxy-2'-methylthiobiphenyl-4-yl)ethyl]benzenesulfonamide as an yellow powder.

$^1$H-NMR (CDCl$_3$) δ ppm: 2.40 (3H, s), 2.88 (2H, t, J=6.3 Hz), 3.19–3.27 (2H, m), 3.43 (3H, s), 3.82 (3H, s), 5.04 (1H, t, J=5.7 z), 5.17 (2H, s), 6.95–7.05 (2H, m), 7.08 (1H, d, J=7.6 Hz), 7.10–7.25 (3H, m), 7.25–7.30 (1H, m), 7.30–7.40 (1H, m), 7.79 (1H, dd, J=8.8, 2.2 Hz), 8.22 (1H, d, J=2.2 Hz)

Reference Example 31

The following compound was prepared according to a similar manner to that described in Reference Example 30.

N-tert-Butyl-4'-[2-(5-cyano-2-methoxybenzenesulfonylamino)-ethyl]-3'-methoxymethoxybiphenyl-2-sulfonamide $^1$H-NMR (CDCl$_3$) δ ppm: 1.01 (9H, s), 2.89 (2H, t, J=6.6 Hz), 3.23 (2H, m), 3.43 (3H, s), 3.79 (1H, s), 3.96 (3H, s), 4.99 (1H, t, J=6.0 Hz), 5.22 (2H, s), 7.06 (1H, dd, J=7.6, 1.6 Hz), 7.09 (1H, d, J=8.8 Hz), 7.15 (1H, d, J=7.6 Hz), 7.28–7.35 (2H, m), 7.49 (1H, td, J=7.6, 1.3 Hz), 7.57 (1H, td, J=7.6, 1.3 Hz), 7.82 (1H, dd, J=8.8, 2.2 Hz), 8.17 (1H, dd, J=7.6, 1.3 Hz), 8.22 (1H, d, J=2.2 Hz)

Reference Example 32

5-Cyano-2-methoxy-N-[2-(3',4',5'-trifluoro-3-methoxy-methoxybiphenyl-4-yl)ethyl]benzenesulfonamide A mixture of 10.0 g of 4-[2-(5-cyano-2-methoxybenzenesulfonylamino)ethyl]-3-methoxymethoxyphenyl trifluoromethanesulfonate, 5.33 g of bis(pinacolato)diboron, 467 mg of 1,1'-bis(diphenylphosphino)ferrocenepalladium(II) dichloride dichloromethane complex, 317 mg of 1,1'-bis(diphenylphosphino)ferrocenepalladium(II), 5.61 g of potassium acetate, and 113 mL of 1,4-dioxane was stirred under an argon atmosphere at 80° C. for 15 hours. To the reaction mixture were added 4.02 g of 1-bromo-3,4,5-trifluorobenzene, 467mg of 1,1'-bis(diphenylphosphino)ferrocenepalladium(II) dichloride dichloromethane complex, 12.14 g of potassium phosphinate, and 40 mL of 1,4-dioxane. The mixture was stirred under argon atmosphere at 80° C. for 24 hours, and ethyl acetate and water were added to the reaction mixture. The organic layer was separated, washed with water, dried over anhydrous magnesium sulfate, and filtered. The filtrate was concentrated under reduced pressure, and the residue was purified by column chromatography on aminopropylated silica gel (eluent: ethyl acetate-hexane) to give 10.09 g of 5-cyano-2-methoxy-N-[2-(3',4',5'-trifluoro-3-methoxymethoxybiphenyl-4-yl) ethyl]benzenesulfonamide.

$^1$H-NMR (CDCl$_3$) δ ppm: 2.87 (2H, t, J=6.6 Hz), 3.18–3.26 (2H, m), 3.46 (3H, s), 3.85 (3H, s), 4.92 (1H, t, J=6.0 Hz), 5.21 (2H, s), 7.02 (1H, d, J=8.5 Hz), 7.06 (1H, dd, J=7.9, 1.6 Hz), 7.10–7.20 (4H, m), 7.79 (1H, dd, J=8.5, 2.2 Hz), 8.20 (1H, d, J=2.2 Hz)

Reference Example 33

5-Cyano-N-[2-(2'-methanesulfonyl-3-methoxymethoxybiphenyl-4-yl)ethyl]-2-methoxybenzenesulfonamide To a stirred suspension of 26.44 g of 5-cyano-2-methoxy-N-[2-(3-methoxymethoxy-2'-methylthiobiphenyl-4-yl) ethyl)]-benzenesulfonamide and 35.6 g of sodium bicarbonate in a mixture of 530 mL of acetone and 106 mL of water was added two portions of 81.5 g of OXONE (trademark) every 15 minutes under ice-cooling. The mixture was stirred under the same condition for 3 hours, and 100 mL of di ethyl ether, 100 mL of water, and saturated aqueous sodium sulfate solution were added to the stirred reaction mixture under ice-cooling. The obtained mixture was concentrated under reduced pressure to remove acetone, and 300 mL of water, and diethyl ether-hexane were added to the stirred residue under ice-cooling. The mixture was stirred for 30 minutes, and the precipitate was collected by filtration, washed with water and diethyl ether-hexane to give 27.1 g of 5-cyano-N-[2-(2'-methanesulfonyl-3-methoxymethoxybiphenyl-4-yl)ethyl]-2-methoxybenzenesulfonamide as a white powder.

$^1$H-NMR (DMSO-d$_6$) δ ppm: 2.65–2.75 (2H, m), 2.79 (3H, s), 3.05–3.15 (2H, m), 3.30–3.35 (3H, m), 4.00 (3H, s), 5.15 (2H, s), 6.94 (1H, dd, J=7.6, 1.6 Hz), 7.06 (1H, d, J=1.6 Hz), 7.16 (1H, d, J=7.6 Hz), 7.35–7.45 (2H, m), 7.66 (1H, td, J=7.6, 1.3 Hz), 7.70–7.80 (2H, m), 8.05–8.15 (3H, m)

Reference Example 34

5-Cyano-N-[2-(3-hydroxy-2'-methanesulfonylbiphenyl-4-yl)-ethyl]-2-methoxybenzenesulfonamide To a suspension of 14.89 g of 5-cyano-N-[2-(2'-methanesulfonyl-3-methoxymethoxybiphenyl-4-yl)ethyl]-2-methoxybenzenesulfonamide in a mixture of 30 mL of isopropanol and 90 mL of tetrahydrofuran was added 11.7 mL of concentrated hydrochloric acid. After being stirred at 50° C. for 2 hours, the reaction mixture was diluted with 50 mL of water, and extracted with 150 mL of ethyl acetate. The organic layer was washed with saturated aqueous sodium bicarbonate solution, and brine, dried over anhydrous magnesium sulfate, and filtered. The filtrate was concentrated under reduced pressure, and the residue was purified by column chromatography on aminopropylated silica gel (eluent: ethyl acetate-methanol) to give 10.22 g of 5-cyano-N-[2-(3-hydroxy-2'-methanesulfonylbiphenyl-4-yl)ethyl]-2-Methoxybenzenesulfonamide, colorless and amorphous.

$^1$H-NMR (CDCl$_3$) δ ppm: 2.69 (3H, s), 2.87 (2H, t, J=6.9 Hz), 3.20–3.30 (2H, m), 3.98 (3H, s), 5.34 (1H, t, J=5.7 Hz), 5.93 (1H, s), 6.88 (1H, dd, J=7.6, 1.6 Hz), 6.97 (1H, d, J=1.6 Hz), 7.05–7.15 (2H, m), 7.33 (1H, dd, J=7.6, 1.3 Hz), 7.56 (1H, td, J=7.6, 1.3 Hz), 7.65 (1H, td, J=7.6, 1.3 Hz), 7.82 (1H, dd, J=8.5, 2.2 Hz), 8.15–8.25 (2H, m)

Reference Example 35

The following compounds were prepared according to a similar manner to that described in Reference Example 34.

5-Cyano-2-methoxy-N-[2-(3',4',5'-trifluoro-3-hydroxy-biphenyl-4-yl)ethyl]benzenesulfonamide $^1$H-NMR (DMSO-d$_6$) δ ppm: 2.64 (2H, t, J=7.3 Hz), 3.07 (2H, t, J=7.3 Hz), 3.96 (3H, s), 6.93 (1H, d, J=1.9 Hz), 6.99 (1H, dd, J=7.6, 1.9 Hz), 7.05 (1H, d, J=7.6 Hz), 7.35 (1H, d, J=8.5 Hz), 7.40–7.50 (2H, m), 7.95–8.05 (2H, m)

N-tert-Butyl 4'-[2-(5-cyano-2-methoxybenzenesulfonylamino)-ethyl]-3'-hydroxybiphenyl-2-sulfonamide $^1$H-NMR (CDCl$_3$) δ ppm: 1.00 (9H, s), 2.87 (2H, t, J=6.6 Hz), 3.23 (2H, m), 3.98 (3H, s), 5.28 (1H, t, J=5.7 Hz), 6.10 (1H, s), 6.91 (1H, dd, J=7.6, 1.6 Hz), 7.06 (1H, d, J=1.6 Hz), 7.10 (1H, d, J=8.5 Hz), 7.13–7.20 (2H, m), 7.29 (1H, dd, J=7.6, 1.3 Hz), 7.48 (1H, td, J=7.6, 1.3 Hz), 7.56 (1H, td, J=7.6, 1.3 Hz), 7.82 (1H, dd, J=7.6, 1.3 Hz), 8.14 (1H, dd, J=8.5, 2.2 Hz), 8.21 (1H, d, J=2.2 Hz)

Reference Example 36

The following compound was prepared according to the similar manner to that described in Reference Example 32 and 34.

Methyl 4'-[2-(5-cyano-2-methoxybenzenesulfonylamino)-ethyl]-3'-hydroxybiphenyl-2-carboxylate $^1$H-NMR (CDCl$_3$) δ ppm: 2.84 (2H, t, J=6.3 Hz), 3.20–3.30 (2H, m), 3.70 (3H, s), 3.90 (3H, s), 5.53 (1H, t, J=5.4 Hz),5.93 (1H, br), 6.67 (1H, d, J=1.6 Hz), 6.78 (1H, dd, J=7.9, 1.6 Hz), 7.00–7.05 (2H, m), 7.41 (1H, td, J=7.6, 1.3 Hz), 7.51 (1H, td, J=7.6, 1.3 Hz), 7.73 (1H, dd, J=8.8, 2.2 Hz), 7.77 (1H, dd, J=7.6, 1.3 Hz), 8.21 (1H, d, J=2.2 Hz)

Reference Example 37

Ethyl[4-[2-(5-cyano-2-methoxybenzenesulfonylamino)-ethyl]-2'-methanesulfonylbiphenyl-3-yloxy]acetate To a solution of 5.72 g of 5-cyano-N-[2-(3-hydroxy-2'-methanesulfonylbiphenyl-4-yl)ethyl]-2-methoxybenzenesulfonamide in 57 mL of N,N-dimethylformamide were added 2.46 mL of N,N-diisopropylethylamine and 1.37 mL of ethyl bromoacetate. After being stirred at 50° C. for 15 hours, and the reaction mixture was poured into 100 mL of water, and extracted with a mixture of 150 mL of ethyl acetate and 20 mL of toluene. The organic layer was washed with water and brine, dried over anhydrous magnesium sulfate, and filtered. The filtrate was concentrated under reduced pressure, and the residue was purified by column chromatography on aminopropylated silica gel (eluent: ethyl acetate-hexane) to give 2.96 g of ethyl [4-[2-(5-cyano-2-methoxybenzenesulfonylamino)ethyl]-2'-methanesulfonyl-biphenyl-3-yloxy]acetate, amorphous.

$^1$H-NMR (CDCl$_3$) δ ppm: 1.28 (3H, t, J=6.9 Hz), 2.59 (3H, s), 2.95 (2H, t, J=6.6 Hz), 3.30–3.60 (2H, m), 3.99 (3H, s), 4.23 (2H, q, J=6.9 Hz), 4.68 (2H, s), 5.43 (1H, t, J=6.3 Hz), 6.95 (1H, dd, J=7.6, 1.6 Hz), 7.04 (1H, d, J=1.6 Hz), 7.09 (1H, d, J=8.5 Hz), 7.20 (1H, d, J=7.6 Hz), 7.36 (1H, dd, J=7.6, 1.3 Hz), 7.57 (1H, td, J=7.6, 1.3 Hz), 7.65 (1H, td, J=7.6, 1.3 Hz), 7.80 (1H, dd, J=8.5, 2.2 Hz), 8.20–8.25 (2H, m)

Reference Example 38

The following compounds were prepared according to a similar manner to that described in Reference Example 37.

Ethyl[4-[2-(5-cyano-2-methoxybenzenesulfonylamino)ethyl]-3',4',5'-trifluorobiphenyl-3-yloxy]acetate $^1$H-NMR (CDCl$_3$) δ ppm: 1.32 (3H, t, J=7.3 Hz), 2.92 (2H, t, J=6.6 Hz), 3.30 (2H, q, J=6.6 Hz), 3.88 (3H, s), 4.27 (2H, q, J=7.3 Hz), 4.68 (2H, s), 5.26 (1H, t, J=6.6 Hz), 6.78 (1H, d, J=1.6 Hz), 7.00–7.14 (4H, m), 7.16 (1H, d, J=7.6 Hz), 7.78 (1H, dd, J=8.8, 2.2 Hz), 8.20 (1H, d, J=2.2 Hz)

Methyl 4'-[2-(5-cyano-2-methoxybenzenesulfonylamino)-ethyl]-3'-ethoxycarbonylmethoxybiphenyl-2-carboxylate $^1$H-NMR (CDCl$_3$) δ ppm: 1.29 (3H, t, J=6.9 Hz), 2.91 (2H, t, J=6.3 Hz), 3.25–3.35 (2H, m), 3.68 (3H, s), 3.89 (3H, s), 4.25, (2H, q, J=6.3 Hz), 4.59 (2H, s), 5.33 (1H, t, J=6.0 Hz), 6.66 (1H, d, J=1.6 Hz), 6.88 (1H, dd, J=7.6, 1.6 Hz), 7.05 (1H, d, J=8.5 Hz), 7.08 (1H, d, J=7.6 Hz), 7.30 (1H, dd, J=7.6, 1.3 Hz), 7.42 (1H, td, J=7.6, 1.3 Hz), 7.53 (1H, td, J=7.6, 1.3 Hz), 7.75–7.85 (2H, m), 8.22 (1H, d, J=2.2 Hz)

Ethyl[2'-tert-butylsulfamoyl-4-[2-(5-cyano-2-methoxy-benzenesulfonylamino)ethyl]biphenyl-3-yloxy]acetate $^1$H-NMR (CDCl$_3$) δ ppm: 0.94 (9H, s), 1.31 (3H, t, J=7.3 Hz), 2.94 (2H, t, J=6.6 Hz), 3.32 (2H, m), 3.86 (1H, s), 3.99 (3H, s), 4.27 (2H, q, J=7.3 Hz), 4.72 (2H, s), 5.28 (1H, t, J=6.3 Hz), 6.94 (1H, dd, J=7.6, 1.9 Hz), 7.08 (1H, d, J=8.8 Hz), 7.22 (1H, d, J=1.3 Hz), 7.24 (1H, d, J=7.6 Hz), 7.33 (1H, dd, J=7.6, 1.3 Hz), 7.48 (1H, td, J=7.6, 1.3 Hz), 7.56 (1H, td, J=7.6, 1.3 Hz), 7.81 (1H, dd, J=8.8, 2.2 Hz), 8.17 (1H, dd, J=7.6, 1.3 Hz), 8.21 (1H, d, J=2.2 Hz)

Reference Example 39

[2-[2-(5-Cyano-2-methoxybenzenesulfonylamino)ethyl]-5-isopropylphenoxy]acetic acid To a solution of 4.52 g of ethyl[2-[2-(5-cyano-2-methoxy-benzenesulfonylamino)ethyl]-5-isopropylphenoxy]acetate in ethanol was added 12.3 mL of 2 mol/L sodium hydroxide solution to neutralize. After being stirred at room temperature for 3 hours, the reaction mixture was concentrated, and 1 mol/L hydrochloric acid was added to the residue. After the mixture was extracted with ethyl acetate, the organic layer was washed with water and brine, and dried over anhydrous magnesium sulfate. The solvent was removed under reduced pressure to give 4.16 g of [2-[2-(5-cyano-2-methoxybenzenesulfonylamino)ethyl]-5-isopropylphenoxy] acetic acid.

$^1$H-NMR (CDCl$_3$) δ ppm: 1.22 (6H, d, J=6.3 Hz), 2.80–2.89 (3H, m), 3.18–3.24 (2H, m), 3.74 (3H, s), 4.68 (2H, s), 5.35 (1H, t, J=5.7 Hz), 6.58–6.62 (1H, m), 6.80 (1H, d, J=7.3 Hz), 6.97 (1H, d, J=7.3 Hz), 6.99 (1H, d, J=8.5 Hz), 7.30–8.10 (2H, m), 8.18 (1H, d, J=2.2 Hz)

Reference Example 40

The following compound was prepared according to a similar manner to that described in Reference Example 39.

4-[2-(5-Cyano-2-methoxybenzenesulfonylamino) ethyl]-3',4',5'-trifluorobiphenyl-3-yloxy]acetic acid $^1$H-NMR (DMSO-d$_6$) δ ppm: 2.71 (2H, t, J=7.3 Hz), 3.05–3.20 (2H, m), 3.93 (3H, s), 4.78 (2H, s), 7.10–7.15 (2H, m), 7.19 (1H, dd, J=7.9, 1.6 Hz), 7.30–7.35 (1H, m), 7.60–7.75 (3H, m), 8.00–8.05 (2H, m), 12.5–13.5 (1H, br)

Reference Example 41

Ethyl[2-[2-[2-(5-cyano-2-methoxybenzenesulfonylamino)-ethyl]-5-isopropylphenoxy]acetylamino] acetate To a stirred solution of 0.3 g of [2-[2-(5-cyano-2-methoxybenzenesulfonylamino)ethyl]-5-isopropylphenoxy]acetic acid, 0.107 g of glycine ethyl ester hydrochloride and 0.103 g of 1-hydroxybenzotriazole monohydrate in N,N-dimethylformamide were added 0.106 mL of triethylamine and 0.146 g of 1-[3-(dimethylamino)propyl]-3-ethylcarbodiimide hydrochloride under ice-cooling, and the mixture was stirred at room temperature for 15 hours. To the reaction mixture was added water, and the mixture was extracted with ethyl acetate. The organic layer was washed with 1 mol/L hydrochloric acid, saturated aqueous sodium bicarbonate solution, water and brine, and dried over anhydrous magnesium sulfate. The solvent was removed under reduced pressure, and the obtained residue was purified by column chromatography on silica gel (eluent: ethyl acetate-hexane) to give 0.33 g of ethyl [2-[2-[2-(5-cyano-2-methoxybenzenesulfonylamino)ethyl]-5-isopropylphenoxy]-acetylamino] acetate $^1$H-NMR (CDCl$_3$) δ ppm: 1.22 (6H, d, J=7.3 Hz), 1.31 (3H, t, J=7.3 Hz), 2.80–3.00 (3H, m), 3.17–3.24 (2H, m), 3.91 (3H, s), 4.16 (2H, d, J=5.5 Hz), 4.27 (2H, q, J=7.3 Hz), 4.53 (2H, s), 5.24 (1H, t, J=6.3 Hz), 6.68 (1H, d, J=1.1 Hz), 6.83 (1H, dd, J=7.9, 1.1 Hz), 7.01 (1H, d, J=7.9 Hz), 7.05 (1H, d, J=8.4 Hz), 7.80 (1H, dd, J=8.4, 2.2 Hz), 8.21 (1H, d, J=2.2 Hz)

Reference Example 42

The following compound was prepared according to a similar manner to that described in Reference Example 41.

Ethyl3-[2-[4-[2-(5-cyano-2-methoxybenzenesulfonylamino)-ethyl]-3',4',5'-trifluorobiphenyl-3-yloxy] acetylamino]-propionate $^1$H-NMR (DMSO-d$_6$) δ ppm: 1.14 (3H, t, J=7.3 Hz), 2.78 (2H, t, J=6.9 Hz), 3.12 (2H, q, J=6.9 Hz), 3.35–3.45 (2H, m), 3.93 (3H, s), 4.01 (2H, q, J=7.3 Hz), 4.59 (2H, s), 7.10–7.20 (2H, m), 7.22 (1H, dd, J=7.9, 1.6 Hz), 7.34 (1H, d, J=8.5 Hz), 7.61–7.66 (1H, m), 7.67–7.75 (2H, m), 7.87 (1H, t, J=6.0 Hz), 8.00–8.05 (2H, m)

Reference Example 43

2-[2-[2-(5-Cyano-2-methoxybenzenesulfonylamino) ethyl]-5-isopropylphenoxy]acetamide A mixture of 0.169 g of [2-[2-(5-cyano-2-methoxybenzene-sulfonylamino)ethyl]-5-isopropylphenoxy]acetic acid, 41.8 mg of ammonium chloride, 79.2 mg of 1-hydroxybenzotriazole monohydrate, 0.272 mL of N,N-diisopropylethylamine and 0.112 g of 1-[3-(dimethylamino)propyl]-3-ethylcarbodiimide hydrochloride was stirred at room temperature for 27 hours. The reaction mixture was diluted with water, and extracted with ethyl acetate. The organic layer was washed with saturated aqueous sodium bicarbonate solution and brine, and dried over anhydrous magnesium sulfate. The solvent was removed under reduced pressure, and the obtained residue was purified by column chromatography on aminopropylated silica gel (eluent: dichloromethane-ethyl acetate) to give 151.4 mg of 2-[2-[2-(5-cyano-2-methoxybenzenesulfonylamino)ethyl]-5-isopropylphenoxy]acetamide.

$^1$H-NMR (CDCl$_3$) δ ppm: 1.22 (6H, d, J=7.3 Hz), 2.83–2.92 (3H, m), 3.14–3.21 (2H, m), 3.90 (3H, s), 4.51 (2H, s), 5.21 (1H, br s), 5.87 (1H, br s), 6.70 (1H, d, J=1.3 Hz), 6.80 (1H, br s), 6.82 (1H, dd, J=7.9, 1.3 Hz), 7.00 (1H, d, J=7.9 Hz), 7.06 (1H, d, J=8.5 Hz), 7.81 (1H, dd, J=8.5, 1.9 Hz), 8.17 (1H, d, J=1.9 Hz)

Reference Example 44

The following compounds were prepared according to a similar manner to that described in Reference Example 43.

2-[2-[2-(5-Cyano-2-methoxybenzenesulfonylamino) ethyl]-5-isopropylphenoxy]-N,N-dimethylacetamide $^1$H-NMR (CDCl$_3$) δ ppm: 1.22 (6H, d, J=6.9 Hz), 2.80–2.90 (3H, m), 2.99 (3H, s), 3.06 (3H, s), 3.21–3.28 (2H, m), 3.80 (3H, s), 4.67 (2H, s), 5.71 (1H, t, J=6.0 Hz), 6.64 (1H, d, J=1.3 Hz), 6.77 (1H, dd, J=7.6, 1.3 Hz), 6.95 (1H, d, J=7.6 Hz), 6.99 (1H, d, J=8.5 Hz), 7.76 (1H, dd, J=8.5, 2.2 Hz), 8.18 (1H, d, J=2.2 Hz)

5-Cyano-N-[2-[4-isopropyl-2-(2-morpholin-4-yl-2-oxoethoxy)-phenyl]ethyl]-2-methoxybenzenesulfonamide $^1$H-NMR (CDCl$_3$) δ ppm: 1.22 (6H, d, J=6.9 Hz), 2.79–2.90 (3H, m), 3.22 (2H, q, J=6.0 Hz), 3.50–3.56 (2H, m), 3.60–3.72 (6H, m), 3.82 (3H, s), 4.68 (2H, s), 5.47 (1H, t, J=6.0 Hz), 6.66 (1H, d, J=1.3 Hz), 6.79 (1H, dd, J=7.9, 1.3 Hz), 6.96 (1H, d, J=7.9 Hz), 7.00 (1H, d, J=8.5 Hz), 7.77 (1H, dd, J=8.5, 2.2 Hz), 8.18 (1H, d, J=2.2 Hz)

Reference Example 45

(4-Isopropylphenyl)acetonitrile

To a stirred solution of 100 g of 4-isopropylbenzyl chloride in 1500 mL of N,N-dimethylformamide was added 32.0 g of sodium cyanide under ice-cooling. The mixture was stirred at 70° C. for 4 hours, and water was added to the reaction mixture. The mixture was extracted with ethyl acetate, and the organic layer was washed with water and brine, and dried over anhydrous magnesium sulfate. The solvent was removed under reduced pressure to give 96.5 g of (4-isopropylphenyl)acetonitrile.

$^1$H-NMR (CDCl$_3$) δ ppm: 1.24 (6H, d, J=6.9 Hz), 2.91 (1H, sept, J=6.9 Hz), 3.70 (2H, s), 7.22–7.27 (4H, m)

Reference Example 46

2-(4-Isopropylphenyl)ethylamine hydrochloride

To 1000 mL of 1.0 mol/L boran-tetrahydrofuran complex was added dropwise a solution of 79.6 g of (4-isopropylphenyl)-acetonitrile in 400 mL of tetrahydrofuran under ice-cooling with stirring, and the mixture was strred at room temperature for 2 hours. To the stirred reaction mixture was added 500 mL of methanol under ice-cooling during 30 minutes, and the mixture was stirred at the same temperature for 20 minutes. After the reaction mixture was concentrated under reduced pressure, to the residue were added isopropanol and 500 mL of 2 mol/L hydrochloric acid. The solvent was removed under reduced pressure, and the residue was recrystallized from isopropanol-diisopropyl ether to give 41.5 g of 2-(4-Isopropylphenyl)ethylamine hydrochloride.

$^1$H-NMR (DMSO-d$_6$) δ ppm: 1.18 (6H, d, J=6.9 Hz), 2.81–2.92 (3H, m), 2.96–3.05 (2H, m), 7.14–7.26 (4H, m), 8.05 (3H, br s)

Reference Example 47

2,2,2-Trifluoro-N-[2-(4-isopropylphenyl)ethyl]acetamide

To a stirred solution of 2.59 g of 2-(4-isopropyl-phenyl)ethylamine in 10 mL of N,N-dimethylformamide were added 4.0 mL of triethylamine and 1.95 mL of trifluoroacetic anhydride under ice-cooling, and the mixture was stirred at room temperature for an hour. To the reaction mixture were added water and 10 mL of 1 mol/L hydrochloric acid, and the mixture was extracted three times with 20 mL of ethyl acetate. The organic layers were combined and washed with water, saturated aqueous sodium bicarbonate solution, and brine. The mixture was dried over anhydrous magnesium sulfate, and the solvent was removed under reduced pressure. Hexane was added to the residue, and the crystal was collected by filtration to give 2.39 g of 2,2,2-trifluoro-N-[2-(4-isopropylphenyl)ethyl)acetamide.

$^1$H-NMR (CDCl$_3$) δ ppm: 1.24 (6H, d, J=6.9 Hz), 2.79–2.96 (3H, m), 3.60 (2H, q, J=6.6 Hz), 6.33 (1H, br s), 7.11 (2H, d, J=7.9 Hz), 7.20 (2H, d, J=7.9 Hz)

Reference Example 48

5-Isopropyl-2-[2-(2,2,2-trifluoroacetylamino)ethyl]-benzenesulfonyl chloride

Chlorosulfonic acid (2.05 mL) was added to 1.6 g of 2,2,2-trifluoro-N-[2-(4-isopropylphenyl)ethyl]acetamide, and the mixture was stirred at room temperature for 3 hours. The reaction mixture was poured into ice-water, and water was added to the mixture. The mixture was extracted with ethyl acetate, and the organic layer was washed with brine, and dried over anhydrous magnesium sulfate. The solvent was removed under reduced pressure, and the residue was purified by column chromatography on silica gel (eluent: ethyl acetate-hexane) to give 0.463 g of 5-isopropyl-2-[2-(2,2,2-trifluoroacetyl-amino)ethyl]benzenesulfonyl chloride.

$^1$H-NMR (CDCl$_3$) δ ppm: 1.30 (6H, d, J=6.9 Hz), 3.02 (1H, sept, J=6.9 Hz), 3.39 (2H, t, J=7.3 Hz), 3.68–3.77 (2H, m), 6.66 (1H, brs), 7.42 (1H, d, J=7.9 Hz), 7.57 (1H, dd, J=7.9, 1.9 Hz), 7.95 (1H, d, J=1.9 Hz)

Reference Example 49

N-[2-(2-tert-Butylsufamoyl-5-isopropylphenyl)ethyl]-2,2,2-trifluoroacetamide

To a solution of 0.463 g of 5-isopropyl-2-[2-(2,2,2-trifluoroacetylamino)ethyl]benzenesulfonyl chloride in 30 mL of tetrahydrofuran was added 0.500 mL of tert-butylamine. The mixture was sealed and stirred at room temperature overnight. The reaction mixture was concentrated under reduced pressure, and the residue was dissolved in 30 mL of water and 10 mL of 1 mol/L hydrochloric acid. The mixture was extracted with ethyl acetate, and the organic layer was washed with water, saturated aqueous sodium bicarbonate solution, and brine. The organic layer was dried over anhydrous magnesium sulfate, and the solvent was removed under reduced pressure to give 0.481 g of N-[2-(2-tert-butylsufamoyl-5-isopropylphenyl)ethyl]-2,2,2-trifluoroacetamide.

$^1$H-NMR (CDCl$_3$) δ ppm: 1.21–1.35 (15H, m), 2.90–3.05 (1H, m), 3.22–3.36 (2H, m), 3.61–3.75 (2H, m), 4.54–4.66 (1H, m), 7.32–7.49 (2H, m), 7.84–7.95 (1H, m)

Reference Example 50

2-(2-Aminoethyl)-N-tert-butyl-5-isopropylbenzenesulfonamide

To a solution of 0.481 g of N-[2-(2-tert-butylsufamoyl-5-isopropylphenyl)ethyl]-2,2,2-trifluoroacetamide in 5 mL of ethanol was added 5 mL of 2 mol/L sodium hydroxide solution, and the mixture was allowed to stand at room temperature for 4 hours. To the reaction mixture was added 5 mL of 2 mol/L hydrochloric acid, and the mixture was concentrated under reduced pressure. To the residue was added saturated aqueous sodium bicarbonate solution, and the mixture was extracted with ethyl acetate. The organic layer was washed with brine, and dried over anhydrous magnesium sulfate. The solvent was removed under reduced pressure to give 0.288 g of 2-(2-aminoethyl)-N-tert-butyl-5-isopropylbenzenesulfonamide.

$^1$H-NMR (CDCl$_3$) δ ppm: 1.20–1.28 (15H, m), 2.94 (1H, sept, J=6.9 Hz), 3.09 (2H, t, J=6.6 Hz), 3.21 (2H, t, J=6.6 Hz), 7.23–7.28 (1H, m), 7.33 (1H, dd, J=7.9, 1.9 Hz), 7.91 (1H, d, J=1.9 Hz)

Reference Example 51

3-[[2-(2-tert-Butylsulfamoyl-4-isopropylphenyl)ethyl]-sulfamoyl]-4-methoxybenzamide To a suspension of 241 mg of 5-carbamoyl-2-methoxybenzenesulfonyl chloride and 288 mg of 2-(2-aminoethyl)-N-tert-butyl-5-isopropylbenzenesulfonamide in 10 mL of N,N-dimethylformamide was added 0.32 mL of triethylamine, and the mixture was stirred at room temperature for 3 days. To the reaction mixture was added 30 mL of water, and the mixture was stirred at the same temperature for 1 hour. To the mixture was added 10 mL of 1 mol/L hydrochloric acid, and the mixture was extracted three times with 20 mL of ethyl acetate. The organic layers were combined and washed with 30 mL of water, and dried over anhydrous magnesium sulfate. The solvent was removed under reduced pressure to give 426 mg of 3-[[2-(2-tert-butylsulfamoyl-4-isopropylpheyl)ethyl]sulfamoyl]-4-methoxybenzamide.

$^1$H-NMR (CDCl$_3$) δ ppm: 1.23 (6H, d, J=6.9 Hz), 1.25 (9H, s), 2.86–2.97 (1H, m), 3.13–3.20 (2H, m), 3.21–3.30 (2H, m), 3.99 (3H, s), 5.20 (1H, br s), 5.37 (1H, t, J=6.0 Hz), 5.43–5.69 (1H, br), 6.60–6.88 (1H, br), 7.05 (1H, d, J=8.8 Hz), 7.14(1H, d, J=7.9 Hz), 7.25–7.30 (1H, m), 7.88 (1H, d, J=1.9 Hz), 8.13 (1H, dd, J=8.8, 2.5 Hz), 8.32 (1H, d, J=2.5 Hz)

Reference Example 52

N-tert-Butyl-2-[2-(5-cyano-2-methoxybenzenesulfonylamino)-ethyl]-5-isopropylbenzenesulfonamide To a stirred solution of 420 mg of 3-[[2-(2-tert-butylsulfamoyl-4-isopropylphenyl)ethyl]sulfamoyl]-4-methoxybenzamide in 30 mL of dichloromethane were added 0.48 mL of triethylamine and 0.245 mg of trifluoroacetic anhydride under ice-cooling, and the mixture was stirred at room temperature overnight. To the reaction mixture was added 1 mL of triethylamine, and the mixture was stirred at the same temperature for 2 hours. To the reaction mixture were added water and 30 mL of 1 mol/L hydrochloric acid, and the mixture was extracted three times with 30 mL of dichloromethane. The organic layers were combined, washed with water, and brine, and dried over anhydrous magnesium sulfate. After the solvent was removed under reduced pressure, ethyl acetate and hexane were added to the residue, and the crystal was collected by filtration to give 325 mg of N-tert-butyl-2-[2-(5-cyano-2-methoxy-benzenesulfonylamino)ethyl]-5-isopropylbenzenesulfonamide.

$^1$H-NMR (CDCl$_3$) δ ppm: 1.23 (9H, s), 1.25 (6H, d, J=6.9 Hz), 2.93 (1H, sept, J=6.9 Hz), 3.17 (2H, t, J=6.6 Hz), 3.22–3.29 (2H, m), 3.94 (3H, s), 4.36 (1H, br s), 5.43 (1H, t, J=5.7 Hz), 6.99 (1H, d, J=8.5 Hz), 7.20 (1H, d, J=7.9 Hz), 7.29 (1H, dd, J=7.9, 1.6 Hz), 7.79 (1H, dd, J=8.5, 1.9 Hz), 7.84 (1H, d, J=1.6 Hz), 8.15 (1H, d, J=1.9 Hz)

Reference Example 53

Ethyl[2-[2-[(5-cyano-2-methoxybenzenesulfonyl)-(2-methyl-1,3-thiazole-4-ylmethyl)amino]ethyl]-5-isopropylphenoxy]-acetate A suspension of 300 mg of ethyl[2-(2-(5-cyano-2-methoxy-benzenesulfonylamino)ethyl]-5-isopropylphenoxy]acetate, 132 mg of 4-chloromethyl-2-methyl-1,3-thiazole hydrochloride and 189 mg of potassium carbonate in 2.0 mL of N,N-dimethylformamide was stirred at room temperature for 18 hours, then at 50° C. for 3 hours. To the reaction mixture were added 60 mg of 4-chloromethyl-2-methyl-1,3-thiazole hydrochloride and 45 mg of potassium carbonate, and the mixture was stirred at the same temperature for 2.7 hours. To the reaction mixture were added 60 mg of 4-chloromethyl-2-methyl-1,3-thiazole hydrochloride and 45 mg of potassium carbonate, and the mixture was stirred at the same temperature for 3 hours. Furthermore, to the reaction mixture was added 2 mL of N,N-dimethylformamide, and the mixture was stirred at the same temperature for 1.5 hours. To the reaction mixture were added water and saturated aqueous sodium bicarbonate solution, and the mixture was extracted with ethyl acetate. The organic layer was washed with water, aqueous sodium chloride solution, and brine, and dried over anhydrous magnesium sulfate. The solvent was removed under reduced pressure, and the residue was purified by column chromatography on silica gel (eluent: ethyl acetate-hexane) to give 311 mg of ethyl [2-[2-[(5-cyano-2-methoxybenzenesulfonyl)-(2-methyl-1,3-thiazol-4-ylmethyl)amino)ethyl]-5-isopropylphenoxy]acetate.

$^1$H-NMR (CDCl$_3$) δ ppm: 1.19 (6H, d, J=6.9 Hz), 1.27 (3H, t, J=7.3 Hz), 2.60 (3H, s), 2.76–2.87 (3H, m), 3.57–3.65 (2H, m), 3.92 (3H, s), 4.24 (2H, q, J=7.3 Hz), 4.56 (2H, s), 4.67 (2H, s), 6.49 (1H, d, J=1.6 Hz), 6.73 (1H, dd, J=7.6, 1.6 Hz), 6.95 (1H, d, J=8.5 Hz), 6.97 (1H, d, J=7.6 Hz), 7.02 (1H, s), 7.71 (1H, dd, J=8.5, 2.2 Hz), 8.22 (1H, d, J=2.2 Hz)

Reference Example 54

Amino-[4-benzyloxy-3-[[2-[4-isopropyl-2-(ethoxycarbonylmethoxy)phenyl]ethyl]sulfamoyl]phenyl]methylenecarbamoyloxymethyl 2,2-dimethylpropionate To a solution of 131 mg of ethyl [2-[2-(5-carbamimidoyl-2-hydroxybenzenesulfonylamino)ethyl]-5-isopropylphenoxy]-acetate in 5 mL of N,N-dimethylformamide was added 0.91 mL of N,N-diisopropylethylamine. To the stirred mixture was added 0.069 mL of benzyl bromide at 40° C., and the mixture was stirred at room temperature over night. To the reaction mixture were added 0.91 mL of N,N-diisopropylethylamine and 86 mg of 4-nitrophenoxycarbonyloxymethyl 2,2-dimethylpropionate, and the mixture was stirred at room temperature for 6 hours. To the reaction mixture were added 10 mL of water and 10 mL of brine, and the mixture was extracted with ethyl acetate. The organic layer was washed with brine, and dried over anhydrous magnesium sulfate. The solvent was removed under reduced pressure, and the residue was purified by column chromatography on silica gel (eluent: ethyl acetate-hexane) to give 99 mg of amino-[4-benzyloxy-3-[[2-[4-isopropyl-2-(ethoxycarbonylmethoxy)phenyl]-ethyl]sulfamoyl]phenyl]methylenecarbamoyloxymethyl 2,2-dimethylpropionate.

$^1$H-NMR (CDCl$_3$) δ ppm: 1.19 (6H, d, J=6.9 Hz), 1.22 (9H, s), 1.27 (3H, t, J=7.3 Hz), 2.70–2.86 (3H, m), 3.17–3.25 (2H, m), 4.21 (2H, q, J=7.3 Hz), 4.47 (2H, s), 5.05–5.11 (1H, m), 5.17 (2H, s), 5.86 (2H, s), 6.50 (1H, d, J=1.6 Hz), 6.71 (1H, dd, J=7.6, 1.6 Hz), 6.86 (1H, d, J=7.6 Hz), 7.04 (1H, d, J=8.8 Hz), 7.29–7.48 (6H, m), 8.28 (1H, dd, J=8.8, 2.5 Hz), 8.32 (1H, d, J=2.5 Hz), 9.40–9.80 (1H, br)

Reference Example 55

The following compounds were prepared according to a similar manner to that described in Reference Example 54.

Amino-[4-benzyloxy-3-[[2-[4-isopropyl-2-(ethoxycarbonylmethoxy)phenyl]ethyl]sulfamoyl]phenyl]methylenecarbamoyloxymethyl 2-acetoxy-2-methylpropionate $^1$H-NMR (CDCl$_3$) δ ppm: 1.19 (6H, d, J=6.9 Hz), 1.27 (3H, t, J=7.3 Hz), 1.56 (6H, s), 2.04 (3H, s), 2.73 (2H, t, J=6.9 Hz), 2.81 (1H, sept, J=6.9 Hz), 3.17–3.24 (2H, m), 4.21 (2H, q, J=7.3 Hz), 4.47 (2H, s), 5.09 (1H, t, J=6.0 Hz),5.16 (2H, s), 5.88 (2H, s), 6.50 (1H, d, J=1.6 Hz), 6.70 (1H, dd, J=7.6, 1.6 Hz), 6.86 (1H, d, J=7.6 Hz), 6.88–7.17

(1H, m), 7.30–7.48 (5H, m), 8.27 (1H, dd, J=8.8, 2.5 Hz), 8.32 (1H, d, J=2.5 Hz), 9.20–9.90 (1H, br)

Ethyl[4-[2-[5-[amino(butoxycarbonylimino)methyl]-2-benzyloxybenzenesulfonylamino]ethyl]-2'-methanesulfonyl-biphenyl-3-yl]oxyacetate ¹H-NMR (CDCl₃) δ ppm: 0.95 (3H, t, J=7.3 Hz), 1.24 (3H, t, J=7.3 Hz), 1.39–1.50 (2H, m), 1.66–1.76 (2H, m), 2.54 (3H, s), 2.85 (2H, t, J=6.9 Hz), 3.21–3.30 (2H, m), 4.12–4.21 (4H, m), 4.58 (2H, s), 5.18 (1H, t, J=6.0 Hz), 5.29 (2H, s), 6.89 (1H, dd, J=7.6, 1.6 Hz), 6.98 (1H, d, J=1.6 Hz), 7.098 (1H, d, J=7.6 Hz), 7.103 (1H, d, J=8.8 Hz), 7.32 (1H, dd, J=7.6, 1.3 Hz), 7.34–7.43 (3H, m), 7.44–7.50 (2H, m), 7.55 (1H, td, J=7.6, 1.6 Hz), 7.63 (1H, td, J=7.6, 1.3 Hz), 8.22 (1H, dd, J=7.6, 1.6 Hz), 8.26 (1H, dd, J=8.8, 2.5 Hz), 8.33 (1H, d, J=2.5 Hz), 9.20–10.00 (1H, br)

Example 1

Ethyl[4-[2-(5-cyano-2-hydroxybenzenesulfonylamino)-ethyl]-2'-methanesulfonylbiphenyl-3-yloxy]acetate (Compound 1)

To a solution of 4.62 g of ethyl [4-[2-(5-cyano-2-methoxybenzenesulfonylamino)ethyl]-2'-methanesulfonylbiphenyl-3-yloxy]acetate in 40 mL of N,N-dimethylformamide was added 1.03 g of lithium chloride, and the mixture was stirred at 140° C for 2 hours. After being cooled to room temperature, the reaction mixture was poured into a mixture of 60 mL of ethyl acetate, 6 mL of toluene, and 32 mL of 1 mol/L hydrochloric acid. The organic layer was separated, and washed with 1 mol/L hydrochloric acid and brine. The organic layer was dried over anhydrous magnesium sulfate, and filtered. The filtrate was concentrated under reduced pressure, and the residue was purified by column chromatography on aminopropylated silica gel (eluent: acetic acid-ethyl acetate) to give 3.67 g of ethyl [4-[2-(5-cyano-2-hydroxybenzenesulfonylamino)ethyl]-2'-methanesulfonyl-biphenyl-3-yloxy]acetate, colorless and amorphous.

¹H-NMR (DMSO-d₆) δ ppm: 1.14 (3H, t, J=7.3 Hz), 2.71 (3H, s), 2.75–2.82 (2H, m), 3.07–3.16 (2H, m), 4.10 (2H, q, J=7.3 Hz), 4.75 (2H, s), 6.90–6.95 (2H, m), 7.12 (1H, d, J=8.5 Hz), 7.20–7.30 (1H, m), 7.38 (1H, dd, J=7.6, 1.3 Hz), 7.45–7.60 (1H, br s), 7.65 (1H, td, J=7.6, 1.3 Hz), 7.75 (1H, td, J=7.6, 1.3 Hz), 7.87 (1H, dd, J=8.5, 2.2 Hz), 8.01 (1H, d, J=2.2 Hz), 8.07 (1H, dd, J=7.6, 1.3 Hz), 11.80–12.30 (1H, br)

Example 2

Ethyl[2-[2-(5-cyano-2-hydroxybenzenesulfonylamino)-ethyl]-5-isopropylphenoxy]acetate (Compound 2)

To a solution of 148 mg of ethyl[2-[2-(5-cyano-2-methoxybenzenesulfonylamino)ethyl]-5-isopropylphenoxy]acetate in 3 mL of N,N-dimethylformamide was added 41 mg of lithium chloride, and the mixture was stirred at 140° C. for 3 hours. After being cooled to room temperature, the reaction mixture was concentrated under reduced pressure. To the residue was added aqueous 10% citric acid solution to adjust pH4, and the mixture was extracted with 100 mL of ethyl acetate. The organic layer was washed with water and brine, and dried over anhydrous magnesium sulfate. The solvent was removed under reduced pressure to give 139 mg of ethyl[2-[2-(5-cyano-2-hydroxybenzenesulfonylamino)-ethyl]-5-isopropylphenoxy]acetate.

¹H-NMR (DMSO-d₆) δ ppm: 1.14 (6H, d, J=6.9 Hz), 1.18 (3H, t, J=7.3 Hz), 2.60–2.70 (2H, m), 2.78 (1H, sept, J=6.9 Hz), 2.95–3.10 (2H, m), 4.14 (2H, q, J=7.3 Hz), 4.73 (2H, s), 6.66 (1H, d, J=1.4 Hz), 6.72 (1H, dd, J=7.9, 1.4 Hz), 6.97 (1H, d, J=7.9 Hz), 7.09 (1H, d, J=8.5 Hz), 7.45 (1H, t, J=5.7 Hz), 7.85 (1H, dd, J=8.5, 2.3 Hz), 7.98 (1H, d, J=2.3 Hz), 11.95 (1H, br s)

Example 3

The following compounds were prepared according to a similar manner to that described in Example 1 or 2.

Ethyl[4-[2-(5-cyano-2-hydroxybenzenesulfonylamino)ethyl]-3',4',5'-trifluorobiphenyl-3-yloxy]acetate (Compound 3)

¹H-NMR (DMSO-d₆) δ ppm: 1.19 (3H, t, J=7.3 Hz), 2.70–2.80 (2H, m), 3.05–3.15 (2H, m), 4.15 (2H, q, J=7.3 Hz), 4.90 (2H, s), 7.06 (1H, d, J=8.5 Hz), 7.15–7.25 (3H, m), 7.48 (1H, t, J=5.7 Hz), 7.65–7.75 (2H, m), 7.83 (1H, dd, J=8.5, 2.2 Hz), 7.96(1H, d, J=2.2 Hz), 11.93 (1H, s)

Methyl 4'-[2-(5-cyano-2-hydroxybenzenesulfonylamino)-ethyl]-3'-ethoxycarbonylmethoxybiphenyl-2-carboxylate (Compound 4)

¹H-NMR (CDCl₃) δ ppm: 1.32 (3H, t, J=7.3 Hz), 2.94 (2H, t, J=6.0 Hz), 3.30–3.40 (2H, m), 3.79 (3H, s), 4.31 (2H, q, J=7.3 Hz), 4.50 (2H, s), 5.84 (1H, t, J=5.0 Hz), 6.60(1H, d, J=1.6 Hz), 6.82 (1H, dd, J=7.6, 1.6 Hz), 6.89 (1H, d, J=8.5 Hz), 7.05 (1H, d, J=7.6 Hz), 7.32 (1H, dd, J=7.9, 1.3 Hz), 7.44 (1H, td, J=7.9, 1.3 Hz), 7.55–7.60 (2H, m), 7.91 (1H, dd, J=7.9, 1.3 Hz), 8.06 (1H, d, J=2.2 Hz), 8.90–9.10 (1H, br)

Ethyl[2-[2-[2-(5-cyano-2-hydroxybenzenesulfonylamino)-ethyl]-5-isopropylphenoxy]acetylamino]acetate (Compound 5)

¹H-NMR (CDCl₃) δ ppm: 1.23 (6H, d, J=6.9 Hz), 1.35 (3H, t, J=6.9 Hz), 2.84–2.92 (3H, m), 3.22–3.28 (2H, m), 4.18 (2H, d, J=5.4 Hz), 4.32 (2H, q, J=6.9 Hz), 4.53 (2H, s), 5.89–5.94 (1H, m), 6.65 (1H, d, J=1.3 Hz), 6.85 (1H, dd, J=7.9, 1.3 Hz), 7.03–7.10 (3H, m), 7.65 (1H, dd, J=8.8, 2.2 Hz), 7.95 (1H, d, J=2.2 Hz), 9.35 (1H, br s)

2-[2-[2-(5-Cyano-2-hydroxybenzenesulfonylamino)ethyl]-5-isopropylphenoxy]acetamide (Compound 6)

¹H-NMR (DMSO-d₆) δ ppm: 1.16 (6H, d, J=6.9 Hz), 2.68–2.74 (2H, m), 2.77–2.84 (1H, m), 2.98–3.06 (2H, m), 4.41 (2H, s), 6.70 (1H, d, J=1.3 Hz), 6.73 (1H, dd, J=7.6, 1.3 Hz), 6.98 (1H, d, J=7.6 Hz), 7.11 (1H, d, J=8.8 Hz), 7.24 (1H, br s), 7.47–7.54 (2H, m), 7.86 (1H, dd, J=8.8, 2.5 Hz), 7.98 (1H, d, J=2.5 Hz), 12.00 (1H, br s)

Ethyl 4-[2-[2-(5-cyano-2-hydroxybenzenesulfonylamino)-ethyl]-5-isopropylphenoxy]acetate (Compound 7)

¹H-NMR (CDCl₃) δ ppm: 1.23 (6H, d, J=6.9 Hz), 1.29 (3H, t, J=7.3 Hz), 2.09–2.17 (2H, m), 2.52 (2H, t, J=7.3 Hz), 2.76 (2H, t, J=6.9 Hz), 2.81–2.90 (1H, m), 3.14–3.24 (2H, m), 4.00 (2H, t, J=6.0 Hz), 4.19 (2H, q, J=7.3 Hz), 5.53 (1H, t, J=5.7 Hz), 6.66 (1H, d, J=1.3 Hz), 6.74 (1H, dd, J=7.6, 1.3 Hz), 6.94 (1H, d, J=7.6 Hz), 7.05 (1H, d, J=8.8 Hz), 7.63 (1H, dd, J=8.8, 1.9 Hz), 7.94 (1H, d, J=1.9 Hz), 9.73 (1H, br s)

N-[2-(2-Benzyloxy-4-isopropylphenyl)ethyl]-5-cyano-2-hydroxybenzenesulfonamide (Compound 8)

$^1$H-NMR (CDCl$_3$) δ ppm: 1.24 (6H, d, J=6.9 Hz), 2.78 (2H, t, J=6.3 Hz), 2.83–2.93 (1H, m), 3.24 (2H, t, J=6.3 Hz), 5.04 (2H, s), 5.29 (1H, br s), 6.77 (1H, d, J=7.9 Hz), 6.80 (1H, s), 6.94 (1H, d, J=7.9 Hz), 7.00 (1H, d, J=8.5 Hz), 7.29–7.49 (5H, m), 7.58 (1H, dd, J=8.5, 1.9 Hz), 7.69 (1H, d, J=1.9 Hz)

Ethyl 2-[2-[2-(5-cyano-2-hydroxybenzenesulfonylamino)-ethyl]-5-isopropylphenoxy]propionate (Compound 9)

$^1$H-NMR (CDCl$_3$) δ ppm: 1.17–1.23 (6H, m), 1.32 (3H, t, J=7.0 Hz), 1.63 (3H, d, J=6.8 Hz), 2.59–2.66 (1H, m), 2.79–2.87 (1H, m), 3.05–3.19 (2H, m), 3.47–3.56 (1H, m), 4.25–4.35 (2H, m), 4.91 (1H, q, J=6.8 Hz), 6.31–6.37 (1H, m), 6.50–6.53 (1H, m), 6.71–6.75 (1H, m), 6.91 (1H, d, J=7.6 Hz), 6.99 (1H, d, J=8.7 Hz), 7.59 (1H, dd, J=8.7, 2.2 Hz), 7.93 (1H, d, J=2.2 Hz), 9.39 (1H, br s)

2-[2-[2-(5-Cyano-2-hydroxybenzenesulfonylamino)ethyl]-5-isopropylphenoxy]-N,N-dimethylacetamide (Compound 10)

$^1$H-NMR (DMSO-d$_6$) δ ppm: 1.15 (6H, d, J=6.9 Hz), 2.61–2.70 (2H, m), 2.72–2.84 (1H, m), 2.84 (3H, s), 2.99 (3H, s), 3.00–3.10 (2H, m), 4.74 (2H, s), 6.66–6.75 (2H, m), 6.95 (1H, d, J=7.9 Hz), 7.12 (1H, d, J=8.3 Hz), 7.42–7.51 (1H, m), 7.85 (1H, dd, J=8.3, 2.2 Hz), 7.97 (1H, d, J=2.2 Hz), 12.00 (1H, br s)

5-Cyano-2-hydroxy-N-[2-[4-isopropyl-2-(2-morpholin-4-yl-2-oxoethoxy)phenyl]ethyl]benzenesulfonamide (Compound 11)

$^1$H-NMR (DMSO-d$_6$) δ ppm: 1.15 (6H, d, J=6.9 Hz), 2.61–2.69 (2H, m), 2.74–2.83 (1H, m), 2.99–3.10 (2H, m), 3.42–3.52 (4H, m), 3.53–3.63 (4H, m), 4.76 (2H, s), 6.68–6.75 (2H, m), 6.96 (1H, d, J=7.6 Hz), 7.10 (1H, d, J=8.2 Hz), 7.47 (1H, t, J=5.7 Hz), 7.85 (1H, dd, J=8.2, 1.9 Hz), 7.98 (1H, d, J=1.9 Hz), 11.95 (1H, br s)

Ethyl[2'-tert-butylsulfamoyl-4-[2-(5-cyano-2-hydroxy-benzenesulfonylamino)ethyl]biphenyl-3-yloxy]acetate (Compound 12)

$^1$H-NMR (DMSO-d$_6$) δ ppm: 0.92 (9H, s), 1.16 (3H, t, J=6.9 Hz), 2.70–2.80 (2H, m), 3.00–3.15 (2H, m), 4.12 (2H, q, J=6.9 Hz), 4.71 (2H, s), 6.89 (1H, dd, J=7.6, 1.6 Hz), 6.95 (1H, d, J=1.6 Hz), 7.00–7.10 (1H, br s), 7.10–7.50 (4H, m), 7.54 (1H, td, J=7.6, 1.3 Hz), 7.62 (1H, td, J=7.6, 1.3 Hz), 7.78 (1H, br s), 7.94 (1H, br s), 8.03 (1H, d, J=7.6, 1.3 Hz), 11.50–12.50 (1H, br)

Ethyl[2-[2-[(5-cyano-2-hydroxybenzenesulfonyl)-(2-methyl-1,3-thiazole-4-ylmethyl)amino)ethyl]-5-isoprpoylphenoxy]-acetate (Compound 13)

$^1$H-NMR (DMSO-d$_6$) δ ppm: 1.08–1.20 (9H, m), 2.56–2.65 (5H, m), 2.68–2.83 (1H, m), 3.16–3.36 (2H, m), 4.12 (2H, q, J=7.3 Hz), 4.62 (2H, s), 4.68 (2H, s), 6.12 (1H, d, J=8.8 Hz), 6.55–6.65 (2H, m), 6.66–6.72 (1H, m), 6.83–6.89 (1H, m), 7.09 (1H, dd, J=8.8, 2.5 Hz), 7.19 (1H, s), 7.58–7.63 (1H, m)

N-tert-Butyl-2-[2-(5-cyano-2-hydroxybenzenesulfonylamino)-ethyl]-5-isoprpoylbenzenesulfonamide (Compound 14)

$^1$H-NMR (CDCl$_3$) δ ppm: 1.20–1.31 (15H, m), 2.93–3.01 (1H, m), 3.14–3.24 (2H, m), 3.30–3.41 (2H, m), 4.41–4.55 (1H, m), 5.55–6.30 (1H, br), 6.97–7.09 (1H, m), 7.11–7.21 (1H, m), 7.56–7.66 (1H, m), 7.81–7.90 (1H, m), 7.97–8.11 (1H, m)

Example 4

The following compound was prepared according to the similar manner to that described in Reference Example 37 and Example 1 or 2.

Ethyl 3-[2-[4-[2-(5-cyano-2-hydroxybenzenesulfonylamino)-ethyl]-3',4',5'-trifluorobiphenyl-3-yloxy]acetylamino]-propionate (Compound 15)

$^1$H-NMR (DMSO-d$_6$) δ ppm: 1.14 (3H, t, J=7.3 Hz), 2.80 (2H, t, J=7.3 Hz), 3.07–3.14 (2H, m), 3.35–3.45 (2H, m), 4.01 (2H, q, J=7.3 Hz), 4.60 (2H, s), 7.07 (1H, d, J=8.5 Hz), 7.15–7.25 (3H, m), 7.47–7.54 (1H, m), 7.65–7.75 (2H, m), 7.83 (1H, dd, J=8.5, 2.2 Hz), 7.87 (1H, t, J=6.0 Hz), 7.96 (1H, d, J=2.2 Hz), 11.96 (1H, br s)

Example 5

5-Cyano-N-[2-(2-hydrazinocarbonylmethoxy-4-isopropyl-phenyl)ethyl]-2-hydroxybenzenesulfonamide (Compound 16)

Ethyl[2-[2-(5-cyano-2-hydroxybenzenesulfonylamino)-ethyl]-5-isoproylphenoxy]acetate (0.266 g) was dissolved in 5 mL of ethanol. To the solution was added 0.087 mL of hydrazine monohydrate at room temperature, and the mixture was refluxed for 1 hour. The solvent was removed under reduced pressure to give 0.258 g of 5-cyano-N-[2-(2-hydrazinocarbonylmethoxy-4-isopropylphenyl)ethyl]-2-hydroxybenzenesulfonamide.

$^1$H-NMR (DMSO-d$_6$) δ ppm: 1.17 (6H, d, J=6.9 Hz), 2.66–2.73 (2H, m), 2.75–2.84 (3H, m), 4.47 (2H, s), 5.42 (1H, br s), 6.30 (1H, d, J=8.8 Hz), 6.73–6.77 (2H, m), 7.01 (1H, d, J=7.9 Hz), 7.22 (1H, dd, J=8.8, 2.5 Hz), 7.56 (1H, d, J=2.5 Hz), 9.00–9.60 (1H, m)

Example 6

5-Cyano-2-hydroxy-N-[2-[4-isopropyl-2-(5-oxo-4,5-dihydro-[1,3,4]oxadiazol-2-ylmethoxy)phenyl]ethyl]benzenesulfonamide (Compound 17)

5-Cyano-N-[2-(2-hydrazinocarbonylmethoxy-4-isopropylphenyl)ethyl]-2-hydroxybenzenesulfonamide (0.258 g) was dissolved in 10 mL of tetrahydrofuran. To the stirred solution was added 0.177 g of triphosgene under ice-cooling, and the mixture was stirred at room temperature for 30 minutes. To the reaction mixture was added water, and the mixture was extracted with ethyl acetate. The organic layer was washed with brine, and dried over anhydrous magnesium sulfate. The solvent was removed under reduced pressure to give 0.26 g of 5-cyano-2-hydroxy-N-[2-[4-isopropyl-2-(5-oxo-4,5-dihydro[1,3,4]-oxadiazol-2-ylmethoxy)phenyl]ethyl]benzenesulfonamide.

$^1$H-NMR (CDCl$_3$) δ ppm: 1.23 (6H, d, J=6.9 Hz), 2.74–2.91 (3H, m), 3.18–3.24 (2H, m), 4.96 (2H, s), 5.50–5.55 (1H, m), 6.70–6.71 (1H, m), 6.81–6.85 (1H, m), 6.99 (1H, d, J=8.5 Hz), 7.07 (1H, d, J=8.5 Hz), 7.64 (1H, dd, J=8.8, 1.9 Hz), 7.92 (1H, d, J=1.9 Hz), 9.17–9.57 (2H, m)

Example 7

5-Cyano-2-hydroxy-N-[2-(2-hydroxy-4-isopropylphenyl)-ethyl]benzenesulfonamide (Compound 18)

To a stirred solution of 0.203 g of N-[2-(2-benzyloxy-4-isopropylphenyl)ethyl]-5-cyano-2-hydroxybenzenesulfonamide in ethanol was added 0.04 g of 10% palladium on carbon, and the mixture was stirred under a hydrogen atmosphere and ordinary pressure for 3 hours. After the insoluble material was removed by filtration, the filtrate was concentrated under reduced pressure to give 0.143 g of 5-cyano-2-hydroxy-N-[2-(2-hydroxy-4-isopropylphenyl) ethyl]benzenesulfonamide.

$^1$H-NMR (CDCl$_3$) δ ppm: 1.21 (6H, d, J=7.3 Hz), 2.71–2.86 (3H, m), 3.22–3.32 (2H, m), 6.59 (1H, s), 6.72 (1H, d, J=7.6 Hz), 6.89 (1H, d, J=7.6 Hz), 7.02 (1H, d, J=8.5 Hz), 7.59–7.64 (1H, m), 7.85–7.89 (1H, m)

Example 8

Ethyl[4-[2-(5-carbamimidoyl-2-hydroxybenzenesulfonyl-amino)ethyl]-2'-methanesulfonylbiphenyl-3-yloxy]acetate (Compound 19)

A suspension of 149 mg of ethyl[4-[2-(5-cyano-2-hydroxybenzenesulfonylamino)ethyl]-2'-methanesulfonylbiphenyl-3-yloxy]acetate in 1.0 mL of saturated hydrogen chloride ethanol solution was stirred at room temperature for 3 hours, and the reaction mixture was concentrated under reduced pressure. To a solution of the residue in 1.0 mL of ethanol was added 206 mg of ammonium acetate, and the mixture was stirred at room temperature for 13 hours. The reaction mixture was concentrated under reduced pressure to give white solid, which was triturated successively with water, and ethyl acetate-ethanol to give 141 mg of ethyl [4-[2-(5-carbamimidoyl-2-hydroxybenzene-sulfonylamino) ethyl]-2'-methanesulfonylbiphenyl-3-yloxy]-acetate as a white powder.

$^1$H-NMR (DMSO-d$_6$) δ ppm: 1.13 (3H, t, J=7.3 Hz), 2.72 (3H, s), 2.75–2.85 (2H, m), 2.90–3.00 (2H, m), 4.09 (2H, q, J=7.3 Hz), 4.76 (2H, s), 6.43 (1H, d, J=8.9 Hz), 6.90–6.95 (2H, m), 7.20 (1H, d, J=7.9 Hz), 7.39 (1H, dd, J=7.6, 1.3 Hz), 7.57 (1H, dd, J=8.9, 2.3 Hz), 7.65 (1H, td, J=7.6, 1.3 Hz), 7.74 (1H, td, J=7.6, 1.3 Hz), 7.85–8.15 (4H, m), 8.45–8.80 (2H, br)

Example 9

Ethyl[2-[2-(5-carbamimidoyl-2-hydroxybenzenesulfonylamino)ethyl]-5-isopropylphenoxy]acetate (Compound 20)

A solution of 16.09 g of ethyl[2-[2-(5-cyano-2-hydroxybenzenesulfonylamino)ethyl]-5-isopropylphenoxy]acetate in 200 mL of 37% hydrogen chloride ethanol solution was stirred at room temperature for 4 hours, and the reaction mixture was concentrated under reduced pressure. To a stirred solution of the residue in 180 ml of ethanol was added 27.78 g of ammonium acetate under ice-cooling, and the mixture was stirred at room temperature for 18 hours. The reaction mixture was concentrated under reduced pressure, and 10 mL of ethyl acetate, 200 mL of water, and 40 mL of hexane were added successively to the residue. The precipitates were collected by filtration, and washed successively with 1000 mL of water and a mixture of 80 mL of hexane and 20 mL of ethyl acetate to give 15.11 g of ethyl[2-[2-(5-carbamimidoyl-2-hydroxybenzenesulfonylamino)-ethyl]-5-isopropylphenoxy]acetate.

$^1$H-NMR (DMSO-d$_6$) δ ppm: 1.15 (6H, d, J=6.9 Hz), 1.17 (3H, t, J=7.3 Hz), 2.65–2.75 (2H, m), 2.75–2.90 (3H, m), 4.13 (2H, q, J=7.3 Hz), 4.75 (2H, s), 6.27 (1H, d, J=9.1 Hz), 6.67 (1H, d, J=1.1 Hz), 6.70–6.85 (2H, m), 7.00 (1H, d, J=7.3 Hz), 7.50 (1H, dd, J=9.1, 2.6 Hz), 7.85 (2H, br s), 7.95 (1H, d, J=2.6 Hz), 8.47 (1H, br s)

Example 10

The following compounds were prepared according to a similar manner to that described in Example 8 or 9.

Ethyl[4-[2-(5-carbamimidoyl-2-hydroxybenzenesulfonylamino)ethyl]-3',4',5'-trifluorobiphenyl-3-yloxy]acetate (Compound 21)

$^1$H-NMR (DMSO-d$_6$) δ ppm: 1.18 (3H, t, J=7.3 Hz), 2.77 (2H, t, J=6.9 Hz), 2.87 (2H, t, J=6.9 Hz), 4.13 (2H, q, J=7.3 Hz), 4.93 (2H, s), 6.26 (1H, d, J=9.1 Hz), 6.80–6.90 (1H, br s), 7.20–7.30 (3H, m), 7.50 (1H, dd, J=9.1, 2.8 Hz), 7.65–7.75 (2H, m), 7.90–8.35 (4H, m)

Ethyl 3-[2-[4-[2-(5-carbamimidoyl-2-hydroxybenzenesulfonylamino)ethyl]-3',4',5'-trifluorobiphenyl-3-yloxy]acetylamino]propionate (Compound 22)

$^1$H-NMR (DMSO-d$_6$) δ ppm: 1.14 (3H, t, J=7.3 Hz), 2.75–2.95 (4H, m), 3.44 (2H, q, J=6.0 Hz), 4.02 (2H, q, J=7.3 Hz), 4.62 (2H, s), 6.29 (1H, d, J=9.1 Hz), 6.86 (1H, br s), 7.15–7.30 (3H, m), 7.51 (1H, dd, J=9.1, 2.8 Hz), 7.65–7.75 (2H, m), 7.86 (1.5H, br s), 7.96 (1H, d, J=2.8 Hz), 8.12 (1H, t, J=6.0 Hz), 8.51 (1.5H, br s)

Methyl 4'-[2-(5-carbamimidoyl-2-hydroxybenzenesulfonyl-amino)ethyl]-3'-ethoxycarbonylmethoxybiphenyl-2-carboxylate (Compound 23)

$^1$H-NMR (DMSO-d$_6$) δ ppm: 1.17 (3H, t, J=6.9 Hz), 2.77 (2H, t, J=7.3 Hz), 2.89 (2H, t, J=7.3 Hz), 3.58 (3H, s), 4.14 (2H, q, J=6.9 Hz), 4.32–4.38 (1H, br), 4.78 (2H, s), 6.30 (1H, d, J=9.5 Hz), 6.73 (1H, d, J=1.6 Hz), 6.80 (1H, dd, J=7.9, 1.6 Hz), 7.16 (1H, d, J=7.9 Hz), 7.35–7.55 (3H, m), 7.59 (1H, td, J=7.9, 1.3 Hz), 7.68 (1H, dd, J=7.9, 1.3 Hz), 7.85 (1.5H, br s), 7.97 (1H, d, J=2.8 Hz), 8.50 (1.5H, br s)

Ethyl[2-[2-[2-(5-carbamimidoyl-2-hydroxybenzenesulfonylamino)ethyl]-5-isopropylphenoxy]acetylamino]acetate (Compound 24)

$^1$H-NMR (DMSO-d$_6$) δ ppm: 1.17 (6H, d, J=7.3 Hz), 1.20 (3H, t, J=7.3 Hz), 2.70–2.75 (2H, m), 2.78–2.85 (3H, m), 3.97 (2H, d, J=5.4 Hz), 4.11 (2H, q, J=7.3 Hz), 4.52 (2H, s), 6.27 (1H, d, J=9.1 Hz), 6.75–6.81 (3H, m), 7.04 (1H, d, J=8.2 Hz), 7.50 (1H, dd, J=9.1, 2.5 Hz), 7.86 (2H, br s), 7.94 (1H, d, J=2.5 Hz), 8.43–8.53(3H, m)

Acetic Acid Salt of 2-[2-[2-(5-carbamimidoyl-2-hydroxybenzenesulfonylamino)-ethyl]-5-isopropylphenoxy]acetamide (Compound 25)

$^1$H-NMR (DMSO-d$_6$) δ ppm: 1.16 (6H, d, J=6.9 Hz), 1.89 (3H, s), 2.68–2.74 (2H, m), 2.77–2.84 (3H, m), 4.39 (2H, s), 6.30 (1H, d, J=9.5 Hz), 6.71 (1H, d, J=1.3 Hz), 6.76 (1H, dd, J=7.6, 1.3 Hz), 7.02 (1H, d, J=7.6 Hz), 7.42–7.48 (3H, m), 7.50 (1H, dd, J=9.5, 2.5 Hz), 7.94 (1H, d, J=2.5 Hz), 7.95–8.68 (4H, m)

4-Hydroxy-3-[2-[4-isopropyl-2-(5-oxo-4,5-dihydro[1,3,4]-oxadiazol-2-ylmethoxy)phenyl]ethylsulfamoyl]benzamidine hydrochloride (Compound 26)

$^1$H-NMR (DMSO-d$_6$) δ ppm: 1.16 (6H, d, J=6.9 Hz), 2.61–2.67 (2H, m), 2.77–2.86 (1H, m), 2.92–3.02 (2H, m), 5.01 (2H, s), 6.77 (1H, dd, J=7.9, 1.3 Hz), 6.92 (1H, d, J=1.3 Hz), 6.99 (1H, d, J=7.9 Hz), 7.20 (1H, d, J=8.5 Hz), 7.39 (1H, t, J=6.0 Hz), 7.88 (1H, dd, J=8.5, 2.5 Hz), 8.14 (1H, d, J=2.5 Hz), 8.87 (2H, br s), 9.24 (2H, br s), 12.01 (1H, br s), 12.51 (1H, br s)

Ethyl 4-[2-[2-(5-carbamimidoyl-2-hydroxybenzenesulfonylamino)ethyl]-5-isopropylphenoxy]butyrate hydrochloride (Compound 27)

$^1$H-NMR (DMSO-d$_6$) δ ppm: 1.16 (6H, d, J=6.6 Hz), 1.17 (3H, t, J=7.3 Hz), 1.87–1.95 (2H, m), 2.45 (2H, t, J=7.3 Hz), 2.60–2.66 (2H, m), 2.75–2.85 (1H, m), 2.92–3.00 (2H, m), 3.92 (2H, t, J=6.3 Hz), 4.06 (2H, q, J=7.3 Hz), 6.66–6.71 (1H, m), 6.72–6.76 (1H, m), 6.94 (1H, d, J=7.9 Hz), 7.19 (1H, d, J=8.8 Hz), 7.37 (1H, t, J=5.7 Hz), 7.87 (1H, dd, J=8.8, 2.5 Hz), 8.15 (1H, d, J=2.5 Hz), 8.86 (2H, br s), 9.25 (2H, br s), 12.01 (1H, br s)

4-Hydroxy-3-[2-(2-hydroxy-4-isopropylphenyl)ethylsulfamoyl]benzamidine (Compound 28)

$^1$H-NMR (DMSO-d$_6$) δ ppm: 1.13 (6H, d, J=6.9 Hz), 2.56–2.62 (2H, m), 2.66–2.81 (3H, m), 6.27 (1H, d, J=9.1 Hz), 6.56 (1H, dd, J=7.6, 1.6 Hz), 6.61 (1H, d, J=1.6 Hz), 6.89 (1H, d, J=7.6 Hz), 7.49 (1H, dd, J=9.1, 2.8 Hz), 7.79 (2H, br s), 7.93 (1H, d, J=2.8 Hz), 8.46 (2H, br s)

Ethyl 2-[2-[2-(5-carbamimidoyl-2-hydroxybenzenesulfonylamino)ethyl]-5-isopropylphenoxy]propionate (Compound 29)

$^1$H-NMR (DMSO-d$_6$) δ ppm: 1.09–1.14 (9H, m), 1.45 (3H, d, J=6.6 Hz), 2.61–2.88 (5H, m), 4.09 (2H, q, J=6.9 Hz), 4.88 (1H, q, J=6.6 Hz), 6.27 (1H, d, J=9.1 Hz), 6.58 (1H, d, J=1.6 Hz), 6.72 (1H, dd, J=7.9, 1.6 Hz), 7.00 (1H, d, J=7.9 Hz), 7.42 (1H, d, J=9.1, 2.8 Hz), 7.93 (1H, d, J=2.8 Hz)

2-[2-[2-(5-Carbamimidoyl-2-hydroxybenzenesulfonylamino)-ethyl]-5-isopropylphenoxy]-N,N-dimethylacetamide (Compound 30)

$^1$H-NMR (DMSO-d$_6$) δ ppm: 1.15 (6H, d, J=6.9 Hz), 2.62–2.70 (2H, m), 2.73–2.85 (6H, m), 2.98 (3H, s), 4.73 (2H, s), 6.26 (1H, d, J=9.5 Hz), 6.70–6.74 (2H, m), 6.85 (1H, brs), 6.99 (1H, d, J=8.4 Hz), 7.49 (1H, dd, J=9.5, 3.2 Hz), 7.92 (1H, d, J=3.2 Hz), 8.32 (2H, br s), 8.94 (2H, br s)

4-Hydroxy-3-[2-[4-isopropyl-2-(2-morpholin-4-yl-2-oxoethoxy)phenyl]ethylsulfamoyl]benzamidine (Compound 31)

$^1$H-NMR (DMSO-d$_6$) δ ppm: 1.15 (6H, d, J=6.9 Hz), 2.60–2.70 (2H, m), 2.73–2.88 (3H, m), 3.39–3.59 (8H, m), 4.31–4.36 (1H, m), 4.76 (2H, s), 6.26 (1H, d, J=9.5 Hz), 6.69–6.76 (2H, m), 6.82 (1H, br s), 7.00 (1H, d, J=8.2 Hz), 7.49 (1H, dd, J=9.5, 2.5 Hz), 7.68–8.62 (4H, m)

Acetic Acid Salt of ethyl[4-[2-(5-carbamimidoyl-2-hydroxybenzenesulfonylamino)ethyl]-2'-sulfamoylbiphenyl-3-yloxy]-acetate (Compound 32)

$^1$H-NMR (DMSO-d$_6$) δ ppm: 1.12 (3H, t, J=7.3 Hz), 1.90 (3H, s), 2.80 (2H, t, J=6.3 Hz), 2.90–3.00 (2H, m), 4.01 (2H, q, J=7.3 Hz), 4.53 (2H, s), 6.42 (1H, d, J=9.1 Hz), 6.91(1H, dd, J=7.6, 1.6 Hz), 6.98 (1H, d, J=1.6 Hz), 7.15 (1H, d, J=7.6 Hz), 7.30 (1H, dd, J=7.6, 1.3 Hz), 7.50–7.57 (2H, m), 7.61 (1H, td, J=7.6, 1.3 Hz), 7.69 (2H, br s), 7.96 (1H, d, J=2.8 Hz), 8.06 (1H, dd, J=7.6, 1.3 Hz), 8.10–8.25 (1.5H, br), 8.40–8.60 (1.5H, br)

Example 11

[4-[2-(5-Carbamimidoyl-2-hydroxybenzenesulfonylamino)-ethyl]-2'-methanesulfonoylbiphenyl-3-yloxy]acetic acid hydrochloride (Compound 33)

To a solution of 290 mg of ethyl[4-[2-(5-carbamimidoyl-2-hydroxybenzenesulfonylamino)ethyl]-2'-methanesulfonoylbiphenyl-3-yloxy]acetate in 1.0 mL of acetonitrile was added 0.756 mL of 2 mol/L sodium hydroxide solution, and the mixture was stirred at room temperature for 30 minutes. To the reaction mixture was added 1.26 mL of 2 mol/L hydrochloric acid, and the mixture was concentrated under reduced pressure. To the residue was added water, and the mixture was purified by column chromatography on trimethylaminopropylated silica gel (eluent: 10% 1mol/L hydrochloric acid-acetonitrile). The eluent was concentrated under reduced pressure to give 260 mg of [4-[2-(5-carbamimidoyl-2-hydroxybenzenesulfonylamino)-ethyl]-2'-methanesulfonoylbiphenyl-3-yloxy]acetic acid hydrochloride as a white solid.

$^1$H-NMR (DMSO-d$_6$) δ ppm: 2.73 (3H, s), 2.80 (2H, t, J=7.3 Hz), 3.10 (2H, t, J=7.3 Hz), 4.65 (2H, s), 6.85–6.95 (2H, m), 7.16 (1H, d, J=7.6 Hz), 7.23 (1H, d, J=8.3 Hz), 7.37(1H, dd, J=7.3, 1.3 Hz), 7.66 (1H, td, J=7.6, 1.3 Hz), 7.75 (1H, td, J=7.6, 1.3 Hz), 7.89 (1H, dd, J=8.3, 2.1 Hz) 8.08 (1H, dd, J=7.9, 1.3 Hz), 8.17(1H, d, J=2.1 Hz), 8.91 (2H, br s), 9.28 (2H, br s)

Example 12

The following compounds were prepared according to a similar manner to that described in Example 11.

[4-[2-(5-Carbamimidoyl-2-hydroxybenzenesulfonylamino)-ethyl]-3',4',5'-trifluorobiphenyl-3-yloxy]acetic acid hydrochloride (Compound 34)

$^1$H-NMR (DMSO-d$_6$) δ ppm: 2.76 (2H, t, J=7.3 Hz), 3.00–3.15 (2H, m), 4.82 (2H, s), 7.10–7.25 (4H, m), 7.35–7.45 (1H, br s), 7.65–7.75 (2H, m), 7.87 (1H, dd, J=8.6, 2.1 Hz), 8.14 (1H, d, J=2.1 Hz), 8.89 (2H, br s), 9.27 (2H, br s), 11.70–12.40 (1H, br), 12.60–13.30 (1H, br)

3-[2-[4-[2-(5-Carbamimidoyl-2-hydroxybenzene-sulfonylamino)-ethyl]-3',4',5'-trifluorobiphenyl-3-yloxy]acetylamino]-propionic acid (Compound 35)

$^1$H-NMR (DMSO-d$_6$) δ ppm: 2.45 (2H, t, J=6.0 Hz), 2.75–2.90 (4H, m), 3.41 (2H, q, J=6.0 Hz), 4.56 (2H, s), 6.55 (1H, d, J=8.8 Hz), 7.20–7.30 (3H, m), 7.61 (1H, dd, J=8.8, 2.8 Hz), 7.70–7.80 (2H, m), 7.89 (1H, t, J=6.0 Hz), 8.00 (1H, d, J=2.8 Hz), 8.17 (1.5H, br s), 8.77 (1.5H, br s)

Methyl 4'-[2-(5-carbamimidoyl-2-hydroxybenzene-sulfonylamino)ethyl]-3'-carboxymethoxybiphenyl-2-carboxylate hydrochloride (Compound 36)

$^1$H-NMR (DMSO-d$_6$) δ ppm: 2.77 (2H, t, J=7.3 Hz), 3.08 (2H, t, J=7.3 Hz), 3.59 (3H, s), 4.64 (2H, s), 6.71 (1H, d, J=1.6 Hz), 6.78 (1H, dd, J=7.6, 1.6 Hz), 7.10–7.20 (2H, m), 7.40 (1H, d, J=7.3 Hz), 7.47 (1H, d, J=7.6, 1.3 Hz), 7.60 (1H, td, J=7.3, 1.3 Hz), 7.68 (1H, dd, J=7.6, 1.3 Hz), 7.86 (1H, dd, J=8.5, 2.2 Hz), 8.15 (1H, d, J=2.2 Hz), 8.82 (2H, br s), 9.25 (2H, br s)

[2-[2-(5-Carbamimidoyl-2-hydroxybenzenesulfony-lamino)-ethyl]-5-isopropylphenoxy]acetic acid hydrochloride (Compound 37)

$^1$H-NMR (DMSO-d$_6$) δ ppm: 1.14 (6H, d, J=6.9 Hz), 2.68 (2H, t, J=7.6 Hz), 2.78 (1H, sept, J=6.9 Hz), 2.95–3.05 (2H, m), 4.64 (2H, s), 6.65–6.70 (1H, m), 6.72 (1H, dd, J=7.8, 1.2 Hz), 6.97 (1H, d, J=7.8 Hz), 7.25 (1H, d, J=8.4 Hz), 7.30–7.45 (1H, m), 7.90 (1H, dd, J=8.4, 2.8 Hz), 8.15 (1H, dd, J=2.8 Hz), 8.99 (2H, br s), 9.29 (2H, s), 12.13 (1H, br s), 12.94 (1H, br s)

[2-[2-[2-(5-Carbamimidoyl-2-hydroxybenzenesulfo-nylamino)-ethyl]-5-isopropylphenoxy]acetylamino] acetic acid (Compound 38)

$^1$H-NMR (DMSO-d$_6$) δ ppm: 1.16 (6H, d, J=6.9 Hz), 2.72–2.77 (2H, m), 2.78–2.86 (3H, m), 3.79 (2H, d, J=5.7 Hz), 4.47 (2H, s), 6.54 (1H, d, J=9.1 Hz), 6.76 (1H, dd, J=7.6, 1.3 Hz), 6.78–6.79 (1H, m), 7.03 (1H, d, J=7.6 Hz) 7.59 (1H, dd, J=9.1, 2.5 Hz), 7.99 (1H, d, J=2.5 Hz), 8.09–8.21 (3H, m), 8.70–8.86 (2H, m)

4-[2-[2-(5-Carbamimidoyl-2-hydroxybenzenesulfo-nylamino)-ethyl]-5-isopropylphenoxy]butyric acid (Compound 39)

$^1$H-NMR (DMSO-d$_6$) δ ppm: 1.15 (6H, d, J=7.3 Hz), 1.85–1.98 (2H, m), 2.42 (2H, t, J=7.3 Hz), 2.59–2.69 (2H, m), 2.72–2.86 (3H, m), 3.90 (2H, t, J=6.0 Hz), 6.68 (1H, d, J=7.6 Hz), 6.72 (1H, s.), 6.80 (1H, d, J=8.5 Hz), 6.97 (1H, d, J=7.6 Hz), 7.66–7.77 (1H, m), 8.00–8.11 (1H, m), 8.49 (2H, br s), 8.93 (2H, br s)

2-[2-[2-(5-Carbamimidoyl-2-hydroxybenzenesulfo-nylamino)-ethyl]-5-isopropylphenoxy]propionic acid hydrochloride (Compound 40)

$^1$H-NMR (DMSO-d$_6$) δ ppm: 1.09–1.16 (6H, m), 1.43 (3H, d, J=6.6 Hz), 2.56–2.81 (3H, m), 2.91–3.08 (2H, m), 4.77 (1H, q, J=6.6 Hz), 6.59 (1H, s), 6.70 (1H, d, J=7.9 Hz), 6.96 (1H, d, J=7.9 Hz), 7.23 (1H, d, J=8.8 Hz), 7.35 (1H, br s), 7.89 (1H, d, J=8.8, 2.5 Hz), 8.15 (1H, d, J=2.5 Hz), 8.96 (2H, br s), 9.28 (2H, br s), 12.12 (1H, br s), 12.95 (1H, br s)

[4-[2-(5-Carbamimidoyl-2-hydroxybenzenesulfony-lamino)-ethyl]-2'-sulfamoylbiphenyl-3-yloxy]acetic acid hydrochloride (Compound 41)

$^1$H-NMR (DMSO-d$_6$) δ ppm: 2.75–2.85 (2H, m), 3.05–3.15 (2H, m), 4.63 (2H, s), 6.87 (1H, d, J=1.6 Hz), 6.91 (1H, dd, J=7.6, 1.6 Hz), 7.05–7.12 (3H, m), 7.20 (1H, d, J=8.5 Hz), 7.29 (1H, dd, J=7.6, 1.3 Hz), 7.40–7.50 (1H, br s), 7.55 (1H, td, J=7.6, 1.3 Hz), 7.61 (1H, td, J=7.6, 1.3 Hz), 7.88 (1H, dd, J=8.5, 2.5 Hz), 8.02 (1H, dd, J=7.6, 1.3 Hz), 8.17 (1H, d, J=2.5 Hz), 8.83 (2H, br s), 9.26 (2H, br s), 12.00 (1H, br s), 12.90 (1H, br s)

Example 13

[2-[2-(5-Carbamimidoyl-2-hydroxybenzenesulfony-lamino)-ethyl]-5-isopropylphenoxy]acetic acid (Co-mopound 42)

Ethyl[2-[2-(5-carbamimidoyl-2-hydroxybenzenesulfony-lamino)ethyl]-5-isopropylphenoxy]acetate (50 mg) was dissolved in a mixture of 3 mL of 1 mol/L hydrochloric acid and 1 mL of acetonitrile at 60° C. The solution was stirred at 60° C. for 4 hours, and the colorless solid obtained by concentration under reduced pressure of the reaction mixture was dissolved in a mixture of 3 mL of 1 mol/L hydrochloric acid and 1 mL of acetnitrile at 60° C. After the solution was stirred at 60° C. for 4 hours, then at room temperature for 10 hours, the reaction mixture was concentrated under reduced pressure to give a colorless solid. The solid was triturated with water and diethyl ether, and collected by filtration to give 31 mg of [2-[2-(5-carbamimidoyl-2-hydroxybenzene-sulfonylamino)-ethyl]-5-isopropylphenoxy]acetic acid.

$^1$H-NMR (DMSO-d$_6$) δ ppm: 1.15 (6H, d, J=6.9 Hz), 2.61–2.83 (3H, m), 3.05 (2H, t, J=7.6 Hz), 4.42 (2H, s), 6.67 (1H, s), 6.69 (1H, d, J=7.5 Hz), 6.82 (1H, d, J=9.1 Hz), 6.98(1H, d, J=7.5 Hz), 7.69 (1H, dd, J=9.1, 2.5 Hz), 8.05 (1H, d, J=2.5 Hz), 8.56 (2H, br s), 8.94 (2H, br s)

Example 14

Ethyl[4-[2-[2-hydroxy-5-(N-hydroxycarbamim-idoyl)-benzenesulfonylamino]ethyl]-2'-mthanesulfo-nylbiphenyl-3-yloxy]acetate (Compound 43)

A suspension of 2.01 g of ethyl [4-[2-(5-cyano-2-hy-droxybenzenesulfonylamino)ethyl-2'-methanesulfonylbi-phenyl-3-yloxy]acetate in 1.0 mL of saturated hydrogen chloride ethanol solution was stirred at room temperature for 3 hours. The reaction mixture was concentrated under reduced pressure, and the residue was dissolved in 20.0 mL of ethanol. To this solution was added 3.34 g of hydroxy-lammonium acetate, and the mixture was stirred at room temperature for 13 hours. The reaction mixture was poured into ethyl acetate-water, and the organic layer was separated. After the aqueous layer was extracted with ethyl acetate, and the organic layers were combined, and washed with brine. The organic layer was dried over anhydrous magnesium sulfate, and filtered. The filtrate was concentrated under reduced pressure, and the residue was purified by column chromatography on silica gel (eluent: ethyl acetate) to give 1.90 g of ethyl [4-[2-[2-hydroxy-5-(N-hydroxycarbamim-idoyl)-benzenesulfonylamino]ethyl]-2'-methanesulfonylbi-phenyl-3-yloxy]acetate, amorphous.

$^1$H-NMR (DMSO-d$_6$) δ ppm: 1.12 (3H, t, J=6.9 Hz), 2.70 (3H, s), 2.75–2.85 (2, m), 3.00–3.10 (2H, m), 4.08 (2H, q, J=6.9 Hz), 4.75 (2H, s), 5.77 (2H, br s), 6.85–6.95 (2H, m), 6.97 (1H, d, J=8.5 Hz), 7.10–7.25 (2H, m), 7.35–7.40 (1H, m) 7.60–7.80 (3H, m), 7.95–8.10 (2H, m), 9.53 (1H, br s), 10.9 (1H, br s)

Example 15

The following compound was prepared according to a similar manner to that described in Example 14.

Ethyl[2-[2-[2-hydroxy-5-(N-hydroxycarbamimidoyl)-benzenesulfonylamino]ethyl]-5-isopropylphenoxy]acetate (Compound 44)

$^1$H-NMR (DMSO-$d_6$) δ ppm: 1.13 (6H, d, J=6.9 Hz), 1.16 (3H, t, J=7.3 Hz), 2.65–2.71 (2H, m), 2.73–2.84 (1H, m), 2.93–3.00 (2H, m), 4.12 (2H, q, J=7.3 Hz), 4.73 (2H, s), 5.77 (2H, br s), 6.65 (1H, d, J=1.3 Hz), 6.72 (1H, dd, J=7.9, 1.3 Hz), 6.95 (1H, d, J=8.5 Hz), 6.96 (1H, d, J=7.9 Hz), 7.08 (1H, br s), 7.69 (1H, dd, J=8.5, 2.2 Hz), 7.99 (1H, d, J=2.2 Hz), 9.53 (1H, br s), 10.85 (1H, br s)

Example 16

[4-[2-(5-Cyano-2-hydroxybenzenesulfonylamino)ethyl]-2'-methanesulfonylbiphenyl-3-yloxy]acetic acid (Compound 45)

To a stirred solution of 154 g of ethyl[4-[2-(5-cyano-2-hydroxybenzenesulfonylamino)ethyl]-2'-methanesulfonylbiphenyl-3-yloxy]acetate in 1.23 L of ethanol was added 275 mL of 2mol/L sodium hydroxide solution under ice-cooling, and the mixture was stirred under ice-cooling for 1.5 hours. To the reaction mixture was added dropwise 275 mL of 2 mol/L hydrochloric acid, and ethanol was removed under reduced pressure. The residue was extracted with ethyl acetate, and the organic layer was washed with brine. The solvent was dried over anhydrous magnesium sulfate, and removed under reduced pressure to give 149 g of [4-[2-(5-cyano-2-hydroxybenzenesulfonylamino)-ethyl]-2'-methanesulfonylbiphenyl-3-yloxy)acetic acid.

$^1$H-NMR (DMSO-$d_6$) δ ppm: 2.73 (3H, s), 2.75–2.85 (2H, m), 3.05–3.20 (2H, m), 4.66 (2H, s), 6.85–6.95 (2H, m), 7.13 (1H, d, J=8.5 Hz), 7.17 (1H, d, J=7.6 Hz), 7.39 (1H, dd, J=7.5, 1.3 Hz), 7.50–7.60 (1H, m), 7.60–7.70 (1H, m), 7.88 (1H, dd, J=8.5, 2.1 Hz), 8.02 (1H, d, J=2.1 Hz), 8.08 (1H, dd, J=8.0, 1.3 Hz), 11.80–12.20 (1H, br), 12.70–13.30 (1H, br)

Example 17

Sodium[4-[2-(5-cyano-2-hydroxybenzenesulfonylamino)-ethyl]-2'-methanesulfonylbiphenyl-3-yloxy]acetate (Compound 46)

To a stirred solution of 146 g of [4-[2-(5-cyano-2-hydroxybenzenesulfonylamino)ethyl]-2'-methanesulfonyl-biphenyl-3-yloxy]acetic acid in 580 mL of ethanol was added 137 mL of 2mol/L sodium hydroxide solution under ice-cooling, and the solvent was removed under reduced pressure. The residue was suspended with 1.16 L of ethanol, and the mixture was stirred under reflux for an hour, then at room temperature overnight. The obtained white solid was collected by filtration to give 129 g of sodium[4-[2-(5-cyano-2-hydroxybenzenesulfonyl-amino)ethyl]-2'-methanesulfonylbiphenyl-3-yloxy]acetate.

$^1$H-NMR (DMSO-$d_6$) δ ppm: 2.71 (3H, s), 2.75–2.85 (2H, m), 3.10–3.25 (2H, m), 4.39 (2H, s), 6.73 (1H, d, J=8.5 Hz), 6.80–6.90 (2H, m), 7.17 (1H, d, J=8.2 Hz), 7.40 (1H, dd, J=7.6, 1.3 Hz), 7.49 (1H, dd, J=8.8, 2.2 Hz), 7.60–7.70 (1H, m), 7.70–7.80 (2H, m), 8.08 (1H, dd, J=8.2, 1.3 Hz)

Example 18

[4-[2-[2-Hydroxy-5-(N-hydroxycarbamimidoyl)benzenesulfonyl-amino]ethyl]-2'-methanesulfonylbiphenyl-3-yloxy]acetic acid (Compound 47)

Method 1) To a suspension of 79 mg of ethyl[4-[2-[2-hydroxy-5-(N-hydroxycarbamimidoyl)benzenesulfonylamino]-ethyl]-2'-methanesulfonylbiphenyl-3-yloxy]acetate in acetonitrile was added 0.401 mL of 1 mol/L sodium hydroxide solution, and the mixture was stirred at room temperature for 30 minutes. To the reaction mixture was added 0.401 mL of 1 mol/L hydrochloric acid, and the mixture was concentrated under reduced pressure. To the residue was added water, and the mixture was purified by column chromatography on trimethylamino-propylated silica gel (eluent: 10% 1 mol/L hydrochloric acid-acetonitrile). The eluent was concentrated under reduced pressure, and the residue was triturated with ethyl acetate to collect by filtration of 70 mg of [4-[2-[2-hydroxy-5-(N-hydroxycarbamimidoyl)-benzenesulfonylamino]ethyl]-2'-methanesulfonylbiphenyl-3-yloxy]acetic acid as an yellow powder.

Method 2) To a stirred solution of 117 g of sodium[4-[2-(5-cyano-2-hydroxybenzenesulfonylamino)ethyl]-2'-methanesulfonylbiphenyl-3-yloxy]acetate in 1.17 L of water was added 56 g of 50% aqueous hydroxylamine solution at room temperature, and the mixture was stirred at 70° C. for 4 hours. To the reaction mixture was added dropwise 1 mol/L hydrochloric acid at room temperature, and the mixture was stirred at the same temperature over night. The obtained solid was collected by filtration to give 110 g of [4-[2-[2-hydroxy-5-(N-hydroxy-carbamimidoyl)benzenesulfonylamino]ethyl]-2'-methane-sulfonylbiphenyl-3-yloxy]acetic acid.

$^1$H-NMR (DMSO-$d_6$) δ ppm: 2.73 (3H, s), 2.75–2.85 (2H, m), 3.05–3.15 (2H, m), 4.67 (2H, s), 6.85–6.95 (2H, m), 7.16 (1H, d, J=7.9 Hz), 7.24 (1H, d, J=8.5 Hz), 7.35–7.50 (2H, m), 7.66 (1H, td, J=7.6, 1.3 Hz), 7.70–7.85 (2H, m), 8.00–8.10 (2H, m), 8.45–9.60 (1H, br), 10.80–13.30 (3H, br)

Example 19 n-Butyl[4-[2-[2-Hydroxy-5-(N-hydroxycarbamimidoyl)-benzenesulfonylamino]ethyl]-2'-methane-sulfonylbiphenyl-3-yloxy]acetate hydrochloride (Compound 48)

Method 1) A solution of 1.499 g of ethyl[4-[2-[2-hydroxy-5-(N-hydroxycarbamimidoyl)benzenesulfonylamino]-ethyl]-2'-methanesulfonylbiphenyl-3-yloxy]acetate in 20 mL of 34% hydrogen chloride n-butanol solution was stirred at 60° C. for 3 hours. After being concentrated under reduced pressure, the reaction mixture was recrystallized from n-butanol-diisopropyl ether to give 1.472 g of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride as a white crystal.

Method 2) A solution of 110 g of [4-[2-[2-hydroxy-5-(N-hydroxycarbamimidoyl)benzenesulfonylamino]ethyl]-2'-methanesulfonylbiphenyl-3-yloxy]acetic acid in 1.00 L of 14% hydrogen chloride n-butanol solution was stirred at 100° C. for 2.5 hours. The reaction mixture was concentrated under reduced pressure, and the residue was washed with ethyl acetate to give 111 g of crude crystal. The crude crystal was recrystallized from n-butanol-diisopropyl ether to give 83.3 g of n-butyl[4-[2-[2-hydroxy-5-(N-hydroxycarbamimidoyl)benzenesulfonylamino]ethyl]-2'-methanesulfonylbiphenyl-3-yloxy]acetate hydrochloride.

$^1$H-NMR (DMSO-$d_6$) δ ppm: 0.78 (3H, t, J=7.6 Hz), 1.15–1.30 (2H, m), 1.40–1.55 (2H, m), 2.72 (3H, s), 2.75–2.85 (2H, m), 3.05–3.15 (2H, m), 4.05 (2H, t, J=6.6 Hz), 4.78 (2H, s), 6.90–6.95 (2H, m), 7.18 (1H, d, J=7.6 Hz), 7.20–7.30 (1H, m), 7.37(1H, d, J=7.6 Hz), 7.42–7.50 (1H, m), 7.66 (1H, td, J=7.6, 1.3 Hz), 7.72–7.82 (2H, m), 8.02–8.10 (2H, m), 8.60–9.60 (1H, br), 10.85–11.30 (1H, br), 11.80–12.20 (1H, br), 12.50–13.05 (1H, br)

Example 20

The following compounds were prepared according to a similar manner to that described in Example 19.

Cyclohexyl[4-[2-[2-hydroxy-5-(N-hydroxycarbamimidoyl)-benzenesulfonylamino]ethyl]-2'-methanesulfonylbiphenyl-3-yloxy]acetate (Compound 49)

$^1$H-NMR (CDCl$_3$) δ ppm: 1.10–1.60 (6H, m), 1.64–1.74 (2H, m), 1.78–1.88 (2H, m), 2.66 (3H, s), 2.93 (2H, t, J=6.0 Hz), 3.35 (2H, t, J=6.0 Hz), 4.62 (2H, s), 4.82–4.90 (1H, m), 4.95 (2H, s), 5.90–6.05 (1H, br s), 6.85–7.00 (3H, m), 7.12 (1H, d, J=7.6 Hz), 7.36 (1H, dd, J=7.9, 1.3 Hz), 7.57 (1H, td, J=7.9, 1.3 Hz), 7.62–7.73 (2H, m), 7.96 (1H, d, J=2.2 Hz), 8.21 (1H, dd, J=7.9, 1.3 Hz)

Isopropyl[4-[2-[2-hydroxy-5-(N-hydroxycarbamimidoyl)-benzenesulfonylamino]ethyl]-2'-methanesulfonylbiphenyl-3-yloxy]acetate (Compound 50)

$^1$H-NMR (CDCl$_3$) δ ppm: 1.26 (6H, d, J=6.3 Hz), 2.65 (3H, s), 2.93 (2H, t, J=6.0 Hz), 3.30–3.40 (2H, m), 4.61 (2H, s), 4.99 (2H, br s), 5.05–5.15 (1H, m), 6.04 (1H, br s), 6.85–7.05 (3H, m), 7.12 (1H, d, J=7.6 Hz), 7.34–7.45 (1H, m), 7.50–7.80 (3H, m), 7.95–8.00 (1H, m), 8.15–8.30 (1H, m)

Example 21

Ethyl[2-[2-[(5-carbamimidoyl-2-hydroxybenzenesulfonyl)-(2-methyl-1,3-thiazole-4-ylmethyl)amino]ethyl]-5-isopropyl-phenoxy]acetate (Compound 51)

A solution of 174 mg of ethyl[2-[2-[(5-cyano-2-hydroxybenzenesulfonyl)-(2-methyl-1,3-thiazole-4-ylmethyl)amino]-ethyl]-5-isopropylphenoxy]acetate in hydrogen chloride ethanol solution was stirred at room temperature for 5 hours. The reaction mixture was concentrated under reduced pressure, and the residue was dissolved in 3 mL of ethanol. To the stirred mixture was added 135 mg of ammonium acetate under ice-cooling, and the mixture was stirred at room temperature for 2 days. To the reaction mixture was added water, and the precipitate was collected by filtration, and washed with water to give 71 mg of ethyl[2-[2-[(5-carbamimidoyl-2-hydroxybenzenesulfonyl)-(2-methyl-1,3-thiazole-4-ylmethyl)amino]ethyl]-5-isopropyl-phenoxy]acetate.

$^1$H-NMR (DMSO-$d_6$) δ ppm: 1.08–1.19 (9H, m), 2.56–2.67 (5H, m), 2.70–2.81 (1H, m), 3.25–3.33 (2H, m), 4.11 (2H, q, J=7.3 Hz), 4.63 (2H, s), 4.67 (2H, s), 6.22 (1H, d, J=9.1 Hz), 6.62 (1H, s), 6.66–6.72 (1H, m), 6.88 (1H, d, J=7.6 Hz), 7.20 (1H, s), 7.45 (1H, dd, J=9.1, 2.8 Hz), 7.54–7.96 (2H, br), 8.06 (1H, d, J=2.8 Hz), 8.14–8.67 (2H, br)

Example 22

The following compound was prepared according to a similar manner to that described in Example 21.

5-Carbamimidoyl-2-hydroxy-N-[2-(4-isopropyl-2-sulfamoylphenyl)ethyl]benzenesulfonamide (Compound 52)

$^1$H-NMR (DMSO-$d_6$) δ ppm: 1.20 (6H, d, J=6.9 Hz), 2.87–2.97 (3H, m), 3.07 (2H, t, J=7.3 Hz), 6.27 (1H, d, J=9.1 Hz), 7.00–7.65 (5H, m), 7.72 (1H, d, J=1.9 Hz), 7.75–7.90 (2H, br), 7.95 (1H, d, J=2.8 Hz), 8.40–8.60 (2H, m)

Example 23

[2-[2-[(5-Carbamimidoyl-2-hydroxybenzenesulfonyl)-(2-methyl-1,3-thiazol-4-ylmethyl)amino]ethyl]-5-isopropylphenoxy]acetic acid (Compound 53)

To a stirred solution of 100 mg of ethyl [2-[2-[(5-carbamimidoyl-2-hydroxybenzenesulfonyl)-(2-methyl-1,3-thiazol-4-ylmethyl)amino]ethyl]-5-isopropylphenoxy]acetate in 0.8 mL of ethanol was added 0.183 mL of 2 mol/L sodium hydroxide solution under ice-cooling. After being stirred at the same temperature for 30 minutes, the reaction mixture was concentrated under reduced pressure. To the stirred solution of the residue in a mixture of 0.8 mL of acetonitrile and 0.8 mL of water was added 0.174 mL of 1 mol/L hydrochloric acid under ice-cooling, and the mixture was stirred at the same temperature for 5 minutes. To the mixture was added additional 0.174 mL of 1 mol/L hydrochloric acid under ice-cooling, and the mixture was stirred at the same temperature for 5 minutes. The precipitate was collected by filtration, and washed with water to give 74 mg of [2-[2-[(5-carbamimidoyl-2-hydroxybenzenesulfonyl)-(2-methyl-1,3-thiazole-4-ylmethyl)amino]ethyl]-5-isopropylphenoxy] acetic acid.

$^1$H-NMR (DMSO-$d_6$) δ ppm: 1.15 (6H, d, J=6.9 Hz), 2.62 (3H, s), 2.73–2.84 (3H, m), 3.40–3.50 (2H, m), 4.33 (2H, s), 4.53 (2H, s), 6.66 (1H, dd, J=7.6, 1.3 Hz), 6.69 (1H, d, J=1.3 Hz), 6.83 (1H, d, J=7.6 Hz), 6.98 (1H, d, J=8.8 Hz), 7.26 (1H, s), 7.72 (1H, dd, J=8.8, 2.5 Hz), 8.12 (1H, d, J=2.5 Hz), 8.48 (2H, br s), 9.14 (2H, br s)

Example 24

Amino-[4-hydroxy-3-[[2-[4-isopropyl-2-(ethoxycarbonylmethoxy)phenyl]ethyl]sulfamoyl]phenyl]methylenecarbamoyloxymethyl 2,2-dimethylpropionate (Compound 54)

To a stirred solution of 99 mg of amino-[4-benzyloxy-3-[[2-[4-isopropyl-2-(ethoxycarbonylmethoxy)phenyl]ethyl]-sulfamoyl]phenyl]methylenecarbamoyloxymethyl 2,2-dimethylpropionate in 3 mL of tetrahydrofuran was added 9.2 mg of 10% palladium on carbon under ice-cooling, and the mixture was stirred under a hydrogen atmosphere at 30° C. for 1 hour. The insoluble material was removed by filtration, and the filtrate was concentrated under reduced pressure. The residue was purified by column chromatography on silica gel (eluent: ethyl acetate-hexane) to give 75 mg of amino-[4-hydroxy-3-[[2-[4-isopropyl-2-(ethoxycarbonylmethoxy)phenyl]ethyl]sulfamoyl]-phenyl]methylenecarbamoyloxymethyl 2,2-dimethylpropionate.

$^1$H-NMR (CDCl$_3$) δ ppm: 1.19 (6H, d, J=6.9 Hz), 1.22 (9H, s), 1.35 (3H, t, J=7.3 Hz), 2.73–2.88 (3H, m), 3.20–3.32 (2H, m), 4.32 (2H, q, J=7.3 Hz), 4.87 (2H, s), 5.86 (2H, s), 6.11 (1H, br s), 6.52 (1H, s), 6.72 (1H, d, J=7.6 Hz), 6.95

(1H, d, J=7.6 Hz), 7.01 (1H, d, J=8.8 Hz), 8.08–8.15 (1H, m), 8.20 (1H, d, J=2.2 Hz), 8.72–9.90 (2H, br)

Example 25

The following compounds were prepared according to a similar manner to that described in Example 24.

Amino-[4-hydroxy-3-[[2-[4-isopropyl-2-(ethoxycarbonylmethoxy)phenyl]ethyl]sulfamoyl]phenyl]methylenecarbamoyloxymethyl 2-acetoxy-2-methylpropionate (Compound 55)

$^1$H-NMR (CDCl$_3$) δ ppm: 1.20 (6H, d, J=6.9 Hz), 1.35 (3H, t, J=7.3 Hz), 1.57 (6H, s), 2.04 (3H, s), 2.75–2.88 (3H, m), 3.22–3.32 (2H, m), 4.32 (2H, q, J=7.3 Hz), 4.69 (2H, s), 5.89 (2H, s), 6.12 (1H, br s), 6.51–6.56 (1H, m), 6.73–6.79 (1H, m), 6.95 (1H, d, J=7.9 Hz), 7.01 (1H, d, J=8.8 Hz), 8.11 (1H, dd, J=8.8, 2.2 Hz), 8.21 (1H, d, J=2.2 Hz), 8.65–9.95 (2H, m)

Ethyl [4-[2-[5-amino(butoxycarbonylimino)methyl]-2-hydroxybenznesulfonylamino]ethyl]-2'-methanesulfonylbiphenyl-3-yl]oxyacetate (Compound 56)

$^1$H-NMR (DMSO-d$_6$) δ ppm: 0.90 (3H, t, J=7.3 Hz), 1.11 (3H, t, J=7.3 Hz), 1.31–1.40 (2H, m), 1.54–1.63 (2H, m), 2.69 (3H, s), 2.74–2.82 (2H, m), 3.02–3.11 (2H, m), 4.00 (2H, t, J=6.6 Hz), 4.05 (2H, q, J=7.3 Hz), 4.74 (2H, s), 6.88–6.92 (2H, m), 6.96–7.06 (1H, m), 7.15 (1H, d, J=7.6 Hz), 7.19–7.47 (2H, m), 7.65 (1H, td, J=7.6, 0.9 Hz), 7.74 (1H, td, J=7.6, 1.3 Hz), 8.00–8.11 (2H, m), 8.39 (1H, d, J=1.9 Hz), 8.85–9.35 (2H, m), 11.30–11.70 (1H, br)

Test Example 1

Measurement of Inhibitory Activity for Activated Blood Coagulation Factor X 2.5 µL of a dimethylsulfoxide solution of a test compound, 187.5 µL of 100 mM tris-200 mM NaCl buffer (pH 8.4) and 50 µL of 1 mM S-2222 (Daiichi Pure Chemicals) aqueous solution were poured into 96 well microplate. Then 10 µL of 0.6 U/mL human activated blood coagulation factor X (Calbiochem) in gelatin-glycine buffer was added and the mixture was incubated for 10 minutes at 37° C. The reaction was terminated with the addition of 50 µL of 60% acetic acid and absorbance (405 nm) was measured by a microplate reader (SPECTRAmax 250, Molecular Devices).

The group with 2.5 µL of the dimethylsulfoxide solution instead of the test compound solution was defined as the control, and the group with 10 µL of the gelatin-glycine buffer solution instead of human activated blood coagulation factor X was defined as the blank. The concentration of a test compound that inhibited the absorbance of control by 50% (IC$_{50}$) was obtained, and this value was used as the index of inhibitory activity for activated blood coagulation factor X. Results were shown as Table 1.

TABLE 1

| Test compound No. | Inhibitory activity for activated blood coagulation factor X (IC$_{50}$, µM) |
| --- | --- |
| Compound 33 | 0.012 |
| Compound 42 | 0.10 |
| Compound 52 | 0.016 |
| Compound 53 | 0.051 |

Test Example 2

Measurement of Inhibitory Activity for Thrombin 2.5 µL of a dimethylsulfoxide solution of a test compound, 187.5 µL of 100 mM tris-200 mM NaCl buffer (pH 8.4) and 50 µL of 1 mM S-2238 (Daiichi Pure Chemicals) aqueous solution were poured into 96 well microplate. Then 10 µL of 2.0 U/mL human thrombin (Sigma Chemical Company) in gelatin-glycine buffer was added and the mixture was incubated for 10 minutes at 37° C. The reaction was terminated with the addition of 50 µL of 60% acetic acid and absorbance (405 nm) was measured by a microplate reader (SPECTRAmax 250, Molecular Devices).

The group with 2.5 µL of the dimethylsulfoxide solution instead of the test compound solution was defined as the control, and the group with 10 µL of the gelatin-glycine buffer solution instead of human thrombin was defined as the blank. The concentration of a test compound that inhibited the absorbance of control by 50% (IC$_{50}$) was obtained, and this value was used as the index of inhibitory activity for thrombin. Results were shown as Table 2.

TABLE 2

| Test compound No. | Inhibitory activity for thrombin (IC$_{50}$, µM) |
| --- | --- |
| Compound 33 | >100 |
| Compound 42 | >100 |
| Compound 52 | >100 |
| Compound 53 | >100 |

Test Example 3

Measurement of Anticoagulation Effects (Prolongation of Plasma Prothrombin Time)

Two µL of a dimethylsulfoxide solution of a test compound was put in the process tube and then incubated at 37° C. One minute after addition of 48 µL of normal human plasma (George King Bio-Medical Inc), 100 µL of plasma prothrombin time reagent (Boehringer Mannheim) prewarmed at 37° C. was added into the mixture. Prothrombin time was measured with a coagulometer (ST4, Boehringer Mannheim).

The group without any test compound was defined as the control. The concentration of test compound that prolonged the clotting time of the control by 2 times (CT$_2$) was obtained and, this value was used as the index of anticoagulation activity. Results were shown as Table 3.

TABLE 3

| Test compound No. | Anticoagulation activity (µM) |
| --- | --- |
| Compound 33 | 0.52 |
| Compound 42 | 2.4 |

Test Example 4

Oral Administration Test in Rats

1) Collection of Plasma

Male Wistar rats aged 6–9 weeks (SLC) fasted overnight were used. A test compound was dissolved or suspended in 0.5% methylcellulose solution at the concentration of 6.0 mg/mL. Then 5.0 mL/kg of that was orally administrated into the rats. Before and at proper time points after administration of the test compound, citrated (1:10 dilution, 3.13% sodium citrate) blood was collected from the jugular vein. Plasma samples were obtained by centrifugation.

2) Measurement of Anti-Activated Blood Coagulation Factor X Activity in Plasma 2.5 μL of plasma sample, 200 μL of 100 mM tris-200 mM NaCl buffer (pH 8.4) and 10 μL of 0.06 U/mL human activated blood coagulation factor X (Calbiochem) in gelatin-glycine buffer were poured into 96 well microplate. Then 50 μL of 1 mM S-2222 (Daiichi Pure Chemicals) aqueous solution was added and the mixture was incubated for 10 minutes at room temperature. The reaction was terminated with the addition of 50 μL of 60% acetic acid and absorbance (405 nm) was measured by a microplate reader (SPECTRAmax 250, Molecular Devices).

The group with 2.5 μL of the control plasma instead of the plasma sample was defined as the control, and the group with 10 μL of gelatin-glycine buffer solution instead of human activated blood coagulation factor X was defined as the blank. The inhibitory % of plasma sample was calculated from absorbance of the control as 100% and this value was used as the index of anti-activated blood coagulation factor X activity in plasma.

3) Measurement of Prothrombin Time (PT).

Fifty μL of plasma was put in the process tube and then incubated at 37° C. One minute later, 100 μL of plasma PT reagent (Boehringer Mannheim) prewarmed at 37° C. was added into the mixture. PT was measured with a coagulometer (ST4, Boehringer Mannheim).

The ratio of PT at each time point after administration of the test compound to that of before administration was used as the index of anticoagulation activity.

4) Results of anti-activated blood coagulation factor X activity in plasma and PT ratio at 30 minutes after oral administration of each test compound at a dose of 30 mg/kg were shown as Table 4.

TABLE 4

| Test compound No. | Anti-activated blood coagulation factor X activity in plasma (%) | PT ratio |
| --- | --- | --- |
| Compound 43 | 32.0 | 1.31 |
| Compound 48 | 58.2 | 1.50 |
| Compound 49 | 51.4 | 1.43 |

Test Example 5

Acute Toxicity Test

Male ICR mice aged 7 weeks (SLC) were divided into several groups consisted of 5 mice. A solution containing a test compound was prepared at the concentration that became the administration volume of the test compound to be 50.0 mg/10.0 mL/kg. The solution was administered into tail vein at an infusion rate of 1 mL/minute. Observations were performed at constant interval, and survival rate was judged for 24 hours. Results were shown as Table 5, and no death case was observed.

TABLE 5

| Test compound No. | Death case |
| --- | --- |
| Compound 42 | 0/5 |

INDUSTRIAL APPLICABILITY

The 5-amidino-2-hydroxybenzenesulfonamide derivatives and pharmaceutically acceptable salts thereof of present inventors show a potent and selective activated blood coagulation factor X inhibitory activity. The present invention can provide novel compounds having excellent properties as activated blood coagulation factor X inhibitors. In addition, the 5-cyano-2-hydroxybenzenesulfonamide derivatives represented by the above general formulae (II) and salts thereof of the present invention are important as intermediates in the production of the compounds represented by the above general formula (I). Accordingly, the compounds represented by the above general formula (I) of the present invention can be readily prepared via these compounds.

The invention claimed is:

1. A 5-amidino-2-hydroxybenzenesulfonamide derivative represented by the general formula:

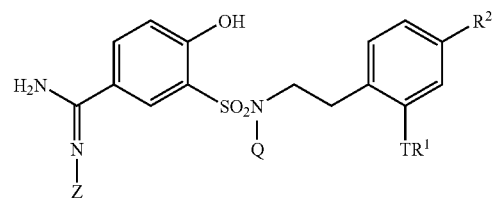

wherein $R^1$ represents a hydrogen atom or a lower alkyl group which may have a substituent selected from the following group (A);

(A) —COOR$^A$, —CONR$^B$R$^C$, a 3 to 10-membered cycloalkyl group, a 6 to 10-membered aryl group, a 3 to 10-membered heterocycloalkyl group which may have an oxo group, and a 5 to 10-membered aromatic heterocyclic group which may have an oxo group or a lower alkyl group;

wherein $R^A$ represents a hydrogen atom, a 3 to 10-membered cycloalkyl group or a lower alkyl group which may have a substituent selected from the following group (i);

(i) —COOR$^{A1}$ in which $R^{A1}$ is a hydrogen atom, a 3 to 10-membered cycloalkyl group or a lower alkyl group, —OCOR$^{A2}$ in which $R^{A2}$ is a 3 to 10-membered cycloalkyl group or a lower alkyl group, —OCOOR$^{A3}$ in which $R^{A3}$ is a 3 to 10-membered cycloalkyl group or a lower alkyl group, —OR$^{A4}$ in which $R^{A4}$ is a hydrogen atom, a 3 to 10-membered cycloalkyl group or a lower alkyl group, —CONR$^{A5}$R$^{A6}$ in which $R^{A5}$ and $R^{A6}$ are independently a hydrogen atom or a lower alkyl group, or —NR$^{A5}$R$^{A6}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

wherein $R^B$ and $R^C$ independently represent a hydrogen atom or a lower alkyl group which may have a substituent selected from the following group (ii), or —NR$^B$R$^C$ forms a cyclic amino group;

(ii) —COOR$^{B1}$ in which $R^{B1}$ is a hydrogen atom, a 3 to 10-membered cycloalkyl group or a lower alkyl group, —CONR$^{B2}$R$^{C2}$ in which $R^{B2}$ and $R^{C2}$ are independently a hydrogen atom or a lower alkyl group, or —NR$^{B2}$R$^{C2}$ forms a cyclic amino group, a 3 to 10-membered cycloalkyl group, a 6 to 10-membered aryl group, a 3 to 10-membered heterocycloalkyl group and a 5 to 10-membered aromatic heterocyclic group;

T represents an oxygen atom, a sulfur atom or a sulfonyl group; or TR$^1$ represents —SO$_2$NR$^{B3}$R$^{C3}$ in which R$^{B3}$ and R$^{C3}$ are independently a hydrogen atom or a lower alkyl group;

R$^2$ represents a di(lower alkyl)amino group, a lower alkyl group, a 3 to 10-membered cycloalkyl group, a 6 to 10-membered aryl group which may have one to three substituents selected from the following group (B), a 3 to 10-membered heterocycloalkyl group which may have an oxo group, or a 5 to 10-membered aromatic heterocyclic group which may have a substituent selected from the following group (C);

(B) an oxo group, a lower alkyl group, a halo(lower alkyl) group, —Y—R$^D$, a halogen atom, a nitro group, an amino group, —COOR$^E$, a carbamoyl group, a sulfamoyl group, a lower alkylsulfonyl group, a mono(lower alkyl)sulfamoyl group which may have —COOR$^F$, and a lower alkylsulfonylamino-substituted (lower alkyl) group;

wherein Y represents an oxygen atom or a sulfur atom;

R$^D$ represents a hydrogen atom, a halo(lower alkyl) group or a lower alkyl group which may have —COOR$^{D1}$ in which R$^{D1}$ is a hydrogen atom, a 3 to 10-membered cycloalkyl group or a lower alkyl group;

R$^E$ represents a hydrogen atom, a 3 to 10-membered cycloalkyl group or a lower alkyl group;

R$^F$ represents a hydrogen atom, a 3 to 10-membered cycloalkyl group or a lower alkyl group;

(C) a lower alkyl group, an amino group and —COOR$^G$;

wherein R$^G$ represents a hydrogen atom, a 3 to 10-membered cycloalkyl group or a lower alkyl group;

Q represents a hydrogen atom or a lower alkyl group which may have a substituent selected from the following group (D);

(D) —OR$^H$, —COOR$^I$, —CONR$^J$R$^K$, a 6 to 10-membered aryl group which may have one to three substituents selected from the following group (iii), and a 5 to 10-membered aromatic heterocyclic group which may have one to three substituents selected from the following group (iv);

wherein R$^H$ represents a hydrogen atom or a lower alkyl group which may have —OR$^{H1}$ in which R$^{H1}$ is a hydrogen atom or a lower alkyl group;

R$^I$ independently has the same meaning as R$^A$;

R$^J$ and R$^K$ independently represent a hydrogen atom, a 6 to 10-membered aryl group which may have a carbamoyl group, a 5 to 10-membered aromatic heterocyclic group which may have a substituent selected from the following group (v), or a lower alkyl group which may have a substituent selected from the following group (vi), or —NR$^J$R$^K$ forms a cyclic amino group which may have a substituent selected from the following group (vii);

(v) a halogen atom, a lower alkyl group, a carbamoyl group and —COOR$^{J1}$ in which R$^{J1}$ is a hydrogen atom or a lower alkyl group;

(vi) —OR$^{J2}$ in which R$^{J2}$ is a hydrogen atom or a lower alkyl group, and a 5 to 10-membered aromatic heterocyclic group;

(vii) a hydroxy group, a lower alkyl group, a hydroxy (lower alkyl) group, a carbamoyl group, a di(lower alkyl)amino group, a lower acyl group and —COOR$^{J3}$ in which R$^{J3}$ is a hydrogen atom or a lower alkyl group;

(iii) a halogen atom, a nitro group, a lower alkyl group, —OR$^L$ in which R$^L$ is a hydrogen atom or a lower alkyl group, and —COOR$^M$ in which R$^M$ is a hydrogen atom or a lower alkyl group;

(iv) a halogen atom, an oxo group, a lower alkyl group and a phenyl group; and

Z represents a hydrogen atom, a hydroxy group or —COOR$^N$;

wherein R$^N$ represents a halo(lower alkyl) group, a 6 to 10-membered aryl group, or a lower alkyl group which may have a substituent selected from the following group (viii);

(viii) —OR$^{N1}$ in which R$^{N1}$ is a hydrogen atom or a lower alkyl group, —COOR$^{N2}$ in which R$^{N2}$ is a lower alkyl group which may have —COOR$^{N21}$ where R$^{N21}$ is a lower alkyl group, —CONR$^{N3}$R$^{N4}$ in which R$^{N3}$ and R$^{N4}$ are independently a hydrogen atom or a lower alkyl group, or —NR$^{N3}$R$^{N4}$ forms a cyclic amino group, —OCOR$^{N5}$ in which R$^{N5}$ is a lower alkyl group which may have —OCOR$^{N51}$ where R$^{N51}$ is a lower alkyl group, a 3 to 10-membered heterocycloalkyl group and a 6 to 10-membered aryl group;

or a pharmaceutically acceptable salt thereof.

2. A 5-amidino-2-hydroxybenzenesulfonamide derivative as claimed in claim 1 or a pharmaceutically acceptable salt thereof, wherein Q is a hydrogen atom and Z is not a hydrogen atom.

3. A 5-amidino-2-hydroxybenzenesulfonamide derivative as claimed in claim 2 or a pharmaceutically acceptable salt thereof, wherein R is a lower alkyl group having —COOR$^A$ wherein R$^A$ is a hydrogen atom, a 3 to 10-membered cycloalkyl group or a lower alkyl group which may have a substituent selected from the following group (i);

(i) —COOR$^{41}$ in which R$^{41}$ is a hydrogen atom, a 3 to 10-membered cycloalkyl group or a lower alkyl group, —OCOR$^{42}$ in which R$^{42}$ is a 3 to 10-membered cycloalkyl group or a lower alkyl group, —OCOOR$^{43}$ in which R$^{43}$ is a 3 to 10-membered cycloalkyl group or a lower alkyl group, —OR$^{44}$ in which R$^{44}$ is a hydrogen atom, a 3 to 10-membered cycloalkyl group or a lower alkyl group, —CONR$^{45}$R$^{46}$ in which R$^{45}$ and R$^{46}$ are independently a hydrogen atom or a lower alkyl group, or —NR$^{45}$R$^{46}$ forms a cyclic amino group, a 3 to 10-membered cycloalkyl group, a 6 to 10-membered aryl group, a 3 to 10-membered heterocycloalkyl group and a 5 to 10-membered aromatic hetero cyclic group;

R$^2$ is a phenyl group having a substituent selected from the following group (B);

(B) an oxo group, a lower alkyl group, a halo(lower alkyl) group, —Y—R , a halogen atom, a nitro group, an amino group, —COOR$^E$, a carbamoyl group, a sufamoyl group, a lower alkylsulfonyl group, a mono(lower alkyl)sulfamoyl group which may have —COOR$^F$, and a lower alkylsulfonylamino-substituted (lower alkyl) group;

wherein Y is an oxygen atom or a sulfur atom;

R$^D$ is a hydrogen atom, a halo(lower alkyl) group or a lower alkyl group which may have —COOR$^{D1}$ in which R$^{D1}$ is a hydrogen atom, a 3 to 10-membered cycloalkyl group or a lower alkyl group;

R$^E$ is a hydrogen atom, a 3 to 10-membered cycloalkyl group or a lower alkyl group;

R$^F$ is a hydrogen atom, a 3 to 10-membered cycloalkyl group or a lower alkyl group; T is an oxygen atom; and Z is a hydroxy group.

4. A 5-amidino-2-hydroxybenzenesulfonamide derivative as claimed in claim 3 or a pharmaceutically acceptable salt thereof, wherein R¹ is a methyl group having —COOR⁴¹⁰ wherein R⁴¹⁰ is a 3 to 10-membered cycloalkyl group or a lower alkyl group; and R² is a phenyl group having a substituent selected from the group consisting of a sufamoyl group, a lower alkylsulfonyl group and a mono(lower alkyl)sulfamoyl group.

5. A 5-amidino-2-hydroxybenzenesulfonamide derivative as claimed in claim 1 or a pharmaceutically acceptable salt thereof, wherein R¹ is a lower alkyl group having —COOR⁴¹⁰ wherein R⁴¹⁰ is a 3 to 10-membered cycloalkyl group or a lower alkyl group;

R is a phenyl group having a substituent selected from the group consisting of a sufamoyl group, a lower alkylsulfonyl group and a mono(lower alkyl)sulfamoyl group;

Q is a hydrogen atom,

T is an oxygen atom; and

Z is a hydrogen atom.

6. The 5-amidino-2-hydroxybenzenesulfonamide derivative as claimed in claim 4, represented by the formula:

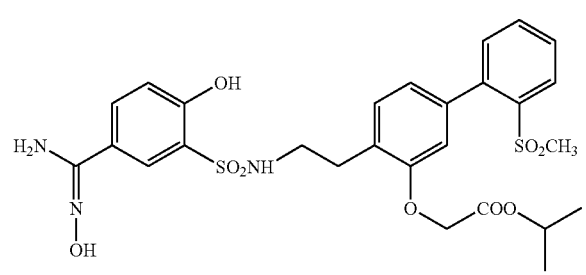

or a pharmaceutically acceptable salt thereof.

7. The 5-amidino-2-hydroxybenzenesulfonamide derivative as claimed in claim 4, represented by the formula:

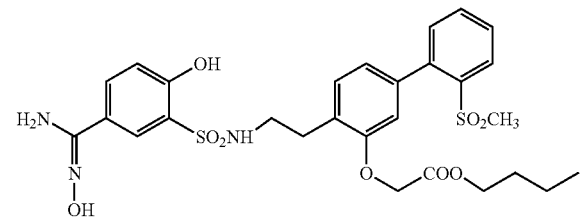

or a pharmaceutically acceptable salt thereof.

8. The 5-amidino-2-hydroxybenzenesulfonamide derivative as claimed in claim 4, represented by the formula:

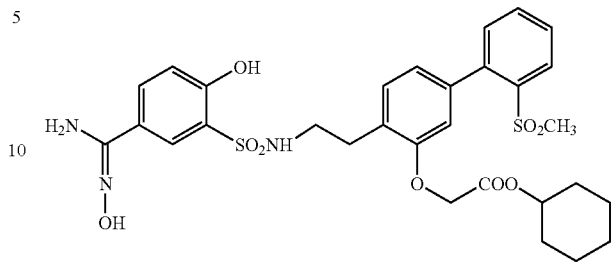

or a pharmaceutically acceptable salt thereof.

9. The 5-amidino-2-hydroxybenzenesulfonamide derivative as claimed in claim 4, represented by the formula:

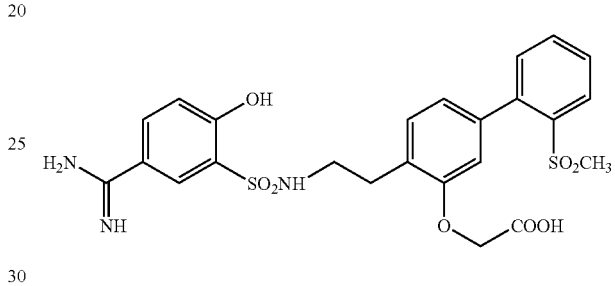

or a pharmaceutically acceptable salt thereof.

10. A pharmaceutical composition comprising as an active ingredient a 5-amidino-2-hydroxybenzenesulfonamide derivative as claimed in claim 1 or a pharmaceutically acceptable salt thereof.

11. A pharmaceutical composition as claimed in claim 10 wherein the composition is an activated blood coagulation factor X inhibitor.

12. A pharmaceutical composition as claimed in claim 10 wherein the composition is an agent for the treatment of a disease requiring inhibition of activated blood coagulation factor X.

13. A method for the manufacture of a pharmaceutical composition for the treatment of a disease requiring inhibition of activated blood coagulation factor X which comprises mixing a 5-amidino-2-hydroxybenzenesulfonamide derivative as claimed in claim 1 or a pharmaceutically acceptable salt thereof with a conventional pharmaceutical carrier.

* * * * *